(12) United States Patent
Liu et al.

(10) Patent No.: US 11,749,093 B2
(45) Date of Patent: Sep. 5, 2023

(54) SYSTEM AND METHOD FOR PREDICTING HYGIENE OPPORTUNITY AND HYGIENE ACTIONS FOR HYGIENE PROTOCOLS

(71) Applicant: Microsensor Labs, LLC, Chicago, IL (US)

(72) Inventors: Peng Liu, Chicago, IL (US); Yang Liu, Chicago, IL (US)

(73) Assignee: Microsensor Labs, LLC, Chicago, IL (US)

( * ) Notice: Subject to any disclaimer, the term of this patent is extended or adjusted under 35 U.S.C. 154(b) by 93 days.

(21) Appl. No.: 17/341,789

(22) Filed: Jun. 8, 2021

(65) Prior Publication Data

US 2021/0295673 A1    Sep. 23, 2021

Related U.S. Application Data

(60) Continuation-in-part of application No. 16/895,435, filed on Jun. 8, 2020, now Pat. No. 11,257,350, which
(Continued)

(51) Int. Cl.
*G08B 21/24* (2006.01)
*G06K 7/10* (2006.01)
(Continued)

(52) U.S. Cl.
CPC ....... *G08B 21/245* (2013.01); *G06K 7/10366* (2013.01); *G16H 40/20* (2018.01); *G01H 1/00* (2013.01); *G01P 15/18* (2013.01)

(58) Field of Classification Search
CPC .. G08B 21/245; G06K 7/10366; G16H 40/20; G01H 1/00; G01P 15/18
See application file for complete search history.

(56) References Cited

U.S. PATENT DOCUMENTS 5,870,015 A   2/1999   Hinkel
6,028,520 A   2/2000   Maehre
(Continued)

FOREIGN PATENT DOCUMENTS

EP    3118828 A1   1/2017
WO    2012037192 A1   3/2012
(Continued)

OTHER PUBLICATIONS

U.S. Office Action for U.S. Appl. No. 15/946,537 dated Oct. 18, 2018.
(Continued)

*Primary Examiner* — Hongmin Fan
(74) *Attorney, Agent, or Firm* — Lempia Summerfield Katz LLC

(57) ABSTRACT

A system and method for opportunity-based hygiene monitoring and/or reminding is disclosed. Healthcare providers may have various opportunities to interact with a patient. As such, an opportunity-based focus in managing a healthcare environment may assist in assessing the various opportunities when interacting with the patient. For example, an opportunity-based analysis may be used for protocol compliance, such as compliance with hand hygiene protocols and/or PPE protocols. Further, infection analysis, patient care billing, staff locating, or workload analysis may be opportunity based in order to more efficiently manage the healthcare environment.

15 Claims, 23 Drawing Sheets

Related U.S. Application Data is a continuation-in-part of application No. 16/148,683, filed on Oct. 1, 2018, now Pat. No. 10,679,488, which is a continuation-in-part of application No. 15/946,537, filed on Apr. 5, 2018, now Pat. No. 10,403,121, application No. 17/341,789 is a continuation-in-part of application No. 16/895,435, filed on Jun. 8, 2020, now Pat. No. 11,257,350, which is a continuation-in-part of application No. PCT/US2019/025751, filed on Apr. 4, 2019, application No. 17/341,789 is a continuation-in-part of application No. 16/895,435, filed on Jun. 8, 2020, now Pat. No. 11,257,350, which is a continuation-in-part of application No. 16/557,191, filed on Aug. 30, 2019, now Pat. No. 10,748,410, which is a division of application No. 15/946,537, filed on Apr. 5, 2018, now Pat. No. 10,403,121.

(60) Provisional application No. 62/482,146, filed on Apr. 5, 2017.

(51) Int. Cl.
*G16H 40/20* (2018.01)
*G01H 1/00* (2006.01)
*G01P 15/18* (2013.01)

(56) References Cited

U.S. PATENT DOCUMENTS

| | | | |
|---|---|---|---|
| 6,417,773 | B1 | 7/2002 | Vlahos et al. |
| 6,937,155 | B2 | 8/2005 | Ballard |
| 8,648,724 | B2 | 2/2014 | Forsberg et al. |
| 8,698,637 | B2 | 4/2014 | Raichman |
| 9,135,805 | B2 | 9/2015 | Freedman et al. |
| 9,483,930 | B1 | 11/2016 | Haaland |
| 9,695,981 | B2 | 7/2017 | Au |
| 9,747,760 | B2 | 8/2017 | Fletcher |
| 9,773,402 | B2 | 9/2017 | Raichman |
| 10,475,329 | B1 | 11/2019 | Koester et al. |
| 2004/0001009 | A1 | 1/2004 | Winings et al. |
| 2004/0090333 | A1 | 5/2004 | Wildman et al. |
| 2006/0191068 | A1 | 8/2006 | Vlahos et al. |
| 2008/0131332 | A1 | 6/2008 | Nguyen |
| 2009/0195385 | A1 | 8/2009 | Huang |
| 2010/0073162 | A1 | 3/2010 | Johnson et al. |
| 2010/0164728 | A1 | 7/2010 | Plost |
| 2011/0193703 | A1 | 8/2011 | Payton |
| 2011/0254682 | A1 | 10/2011 | Sigrist |
| 2012/0062382 | A1 | 3/2012 | Taneff |
| 2012/0256742 | A1 | 10/2012 | Snodgrass |
| 2012/0268277 | A1 | 10/2012 | Best |
| 2013/0300572 | A1 | 11/2013 | Mould-millman |
| 2014/0266692 | A1 | 9/2014 | Freedman |
| 2014/0313055 | A1 | 10/2014 | Warkentin et al. |
| 2014/0345726 | A1 | 11/2014 | Seggio et al. |
| 2015/0254964 | A1* | 9/2015 | Raichman .............. A61G 11/00 340/573.1 |
| 2015/0278456 | A1 | 10/2015 | Bermudez Rodriguez |
| 2016/0140832 | A1 | 5/2016 | Moore |
| 2016/0180695 | A1 | 6/2016 | Levchenko et al. |
| 2016/0324460 | A1 | 11/2016 | Kusens |
| 2016/0379456 | A1 | 12/2016 | Nongpiur et al. |
| 2017/0004287 | A1 | 1/2017 | O'Toole |
| 2017/0018167 | A1 | 1/2017 | Dey |
| 2017/0084161 | A1 | 3/2017 | Dey |
| 2017/0294106 | A1 | 10/2017 | Thyroff |
| 2017/0372216 | A1 | 12/2017 | Awiszus |
| 2018/0122214 | A1 | 5/2018 | Freedman |
| 2018/0151054 | A1 | 5/2018 | Pi |
| 2018/0357886 | A1* | 12/2018 | Tavori .................. G16H 40/20 |
| 2019/0314843 | A1 | 10/2019 | Nour-omid |
| 2020/0321104 | A1 | 10/2020 | Lindström |

FOREIGN PATENT DOCUMENTS

| | | |
|---|---|---|
| WO | 2015179262 A1 | 11/2015 |
| WO | 2017011911 A1 | 1/2017 |
| WO | 2017094016 A1 | 6/2017 |

OTHER PUBLICATIONS

Z. A. Shhedi, A. Moldoveanu and F. Moldoveanu, "Traditional and ICT Solutions for Preventing the Hospital Acquired Infection," 2015 20th International Conference on Control Systems and Computer Science, 2015, abstract, doi: 10.1109/CSCS.2015.125.

European Search Report for European application No. 21178142.2-1206/3958232 dated Mar. 18, 2022.

European Search Report for European application No. 19868736.0-1205 / 3861540 PCT/US2019025751 dated May 12, 2022.

* cited by examiner

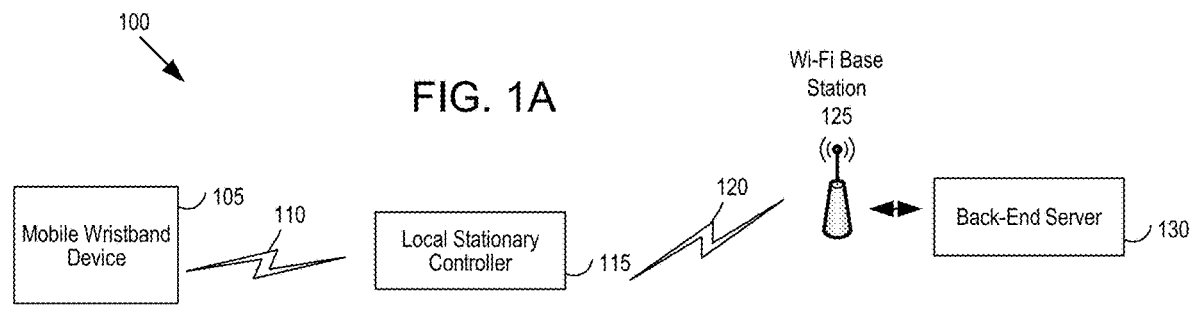
FIG. 1A
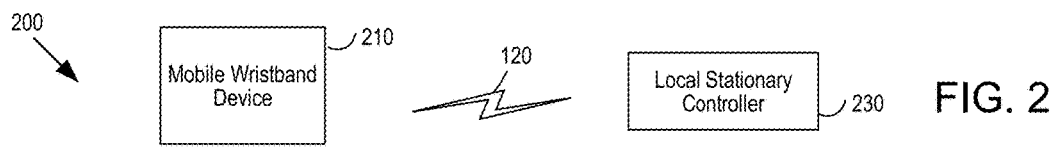
FIG. 2
FIG. 5
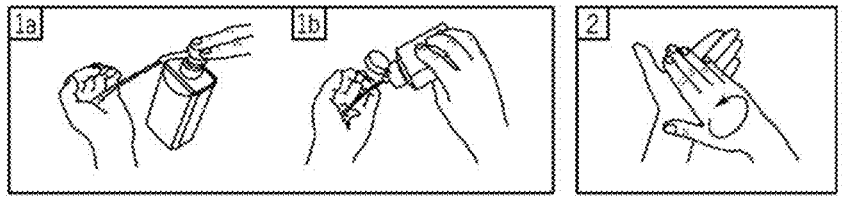
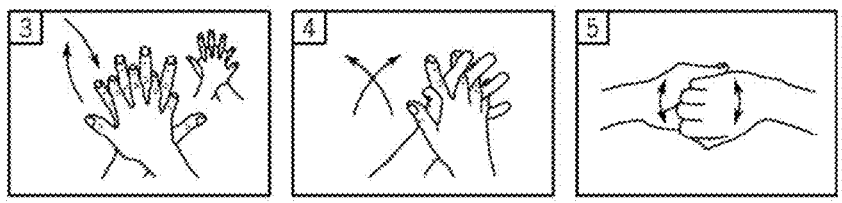
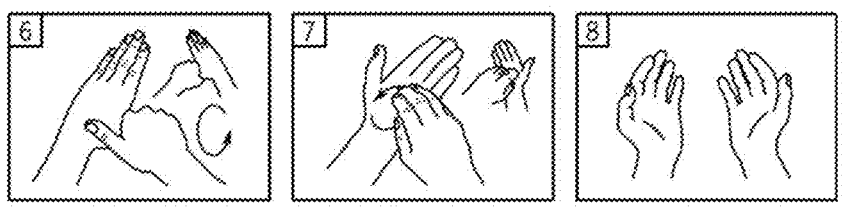

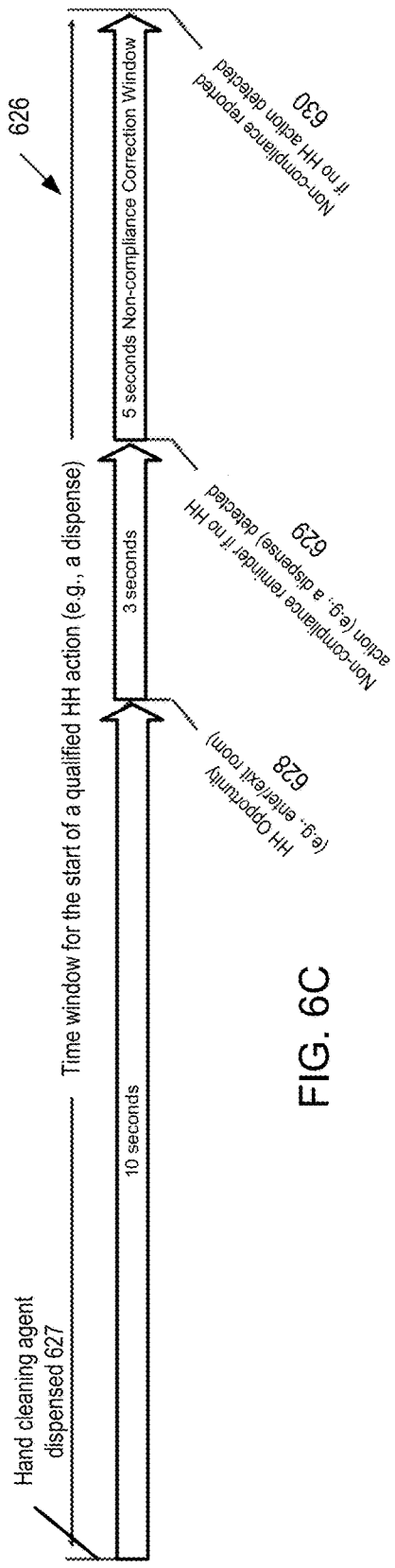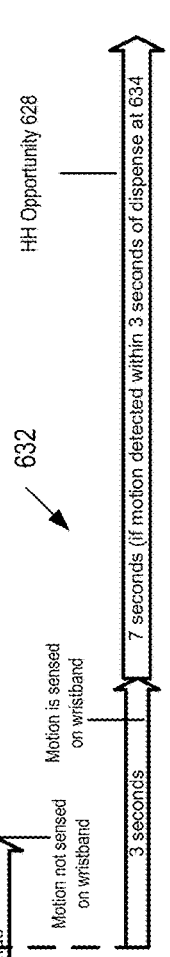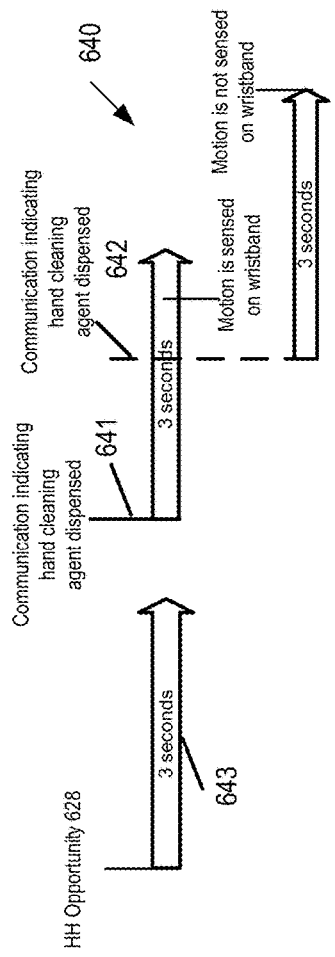

SYSTEM AND METHOD FOR PREDICTING HYGIENE OPPORTUNITY AND HYGIENE ACTIONS FOR HYGIENE PROTOCOLS

REFERENCE TO RELATED APPLICATIONS

This application is a continuation in part of U.S. patent application Ser. No. 16/895,435, which is a continuation in part of U.S. patent application Ser. No. 16/148,683 (now U.S. Pat. No. 10,679,488) filed on Oct. 1, 2018, which is a continuation in part of U.S. patent application Ser. No. 15/946,537 (now U.S. Pat. No. 10,403,121) filed on Apr. 5, 2018, which claims priority to U.S. Provisional Patent Application No. 62/482,146 filed on Apr. 5, 2017. This application also claims priority via U.S. patent application Ser. No. 16/895,435 to and is a continuation in part of PCT Application No. PCT/US19/25751 filed on Apr. 4, 2019 (published as WO 2020/072096 A1). This application further claims priority via U.S. patent application Ser. No. 16/895,435 and is a continuation in part of U.S. patent application Ser. No. 16/557,191 (now U.S. Pat. No. 10,748,410) filed on Aug. 30, 2019, which is a division of U.S. patent application Ser. No. 15/946,537 (now U.S. Pat. No. 10,403,121) filed on Apr. 5, 2018, which claims priority to U.S. Provisional Patent Application No. 62/482,146 filed on Apr. 5, 2017. Each of U.S. patent application Ser. No. 16/148,683 (now U.S. Pat. No. 10,679,488), U.S. patent application Ser. No. 15/946,537 (now U.S. Pat. No. 10,403,121), U.S. Provisional Patent Application No. 62/482,146, U.S. patent application Ser. No. 16/557,191 (now U.S. Pat. No. 10,748,410), and PCT Application No. PCT/US19/25751 (published as WO 2020/072096 A1) are incorporated by reference herein in their entirety.

GOVERNMENT LICENSE RIGHTS

This invention was made with United States government support under grant number 1R43NR017373-01A1 and grant number 1R44AG060848-01 awarded by the National Institutes of Health (NIH) Small Business Innovation Research (SBIR). The United States Government has certain rights in the invention.

BACKGROUND

Healthcare-Associated Infections (HAIs) imposes devastating medical and economic consequences. Severe HAIs lead to extended hospital stays, lasting side effects and ultimately increased costs and risks of mortality. Treating these infections costs the healthcare system billions of dollars every year.

A good personal protective equipment practice is important to reduce transmission of pathogenic microorganisms to patients and to protect workers (e.g., pursuant to Occupational Safety and Health Administration (OSHA) standards). For example, healthcare providers may wear various types of personal protective equipment, such as any one, any combination, or all of: gloves, mask, gown, or protective eyewear. Typically, the personal protective equipment is placed outside of a patient's room for the healthcare provider to wear.

BRIEF DESCRIPTION OF THE DRAWINGS

The accompanying drawings, which are incorporated in and constitute a part of this specification, illustrate various aspects of the invention and together with the description, serve to explain its principles. Wherever convenient, the same reference numbers will be used throughout the drawings to refer to the same or like elements.

FIG. 1A is a first example block diagram of a hand hygiene and/or PPE system, with a mobile wristband device, a local stationary controller and a back-end server.

FIG. 2 is another example block diagram of a hand hygiene system, with a mobile wristband device and a local stationary controller.

FIG. 5 illustrates a series of pictures which highlights the recommended hand rubbing techniques with alcohol-based formulation in World Health Organization (WHO) guidelines on hand hygiene in healthcare, with the duration of the hand hygiene motions (picture #2-7) recommended to last 20-30 seconds. Thus, the alcohol-based hand rub (ABHR) is one example of a hand hygiene technique. Another example of a hand hygiene technique is using soap (or other type of cleaning product) and water.

FIG. 6C is a first timing diagram for determining whether there is sufficient connection between the detected HH action and the detected HH opportunity.

FIG. 6D is a second timing diagram for determining whether there is sufficient connection between the detected HH action and the detected HH opportunity.

FIG. 6E is a third timing diagram for determining whether there is sufficient connection between the detected HH action and the detected HH opportunity.

DETAILED DESCRIPTION OF EMBODIMENTS

Overview

Figure 1B:
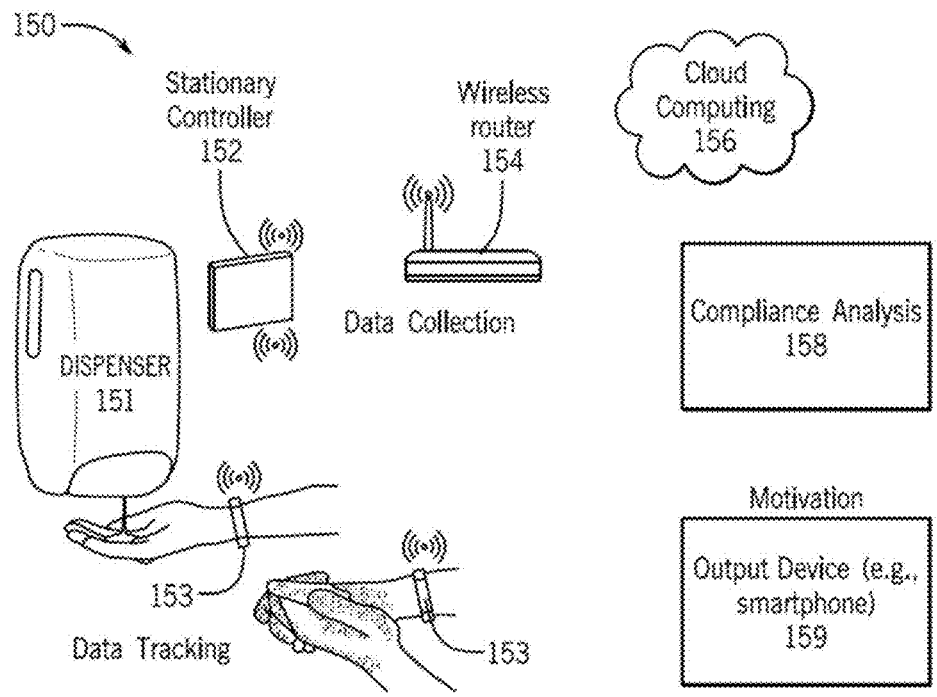
FIG. 1B is a second example block diagram of a hand hygiene system, with a mobile wristband device, a dispenser, a local stationary controller, compliance analysis, one or more output devices, and cloud computing.

Healthcare providers often are presented with opportunities for patient interaction. For example, the WHO lists five hygiene opportunities for infection control, as discussed in more detail below. In those opportunities, the healthcare providers may need to follow one or more protocols, such as one or more hand hygiene (HH) protocols and/or patient protective equipment (PPE) protocols. Compliance may with the protocol(s) may include one or more steps. Example steps include any one, any combination, or all of: taking hand cleaning agent (e.g., taking hand sanitizer); taking PPE (e.g., opening a drawer or cabinet containing gloves, masks, etc.); performing one or more hand movements and/or the one or more hand movements in a sequence (e.g., performing hand rubbing for at least 20 seconds; upon entrance to a patient area, first cleaning hands prior to donning PPE; etc.). These steps are merely listed by way of example. Other steps are contemplated. Any one, any combination, or all of those steps may be used to identify a hygiene action, such as one or both of a HH action or a PPE action. As one example, taking sanitizer from a dispenser may comprise a HH action and may be a trigger identifying a HH action. As another example, opening a drawer that contains gloves may comprise a hygiene action and may be a trigger identifying a PPE action. Thus, in a more specific embodiment, the trigger for the hygiene action may comprise a predicate step (such as an initial step) in order for the healthcare provider to comply with the protocol (e.g., the healthcare provider performing the predicate step of taking sanitizer in preparation for rubbing hands to comply with the HH protocol; the healthcare provider performing the predicate step of opening the drawer containing gloves in preparation for putting on the gloves in order to comply with the PPE protocol).

However, identifying and detecting a hygiene action may occur at different times (e.g., identifying the hygiene opportunity may occur before or after detecting the hygiene action), thereby complicating matters. As discussed in more detail below, the hygiene opportunity may comprise an opportunity for practicing proper hygiene with a patient that may be identified based on identifying behavior indicative of patient interaction associated with one or more hygiene opportunities. Further, as discussed in more detail below, a hygiene action comprises an event for performing proper hygiene. The hygiene action may be detected in one of several ways, such as by sensing one or more of the acts for complying with the hygiene action, including by: detecting sanitizer being dispensed from a dispenser; detecting opening/taking of PPE from a PPE container. By way of example, a healthcare worker may potentially have dozens or hundreds of interactions with others in the course of a single day. In order to focus the compliance analysis, a subset of those interaction are identified as being hygiene opportunities, which may be those interactions where guidelines, such as the WHO guidelines, are to be followed. The hygiene actions, with the various steps following those guidelines, may, in turn, be used to determine compliance.

In one or some embodiments, reminders may be generated for healthcare workers according to any one, any combination, or all of the following: responsive to identifying a hygiene opportunity; responsive to identifying a hygiene action; responsive to identifying both a hygiene opportunity and a hygiene action; responsive to detecting a hygiene opportunity and responsive to a determination of compliance or non-compliance with the hygiene opportunity (e.g., providing a reminder as feedback indicating non-compliance (e.g., failure to take sanitizer), indicating partial compliance (e.g., taking sanitizer but failing to perform the requisite 20 seconds of hand rubbing required by the HH protocol); and/or indicating full compliance (e.g., full compliance with one or both HH protocol or PPE protocol); or responsive to detecting a hygiene action and responsive to a determination of compliance or non-compliance with the hygiene action.

As one example, in one or some embodiments, a reminder may be generated immediately responsive to identifying the hygiene opportunity. In one particular example, an area, such as a patient room, may have associated with it a hygiene protocol (such as a HH protocol and/or a PPE protocol), with the hygiene protocol either being non-changing or changing. Responsive to identifying the opportunity (and before any determination of partial or full compliance), an output may be generated to remind the healthcare worker as to the hygiene protocol associated with the area. In another particular example, the area may have a changing hygiene protocol (e.g., the hygiene protocol(s) associated with the patient room change based on the diagnosis of the patient assigned to the patient room). Rather than relying on a handwritten note at the entrance to the patient room and the healthcare worker seeing the handwritten note, responsive to identifying the opportunity (such as responsive to identifying an exit opportunity from the patient room), a reminder may be output as to the changing hygiene protocol (e.g., responsive to identifying the healthcare worker exiting the patient room, generating an output as to the HH protocol to use soap/water to clean hands (the HH protocol associated with the patient room due to a diagnosis of the patient in the patient room)). Alternatively, the reminder may be generated responsive to identifying the opportunity and responsive to meeting one or more other criteria (e.g., only output the reminder responsive to identifying the opportunity and based on the status of the healthcare worker, such outputting the reminder if the healthcare worker is a trainee; only output the reminder responsive to identifying the opportunity and if there has been a change in the protocol associated with the patient area (e.g., the HH protocol has changed within X days of the identification of the opportunity); only output the reminder responsive to identifying the opportunity and based on the whether the specific healthcare worker has or has not been reminded of the protocol associated with the patient area (e.g., if the healthcare worker has already been reminded of the protocol associated with the patient area, such as having been reminded within X amount of time, do not generate the reminder responsive to identifying the opportunity; if the healthcare worker has already been reminded a predetermined number of times (such as at least two times) of the protocol associated with the patient area, such as having been reminded the predetermined number of times within X amount of time, do not generate the reminder responsive to identifying the opportunity); alternatively, responsive to the healthcare worker not having already been reminded of the protocol associated with the patient area, such as not having been reminded within X amount of time, generating the reminder responsive to identifying the opportunity).

Alternatively, the reminder may be associated with or dependent on compliance with the hygiene opportunity (e.g., a failure to take sanitizer within 3 seconds of identifying the HH opportunity results in an output being generated indicating non-compliance, as discussed below; compliance with taking sanitizer within 3 seconds of identifying the HH opportunity results in an output being generated indicating compliance). As one example, responsive to a failure to detect the predicate step within a certain time period of identifying the HH opportunity (whether before or after identifying the HH opportunity) results in generating an output indicative of a reminder to perform the predicate step (e.g., an output indicative to "take sanitizer"). As another example, responsive to failure to detect a step in the compliance process (separate from the predicate step), an output may be generated (e.g., failure to detect hand rubbing for at least 20 seconds required by the hand hygiene protocol results in an output being generated indicative to the healthcare provider to rub for at least 20 seconds; failure to detect a certain hand rubbing motion required by the hand hygiene protocol results in an output being generated indicative to the healthcare provider to perform the certain hand rubbing motion; failure to detect a proper sequence (e.g., failure to perform hand sanitizing/PPE in proper sequence); etc.). As discussed further, the output may be generated on a mobile electronic device associated with the healthcare provider (e.g., a wristband) and/or on a stationary controller associated with the patient area, as discussed further below.

Alternatively, or in addition to generating reminders (as discussed herein), in one or some embodiments, compliance determination(s) may be performed according to any one, any combination, or all of the following: responsive to identifying a hygiene opportunity; responsive to identifying a hygiene action; or responsive to identifying both a hygiene opportunity and a hygiene action.

As discussed in further detail below, the detection of hand hygiene compliance and the detection of personal protective equipment compliance may be performed separately from one another, or may be performed in combination with one another. For example, in one implementation, the system may only detect hand hygiene compliance (without detecting personal protective equipment compliance). In another implementation, the system may only detect personal protective equipment compliance (without detecting hand hygiene compliance). In still another implementation, the system may detect both hand hygiene compliance and personal protective equipment compliance. In a specific implementation, the detection of the hand hygiene (HH) compliance and the detection of personal protective equipment (PPE) compliance may at least be partly dependent on one another, as discussed in further detail below. As one example, the trigger to detect HH compliance and PPE compliance may be dependent on one another (e.g., a common trigger for both HH compliance and PPE compliance; a trigger for HH compliance in turn results in a trigger for PPE compliance; a trigger for PPE compliance in turn results in a trigger for HH compliance). As another example, the detection of movements for HH compliance and PPE compliance may be dependent on one another (e.g., movements are checked for HH compliance and thereafter movements are checked for PPE compliance; movements are checked for PPE compliance and thereafter movements are checked for HH compliance).

By way of background, both the World Health Organization (WHO) and the Centers for Disease Control (CDC) provide detailed hand hygiene techniques and durations in their guidelines that are intended to be implemented in all healthcare settings. For instance, in WHO guidelines on hand hygiene in healthcare, hand hygiene with alcohol-based formulation is recommended for routine hygienic hand antisepsis with various hand-rubbing motions lasting for 20-30 seconds. One example hand hygiene technique is handwashing using soap and water. Another hand hygiene technique is hand rubbing, such as with alcohol-based formulations. As used herein, any discussion for hand hygiene is applicable to both handwashing and hand rubbing. Likewise, any discussion regarding hand rubbing is applicable to handwashing, and any discussion regarding handwashing is applicable to hand rubbing.

An example of this is illustrated in FIG. 5, which illustrates the recommended hand rubbing techniques with alcohol-based formulation in WHO guidelines on hand hygiene in healthcare, with the duration of the hand hygiene motions (as shown in pictures #2-7 of FIG. 5) that is recommended to last 20-30 seconds. In contrast, handwashing with soap is recommended for cleaning soiled hands, with the same hand-rubbing motions plus extra steps of rinsing and drying, for a total duration of 40-60 seconds. Thus, in one implementation, the hand movements associated with cleaning hands using the alcohol based-formulation is the same as the hand movements associated with cleaning hands using soap/water (e.g., pictures #2-7 of FIG. 5). Alternatively, different hand movements are required for cleaning hands using the alcohol based-formulation versus using soap/water.

Separate from, or in combination with, movements may be monitored for compliance with one or more PPE protocols. As discussed above, to reduce the spread of diseases, healthcare providers may don personal protective equipment (e.g., gloves, gown, mask, protective eyewear). The wearing of the personal protective equipment may be dictated by the one or more PPE protocols. In this regard, compliance with PPE protocols may be recommended in certain situations when interacting with patients. Further, any discussion herein regarding compliance by and/or reminders to a healthcare provider may equally apply to other types of workers, such as construction workers, factory workers, or the like.

Donning PPE may include first putting on a gown, then putting on protective face wear (e.g., first a mask and then google), and finally putting on gloves, while doffing PPE includes first removing the gloves, then removing the gown, and finally removing the protective face wear. Combinations of PPE types (e.g., gloves, masks, goggle, respirator, gown or apron) are available to protect all or parts of the healthcare provider from contact with potentially infectious material. For instance, gloves protect the hands; gowns or aprons protect the skin and/or clothing; masks and respirators protect the mouth and nose; goggles protect the eyes; and face shields protect the entire face. The selection of PPE may be determined by the isolation precautions required for the patient and/or the nature of the patient contact. The Centers for Disease Control and Prevention (CDC) have suggested steps for donning and removing PPEs. Specifically, the CDC recommends donning or doffing PPEs in the proper steps to prevent contamination of skin and clothing.

In one implementation, a hand hygiene monitoring system and method is disclosed. The hand hygiene monitoring system may be used in various settings, such as in a hospital setting, a nursing home setting, a home setting, a service-based setting (such as a restaurant), or the like. In a first specific implementation, the hand hygiene monitoring system comprises one or more mobile electronic devices and one or more stationary electronic devices. The mobile electronic device may be configured to be attached or associated (such as by the shape of the mobile electronic device or a hook, clip, strap, or band associated with the electronic device) with a person, such as a healthcare provider, a service provider, a child, an elderly person, or the like. As discussed in more detail below, the mobile electronic device in one implementation may comprise a wristband electronic device configured to be worn on a person's wrist (such as partly or entirely encircling the wrist). Alternatively, the mobile electronic device may be attached to other parts of the person's body. The stationary electronic device may be fixedly attached to a part of a premises. The part of the premises may be itself stationary (such as a stationary hand cleaning agent dispenser) or may move (such as a door or a drawer). For example, as discussed in more detail below, the stationary electronic device may be fixedly attached in relation to a hand cleaning agent dispenser (e.g., as part of (or within) the hand cleaning agent dispenser or in fixed relation and proximate to or adjacent to the hand cleaning agent dispenser). In a second specific implementation, the hand hygiene monitoring system comprises one or more mobile electronic devices, one or more stationary electronic devices, and central analytics. The central analytics may be configured to analyze one or more aspects of the hand hygiene monitoring system, as discussed further below.

Discussed below are various applications of the wristband. Any discussion below regarding the wristband comprises a wristband electronic device, and may likewise be applied to any other type of electronic device, such as another type of wearable electronic device, that can be attached or otherwise associated with the person that may measure hand movements or other type of body movements of the healthcare provider. Further, any discussion regarding the mobile electronic device, such as the wristband, may likewise be applied to a PPE compliance system. In this regard, any discussion herein regarding the mobile electronic device, including tracking movements or the electronics therein, for use in a hand hygiene compliance system may likewise be applied to a PPE compliance system and/or to a hand hygiene/PPE compliance system.

The wristband may record sensor data from one or more sensors. In one implementation, the wristband includes a single motion sensor. In an alternate implementation, the wristband includes multiple motion sensors, such as a first type of motion sensor and a second type of motion sensor, with the first type of motion sensor being different than the second type of motion sensor.

Responsive to the one or more sensors generating sensor data, the sensor data may be analyzed. In one implementation, the wristband analyzes the sensor data, with the wristband making the determination, based on the analysis, whether the hand movements were sufficient or insufficient according to the guidelines. Thereafter, the wristband may output the determination (e.g., generating an output indicative of the sufficiency and/or insufficiency of the hand movements according to the guidelines, whether for hand hygiene and/or PPE) and may transmit the determination (e.g., sufficiency and/or insufficiency of hand movements according to the guidelines) to an external device, such as the stationary controller and/or the back-end analytics. In another implementation, the stationary controller receives the sensor data from the wristband and analyzes the sensor data, thereby making the determination as to sufficiency and/or insufficiency of hand movements. Thereafter, the stationary controller transmits the determination (e.g., sufficiency and/or insufficiency of hand movements according to the guidelines) to an external device, such as the wristband (for outputting an indication of sufficiency and/or insufficiency according to the guidelines) or the back-end analytics. Alternatively, or in addition, the stationary controller may determine both whether hand cleaning agent (such as sanitizer, soap, or the like) has been dispensed and whether the hand movements were sufficient to meet compliance. In still an alternate implementation, the stationary controller may determine whether a PPE garment (e.g., mask, gown, or the like) has been dispensed or removed and whether the hand movements were sufficient to meet compliance with putting on the PPE garment. In still another implementation, the back-end analytics receives the sensor data from the wristband and analyzes the sensor data, thereby making the determination as to sufficiency and/or insufficiency of hand movements according to the guidelines. Thereafter, the back-end analytics may transmit the determination (e.g., sufficiency and/or insufficiency of hand movements) to an external device, such as the wristband (for outputting an indication of sufficiency and/or insufficiency) or the stationary controller.

Alternatively, more than one device may determine hand hygiene and/or PPE compliance. As one example, the wristband and the stationary controller, in combination, may determine hand hygiene and/or PPE compliance. Specifically, the stationary controller may determine whether hand cleaning agent (such as sanitizer, soap, or the like) has been dispensed, and the wristband may determine whether the hand movements were sufficient (e.g., the hand movements were for at least a predetermined amount of time; the hand movements were at least a certain level of vigorousness (e.g., as measured by an accelerometer); or the hand movements with a certain level of vigorousness were for at least the predetermined amount of time). As another example, the wristband and the back-end analytics, in combination, may determine hand hygiene and/or PPE compliance. In particular, the wristband may send the movements (e.g., the hand movements, the PPE movements, or both the hand movements and the PPE movements) to a server, with the server configured to analyze the movements for compliance (e.g., analyze the hand movements for hand hygiene compliance, analyze the PPE movements for PPE compliance, or analyze both the hand movements and the PPE movements for hand hygiene and PPE compliance). Alternatively, or in addition, the stationary controller may send data (such as sound data regarding whether the hand cleaning agent has been dispensed) to the server, with the server analyzing the data. Thus, any discussion herein with regard to determination of compliance resident in the wristband and/or in the stationary controller (whether hand hygiene compliance, PPE compliance, or hand hygiene and PPE compliance in combination) may likewise be applied to a server performing those determinations of compliance. Alternatively, the stationary controller may determine whether the PPE garment (such as the mask, gown, gloves, etc.) has been dispensed and/or removed, and the wristband may determine whether the hand movements were sufficient (e.g., the hand movements indicate that the PPE garment was put on. As another example, the wristband and the back-end analytics, in combination, may determine PPE compliance. In still an alternate implementation, more than one device may determine both hand hygiene and PPE compliance.

As discussed above, the analytics may analyze the sensor data in one or more respects to determine hand hygiene and/or PPE compliance. In one implementation, the analytics may determine whether or not the person performed any act related to hand washing (such as whether the hand cleaning agent was dispensed from the dispenser) and/or any act related to PPE (such as whether the PPE garment was dispensed). In another implementation, the analytics may determine a duration of the hand hygiene motions and/or a duration of the PPE motions. As discussed in more detail below, the wristband (and/or the stationary controller) may analyze sensor output from the motion sensor(s) (such as the accelerometer) to determine whether the sensor output is indicative of hand hygiene motions (as opposed to other hand motions) and/or PPE motions for a predetermined amount of time (e.g., for 20 seconds).

In still another implementation, the method and system limits analysis to a discrete window of sensor data. In particular, various triggering events are contemplated, such as identifying a hygiene opportunity, detecting a hygiene action, or both detecting a hygiene action and identifying a hygiene opportunity. For example, a triggering event may identify a potential hand hygiene action and/or a potential PPE action, thereby beginning the sequence of analyzing the sensor data for the hand hygiene action and/or the PPE action. As discussed in more detail below, the wristband and the stationary controller work in combination for the triggering event. In one example, the stationary controller sends a beacon. Responsive to the wristband coming within range of near-field communication (e.g., within Bluetooth communication range for at least a predetermined amount of time), the wristband may be triggered to record sensor data in order to determine whether hand hygiene movements and/or PPE movements have occurred (e.g., the wristband may be triggered to perform any one, any combination, or all of: waking up from sleep mode to begin generating motion data; begin saving the generated motion data; begin analyzing the motion data for compliance; transmit to an external device (e.g., the stationary controller and/or the server) the determination indicating whether the motion data indicates compliance, partial compliance or non-compliance). In another example, the wristband may send a beacon, such as a Bluetooth signal or RFID signal. The stationary controller may sense the signal (e.g., the stationary controller may determine, based on the strength of the beacon, how close the wristband is to the stationary controller). Responsive to the stationary controller determining that the wristband is proximate (e.g., within a predetermined distance for at least a predetermined amount of time), the stationary controller may transmit a wake-up signal to the wristband as a trigger (e.g., the wristband may be triggered to perform any one, any combination, or all of: waking up from sleep mode to begin generating motion data; begin recording or saving the generated motion data; begin analyzing the motion data for compliance; transmit to an external device (e.g., the stationary controller and/or the server). Further, the analysis of the sensor data generated within the discrete window may be based on a contrast of hand hygiene motions and/or PPE motions with other periodic motions that may occur within the discrete window. As one example, the time period associated with the discrete window may be 60 seconds from identifying the hygiene opportunity and/or detecting the triggering event (e.g., when the healthcare provider is walking into a patient's room). In that regard, the analysis may focus on contrasting hand hygiene movements and/or PPE movements with other periodic movements that may be performed within the 60 second discrete window (e.g., walking, knocking on a door, etc.). For example, the analysis may focus on frequency and/or power to differentiate hand hygiene movements and/or PPE movements with other periodic movements. In this regard, accuracy of analysis may be increased by: (1) using data in the discrete window; and (2) analyzing hand hygiene actions and/or PPE actions and contrasting those hand hygiene actions and/or PPE actions without other periodic actions (e.g., walking, knocking on door) within that discrete window.

Figure 4A:
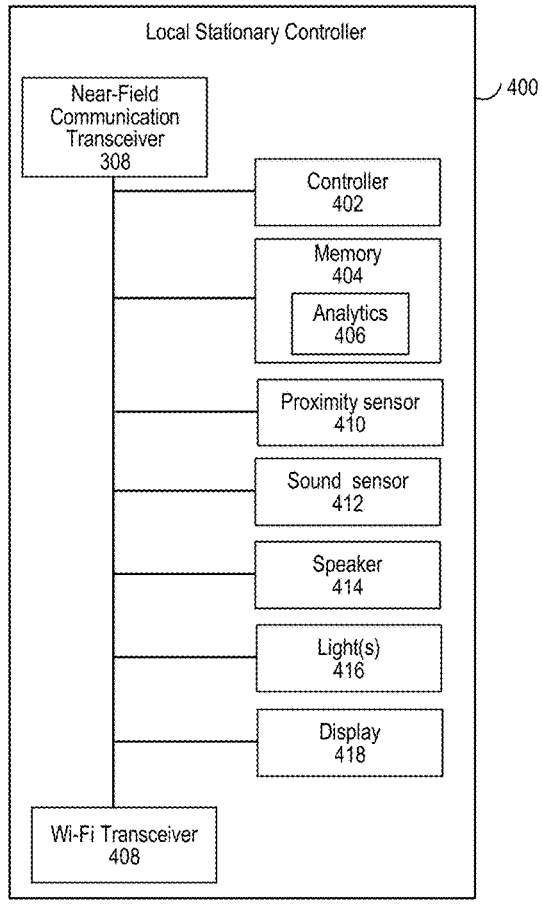
FIG. 4A is a first example block diagram of the local stationary controller.
Figure 4B:
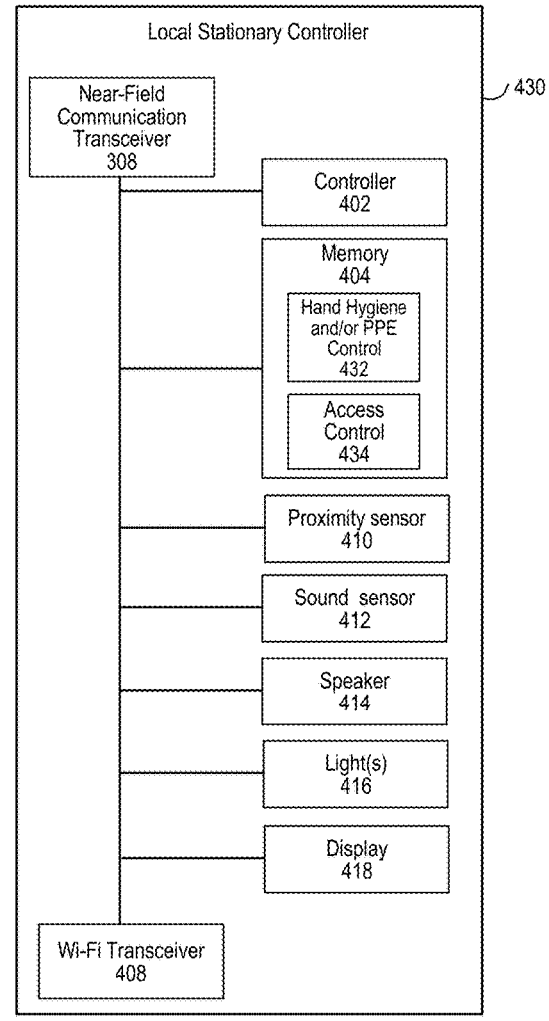
FIG. 4B is a second example block diagram of the local stationary controller.

In the present implementation, the motion sensor may operate for a very short time (~1 minute) only when a hygiene opportunity is identified and/or a hand hygiene action and/or PPE action is detected (such as by the stationary controller as illustrated in FIGS. 4A-B). For most of the time, at least a part of the wristband, such as one or more of the motion sensors within the wristband, is in sleep mode. For example, within sleep mode, power may be reduced or completely withheld from one or more parts of the wristband, such as the motion sensor. This achieves both low power dissipation and reliable hygiene compliance and/or PPE compliance detection. Selection of low-power chips further reduces the wristband's power consumption, as discussed further below. In particular, since the wristband is activated in the discrete window, the wristband may have a longer battery life, thereby reducing the burden from the healthcare provider to recharge or replace the battery as often. Further, since the wristband is activated in the discrete window, the wristband may focus on events that may occur within the window, thereby more accurately detecting compliance during a hand hygiene action and/or hygiene opportunity, and avoiding false alarms from any interfering motions (e.g., walking) or motions in a non-hygiene action and/or non-PPE action.

Further, in one implementation, the wristband may operate in a sleep mode (in which a part of the electronics within the wristband are turned off or are consuming less power) and may operate in a normal mode (in which some or all of the electronics within the wristband that are turned off or are consuming less power in sleep mode are turned on or consume a greater amount of power). As one example, the wristband may include one or more sensors, with some or all of the sensors being turned off or inactive in sleep mode, and some or all of the sensors being turned on or active in normal mode.

In still another implementation, one or more operations of hand hygiene and/or PPE monitoring may be divided amongst the wristband and the stationary controller. As discussed in more detail below, the stationary controller may be associated with the dispenser (e.g., antibacterial dispenser) and/or the entrance of the room. For example, one operation of hand hygiene and/or PPE monitoring is a trigger for beginning the hand hygiene and/or PPE monitoring. In this example, one of the wristband or the stationary controller may send a beacon, and another of the wristband or the stationary controller may detect the beacon, thereby triggering the beginning of the hand hygiene and/or PPE monitoring. In particular, the wristband may send an RFID or Bluetooth signal, which may be sensed by the stationary controller. In the example of Bluetooth, the stationary controller, based on the signal strength of the Bluetooth signal and/or the time elapsed of receiving the Bluetooth signal, may determine the closeness of the devices to one another. In response to the stationary controller determining that the wristband is within a predetermined distance for a predetermined period of time, the stationary controller may send a wake-up signal to the wristband to begin monitoring for hand hygiene and/or PPE movements. In another implementation, the stationary controller may transmit a beacon, which upon receipt by the wristband wakes up at least a part of the wristband, such as the motion sensor(s) on the wristband. More specifically, in one implementation, responsive to the wristband sensing the beacon signal from the stationary controller for a predetermined amount of time, the wristband may wake-up the motion sensor(s) on the wristband. Alternatively, or in addition, identification of a hygiene opportunity (such as by the wristband and/or the stationary controller) may trigger the wake-up of the wristband and/or the stationary controller.

Alternatively, or in addition, the hand hygiene and/or PPE monitoring system may generate one or more outputs associated with the hand hygiene and/or PPE monitoring. A first output may be generated to alert the healthcare provider to perform the hand hygiene and/or PPE movements (e.g., responsive to identifying a hygiene opportunity and/or a hygiene action). A second output may be generated to alert the healthcare provider as to whether the hand hygiene and/or PPE movements were sufficient and/or insufficient. In one implementation, the stationary controller may generate the alert to the healthcare provider to perform the hand hygiene and/or PPE movements, and the wristband may generate the alert to the healthcare provider as to whether the hand hygiene and/or PPE movements were sufficient and/or insufficient. Alternatively, the wristband may generate the alert to the healthcare provider to perform the hand hygiene and/or PPE movements, and the stationary controller may generate the alert to the healthcare provider as to whether the hand hygiene and/or PPE movements were sufficient and/or insufficient. In either implementation, the alerts may be divided amongst the stationary controller and the wristband. In still another implementation, only one device (e.g., either the stationary controller or the wristband) generates both the alert to the healthcare provider to perform the hand hygiene and/or PPE movements, and the alert to the healthcare provider as to whether the hand hygiene and/or PPE movements were sufficient and/or insufficient.

Generally speaking, the analytics may determine any one, any combination, or all of: compliance; partial compliance; or non-compliance. Further, the analytics may determine any one, any combination or all of: whether the user took hand cleaning agent and/or whether the user took the PPE garment(s); whether the user performed hand movements indicative of hand hygiene and/or whether the user performed hand movements indicative of putting on and/or taking off PPE garment(s); whether the user performed hand movements indicative of hand hygiene and/or PPE for at least a predetermined amount of time; whether the user performed a series of hand movements indicative of hand hygiene and/or PPE; whether the user performed a series of hand movements indicative of hand hygiene and/or PPE each for a respective period of time; and whether the data was indeterminate of compliance.

Responsive to the determination of the analytics, one or more outputs may be generated using output functionality. In one implementation, the wristband may generate one or more outputs based on a determination of any one, any combination, or all of: compliance, partial compliance and/or non-compliance. The one or more outputs from the wristband may comprise audio and/or visual outputs, such as sound(s) (such as different sounds), light(s) (such as different lights or different combinations of lights), vibration(s) (such as different patterns of vibrations), or the like. For example, a first sound may be indicative of compliance and a second sound, different from the first sound, may be indicative of non-compliance. As another example, a first sound may be indicative of compliance, a second sound may be indicative of partial compliance, and a third sound may be indicative of non-compliance. As still another example, a first light may be indicative of compliance (e.g., a green colored light) and a second sound (e.g., a red colored light) may be indicative of non-compliance. As yet still another example, the wristband may escalate the outputs based on a determination of partial compliance and/or non-compliance. In particular, the wristband may initially output a sound and/or light responsive to determining a hand hygiene action and/or PPE action. Responsive to determining non-compliance (and/or partial compliance) with the identified hygiene opportunity and/or the hygiene action (e.g., the hand hygiene action and/or PPE action), the wristband may generate a different type of output, such as a louder sound (e.g., louder than the output responsive to determining a hand hygiene action and/or PPE action) and/or a brighter light (e.g., brighter lights or a greater number of lights than the output responsive to determining a hand hygiene action and/or PPE action).

Alternatively, or in addition, the stationary controller may generate one or more outputs based on a determination of any one, any combination, or all of: compliance, partial compliance and/or non-compliance. The one or more outputs from the stationary controller may comprise audio and/or visual outputs, such as sound(s), light(s), or the like. Alternatively, or in addition, an electronic device separate from the wristband and the stationary controller may generate one or more outputs based on a determination of any one, any combination, or all of: compliance, partial compliance and/or non-compliance. In one implementation, the determination as to compliance, partial compliance and/or non-compliance, either transmitted to or determined by the back-end analytics, may result in the back-end analytics transmitting an alert to a separate electronic device. For example, the separate electronic device (e.g., a smartphone) may be associated with the user who is the subject of the compliant, partial compliant and/or non-compliant hygiene opportunity and/or the hygiene action (e.g., hand hygiene action). As another example, the separate electronic device may be associated with a third party separate from the user subject to the identified hygiene opportunity and/or the hygiene action (e.g., the hand hygiene action and/or PPE action). In particular, the separate electronic device may be associated with an administrator tasked with hand hygiene and/or PPE compliance in a hospital setting or a responsible administrator for a section of the hospital (e.g., the head nurse in the ICU).

Alternatively, or in addition, one or more aspects of the wristband, the stationary controller or the back-end analytics may change responsive to a determination of any one, any combination, or all of: compliance; partial compliance; or non-compliance. As one example, responsive to a determination of partial and/or non-compliance, the wristband and/or stationary controller may modify its operation responsive to a new hand hygiene action and/or PPE action. In one implementation, the outputs generated by the wristband and/or stationary controller may be different than those outputs during a previous wristband event. As one example, the audio outputs generated by the wristband and/or stationary controller may be louder than those outputs during the previous wristband event responsive to determination of partial compliance and/or non-compliance. As another example, an output, not generated during the previous identified hygiene opportunity and/or the previous hygiene action (e.g., the previous hand hygiene action and/or previous PPE action), may be generated in a subsequent identified hygiene opportunity and/or subsequent hygiene action (e.g., subsequent hand hygiene action and/or subsequent PPE action) based on compliance, partial compliance, and/or non-compliance. In particular, responsive to determining that the user partially complied and or non-complied during the previous identified hygiene opportunity and/or the previous hygiene action (e.g., the previous hand hygiene action and/or previous PPE action), a display on the wristband may be activated to output a countdown of 20 seconds. In this way, the user may receive more guidance to wash for a predetermined amount of time (e.g., 20 seconds) responsive to determination of partial or non-compliance. Alternatively, or in addition, the analytics to determine compliance may be different than the analytics used during the previous wristband event and/or previous wristband opportunity. For example, the analytics may be stricter (e.g., requiring a longer time to detect hand hygiene and/or PPE motions for determining compliance) than previously used analytics.

Alternatively, or in addition, the hand hygiene and/or PPE monitoring system may track the dispensing of hand cleaning agent from the dispenser and/or removal of PPE garment (s). In one implementation, the stationary controller tracks at least one aspect related to the dispensing and/or removal. In a more specific implementation, the stationary controller tracks the operation of the dispenser as opposed to hand movement. For example, the stationary controller may include a sensor, such as a sound sensor, to determine whether the dispenser has dispensed the hand cleaning solution. In particular, the sound sensor may record data that the stationary controller may later analyze to determine whether the dispenser has performed an internal movement that is indicative of dispensing hand cleaning solution (e.g., whether the data recorded from the sound sensor is indicative of a motor on the dispenser dispensing hand cleaning agent). For example, the stationary controller may perform frequency domain analysis to determine whether the motor has dispensed hand cleaning solution. One or both of graphs of background sound and dispensing sound may be used by the stationary controller to perform the frequency domain analysis for the determination. Alternatively, the stationary controller may examine output generated by an ultrasonic sensor in order to determine whether hand cleaning solution has been dispensed. In another specific implementation, the stationary controller tracks the operation of the removal of the garment as opposed to hand movement(s). For example, the stationary controller may include a sensor, such as a sound sensor, to determine whether a sound indicates the removal from a container of gowns, masks or the like (and/or the throwing away in the instance of removal the PPE garment(s)). Alternatively, a sensor may indicate whether there is movement near the container to indicate the removal of the PPE garment (e.g., a sensor may indicate that a drawer housing the PPE garment has been opened).

Alternatively, the wristband, via a microphone resident on the wristband, may input sound data and may determine itself whether the sound data is indicative of the sound of the motor dispensing hand cleaning agent and/or removal of the PPE garment from the container.

In still another implementation, the system may include a backend electronic device, such as a server, that performs analytics, as discussed above. The analytics may be configured to perform any one, any combination, or all of: determine compliance (e.g., full, partial or non-compliance); generate compliance reports, to identify trends based on time of shift, protocols, and other desired metrics; identify patients and/or healthcare providers that are the source of cross-contamination; generate alerts responsive to compliance determinations, identifying trends, identifying patients and/or healthcare providers that are the source of cross-contamination, or the like; generating displays or other types of graphical users interfaces to output statistics based on one or more criteria, such as based on an event (e.g., full, partial, or non-compliance), based on people (e.g., analysis based on all doctors, all nurses, or individuals), and/or based on location (e.g., based on the particular floor of a hospital, the particular wing of a hospital, based on a department of the hospital (e.g., ICU-A, ICU-B, ICU-C)).

In another implementation, the stationary controller receives the sensor data from the wristband and analyzes the sensor data, thereby making the determination as to sufficiency and/or insufficiency of PPE movements. Thereafter, the stationary controller transmits the determination (e.g., sufficiency and/or insufficiency of PPE movements according to the guidelines) to an external device, such as the wristband (for outputting an indication of sufficiency and/or insufficiency according to the guidelines) or the back-end analytics.

Alternatively, or in addition, the stationary controller (or alternatively multiple stationary controllers) may determine compliance with multiple protocols, such as both HH protocols and PPE protocols. The determination as to compliance with HH protocols may be achieved in one of several ways, including any one, any combination, or all of: whether hand cleaning agent (such as sanitizer, soap, or the like) has been dispensed; whether the hand movements were for a sufficient period of time; or whether the hand movements were sufficient to meet compliance. Alternatively, or in addition, the determination as to compliance with PPE protocols may occur independently of (or in dependence of) the determination of compliance with the hand hygiene opportunity and/or the hand hygiene action. As one example, the identification of the hand hygiene opportunity is independent of the identification of the PPE opportunity. As another example, the identification of the hand hygiene opportunity is dependent of the identification of the PPE opportunity (identification of one results in identification of the other). As still another example, the determination as to the hand hygiene action is independent of the determination of compliance of the PPE action. As another example, the determination as to the hand hygiene action is dependent of the determination of compliance of the PPE action (e.g., before entering the room, compliance with the hand hygiene action is first determined and thereafter compliance with the PPE action is determined; upon exiting the room, compliance with the PPE action is first determined and thereafter compliance with the hand hygiene action is determined). In still another implementation, the back-end analytics receives the sensor data from the wristband and analyzes the sensor data, thereby making the determination as to sufficiency and/or insufficiency of PPE and/or HH movements according to the guidelines. Thereafter, the back-end analytics transmits the determination (e.g., sufficiency and/or insufficiency of PPE and/or HH movements) to an external device, such as the wristband (for outputting an indication of sufficiency and/or insufficiency) or the stationary controller.

For example, a single stationary controller may be used to determine whether the person is entering or exiting the patient area (e.g., the single stationary controller may be the same stationary controller used for identifying the HH opportunity and/or HH action; alternatively, a different stationary controller may be used for identifying the HH opportunity and/or HH action). In one implementation, the stationary controller may make this determination based on timing and/or based on an identification of the person. As one example, the wristband may include a particular identification associated with the healthcare worker. A particular stationary controller, communicating with the wristband, may receive the particular identification. Responsive to the particular stationary controller determining that it has not communicated with the wristband with this particular identification within a certain period of time (e.g., 2 minutes, 5 minutes, etc.), the stationary controller may determine that the healthcare worker has entered the patient area. Responsive to the particular stationary controller determining that it has communicated with the wristband with this particular identification within the certain period of time, the stationary controller may determine that the healthcare worker is exiting the patient area.

As another example, multiple stationary controllers may be used to determine whether the person is entering or exiting the patient area. The multiple stationary controllers may be stationed in different positions relative to the patient area (e.g., a first stationary controller positioned outside of the patient area and a second stationary controller positioned inside of the patient area). In one implementation, the stationary controllers may interact with a wristband (such as via Bluetooth communication, such as Bluetooth Low Energy (BLE)). Responsive to the interaction, the respective stationary controller may determine whether the healthcare worker (who is wearing the wristband) is entering or exiting the patient area. For example, responsive to the first stationary controller communicating via Bluetooth with the wristband for a certain period or time (or the first stationary controller communicating via Bluetooth with the wristband without the second stationary controller communicating via Bluetooth with the wristband; or the first stationary controller first communicating via Bluetooth with the wristband before the second stationary controller communicates via Bluetooth with the wristband), the first stationary controller (which is positioned outside the patient area) may determine that the healthcare worker is entering the patient area. As another example, responsive to the second stationary controller communicating via Bluetooth with the wristband for a certain period or time (or the second stationary controller communicating via Bluetooth with the wristband without the first stationary controller communicating via Bluetooth with the wristband; or the second stationary controller first communicating via Bluetooth with the wristband before the first stationary controller communicates via Bluetooth with the wristband), the second stationary controller (which is positioned inside the patient area) may determine that the healthcare worker is exiting the patient area.

In another implementation, the wristband may perform the determination as to whether the person is entering or exiting the patient area. In a first specific implementation, the wristband may analyze the sensor data (e.g., data from the gyroscope and/or accelerometer) responsive to detecting communication from a stationary controller. For example, responsive to communicating via Bluetooth with a stationary controller, the wristband may store sensor data from one or more sensors (e.g., gyroscope and/or accelerometer) and analyze the sensor data in order to determine whether the sensor data is indicative of a pulling motion or a pushing motion. Responsive to determining that the sensor data is indicative of a pulling motion and responsive to a pulling motion being indicative of entering an area (e.g., the wristband is pre-programmed to indicate that pulling motions are indicative of entering an area), the wristband and/or stationary controller may determine that the healthcare worker has entered the patient area. Responsive to determining that the sensor data is indicative of a pushing motion and responsive to a pushing motion being indicative of exiting an area (e.g., the wristband is pre-programmed to indicate that pushing motions are indicative of exiting an area), the wristband and/or stationary controller may determine that the healthcare worker has exited the patient area. In a second specific implementation, the wristband may analyze the sensor data (e.g., data from the gyroscope and/or accelerometer) continuously to determine whether a pulling motion or a pushing motion has occurred.

As discussed above, the WHO may issue guidelines regarding hygiene. As one example, the WHO lists five moments of hand hygiene (HH) that define five opportunities where hand hygiene should be followed. The five moments of HH opportunity include: (1) before touching a patient; (2) before clean/aseptic procedures; (3) after body fluid exposure/risk; (4) after touching a patient; and (5) after touching patient surroundings. In this way, the different moments of HH opportunity represent different situations in which to check for HH compliance. Further, as discussed above, a hand hygiene action may be identified or detected based on one or more steps in order to perform hand hygiene compliance (e.g., an event triggered by the dispensing of hand cleaning agent (e.g., hand sanitizer or soap)). Likewise, there may be instances of PPE opportunity and instances of a PPE action (which may be associated with and triggered by a HH action and/or may be triggered by a separate event, such as opening a drawer or a cabinet).

In one or some embodiments, the system may be opportunity-dependent, such as dependent on hygiene opportunity, such as a patient area hygiene opportunity (e.g., the patient area hygiene opportunity indicative of interaction with a patient in the patient area, such as a HH opportunity associated with a patient area and/or a PPE opportunity associated with the patient area), in order to determining any one, any combination, or all of: monitoring compliance; determining whether and/or how to output reminders; staff locating; or patient care billing (e.g., physician billing).

With regard to an opportunity-dependent compliance system, various types of analysis may be dependent on identifying or predicting the hygiene opportunity, such as the patient area hygiene opportunity, such as any one, any combination, or all of: the HH opportunity; the PPE opportunity, or the HH/PPE opportunity. Any discussion herein regarding a hygiene opportunity may include any one, any combination, or all of: a hand hygiene opportunity (e.g., a service industry hygiene opportunity (such as in a restaurant), a medical hygiene opportunity, etc.); a PPE opportunity; or a hand hygiene/PPE opportunity. In one or some embodiments, compliance with the hygiene opportunity, such as the patient area hygiene opportunity (such as the HH and/or PPE opportunity) may comprise: (i) identifying or predicting the hygiene opportunity; and (ii) determining compliance with the hygiene opportunity. In this regard, identifying or predicting the hygiene opportunity may be considered identifying or predicting an opportunity for a moment or interaction with someone (such as interaction with a patient, a patron (such as a restaurant patron), or the like) and/or with something that necessitates compliance with hygiene protocol(s).

As discussed in more detail below, the hygiene opportunity may be identified or predicted in one of several ways, such as based on tracking movement of a person (such as a restaurant worker, a healthcare provider) and/or based on determining interaction with a patient/patron and/or based on certain action(s) performed (e.g., taking hand cleaning agent) (e.g., prediction of the hygiene opportunity may be based on one or both of confirming location in an area (such as inside the patient area) and/or taking hand sanitizer from a dispenser inside the patient area). In one or some embodiments, determining compliance with the opportunity may comprise determining whether a compliant event is sufficiently related to the identified patient area hygiene opportunity. In one or some embodiments, compliance with the hygiene opportunity is the same for different areas (such as different patient areas, different restaurant areas, etc.). In this regard, the same hygiene protocol(s) may be used responsive to identifying the hygiene opportunity (with one or more hygiene actions being detected to determine compliance with the same hygiene protocol(s)). Alternatively, for different areas with different compliance requirements, responsive to identifying or predicting the area hygiene opportunity, the respective protocols for the different areas (e.g., patient area hygiene protocol(s) such as one or both of HH protocol and/or PPE protocol for the specific patient area; different hygiene protocols for different areas of a restaurant, such as a first protocol for a kitchen versus a second protocol for patron area) may be identified, and compliance with the hygiene protocol(s) may be determined in order to determine compliance with the patient area hygiene opportunity (with one or more hygiene actions being detected to determine compliance with the patient area hygiene protocol(s)). As discussed here, the area hygiene protocol(s), which may be specific to the patient area, may be determined in one of several ways (e.g., at the server level; at the patient area level; or at the server level and the patient area level) and with one or more devices (e.g., by any one, any combination, or all of: the server; the stationary controller; or the mobile electronic device).

Thus, in one or some embodiments, determining compliance with the hygiene opportunity (such as the patient area hygiene opportunity) may be dependent on: (a) detecting action(s) (with the action(s) being at least one step to comply with the protocol(s) associated with the area, such as detecting one or more HH action(s); one or more PPE action(s); or a HH/PPE action); (b) determining whether there is a detected event sufficiently related to the identified hygiene opportunity (e.g., determining whether the detected HH action is sufficiently close to one or more criteria, such as time and/or space, to be related to the identified or predicted patient area hygiene opportunity); and (c) responsive to determining whether there is a detected event sufficiently related to the identified hygiene opportunity, assigning or associating the compliance determination with the detected action (or lack thereof) to the identified hygiene opportunity (e.g., if within the criterion, the action(s) are attributed, for purposes of compliance, with the opportunity in order to determine whether there is compliance or non-compliance with the identified hygiene opportunity). Alternatively, or in addition, the system may further predict which, of a plurality of potential people, performed the action(s), as discussed further below.

Thus, in one or some embodiments, a method and system are disclosed that determine whether a provider (such as a healthcare provider) is complying with defined protocols, such as compliance with any one, any combination, or all of a plurality of HH opportunities (such as the WHO five moments of hand hygiene opportunity). Alternatively, a method and system are disclosed that determine whether a provider is complying with defined healthcare protocols, such as compliance with any one, any combination, or all of a plurality of PPE opportunities. Still alternatively, a method and system are disclosed that determine whether a provider is complying with defined healthcare protocols, such as compliance with any one, any combination, or all of a plurality of HH opportunities and a plurality of PPE opportunities.

In particular, a system and a computer-implemented method is disclosed for determining compliance by a person with one or both of a HH opportunity or a PPE opportunity, including: determining whether there is one or both of a HH action or a PPE action that is sufficiently associated in time or in space with the one or both of the HH opportunity or the PPE opportunity; responsive to determining that there is the one or both of the HH action or the PPE action that is sufficiently associated in time or in space with the one or both of the HH opportunity or the PPE opportunity: determining compliance with the one or both of the HH action or the PPE action; and attributing the determined compliance with the one or both of the HH action or the PPE action to the one or both of the HH opportunity or the PPE opportunity (e.g., due to sufficient closeness in time and/or space, the action(s) are attributed identified opportunity in order to determine whether there is compliance or non-compliance for the identified opportunity); and responsive to determining that there is no HH action or PPE action that is sufficiently associated in time or in space with the identified one or both of the HH opportunity or the PPE opportunity, determining non-compliance for the one or both of the HH opportunity or the PPE opportunity. Further, identifying the one or both of the HH opportunity or the PPE opportunity may occur either prior to or after detecting the one or both of the HH action or the PPE action. In addition, whether the one or both of the HH action or the PPE action is sufficiently associated in time may comprise whether an act associated with the HH action (e.g., the dispensing of hand cleaning agent or the completion of hand movements, which may comprise the trigger to detect the HH action) or the PPE action (e.g., the taking of PPE or the completion of the PPE movements, which may comprise the trigger to detect the PPE action) is within a time period of the one or both of the HHE opportunity or the PPE opportunity.

Thus, in one or some embodiments, the method and system include identifying one or more HH opportunities, and determining compliance with the identified one or more HH opportunities. As discussed in more detail below, identifying a HH opportunity may be determined in one of several ways. In one way, identifying movement of a healthcare provider relative to an area, such as relative to a patient area (such as into a patient area, out of a patient area, within a patient area, etc.), may be used to identify or predict the HH opportunity. As one example, to identify moment (1), which is before touching a patient, the healthcare provider's movement may be tracked into a patient area, such as any one, any combination, or all of: tracking movement toward a defined border of a patient area; tracking movement crossing the border of the patient area; or tracking movement within the patient area after crossing the border of the patient area. As another example, in order to identify moments (4) and (5), which is after touching a patient and after touching patient surroundings, respectively, the healthcare provider's movement may be tracked out of a patient area, such as any one, any combination, or all of: tracking movement toward a defined border of a patient area; tracking movement crossing the border of the patient area; tracking movement outside the patient area after crossing the border of the patient area.

Further, tracking the healthcare provider's movement may be performed in one of several ways. In one way, external sensors (e.g., sensors that are not associated with the healthcare provider, such as not resident on the wristband associated with the healthcare provider) may be used to determine movement of the healthcare provider into and/or out of the patient area. For example, one or more ultrasonic sensors, statically positioned in different parts of the patient area (e.g., at an entrance to the patient area and/or in one or more sections in an interior of the patient area) may be used to track whether the healthcare provider is moving into or out of the patient area. In another way, a mobile electronic device (such as a wristband) associated with or attached to the healthcare provider may be used to determine movement into, inside and/or out of the patient area. For example, the mobile electronic device may communicate with one or more electronic devices associated with the patient area, such as one or more stationary controllers positioned external, at a border and/or interior to the patient area. The mobile electronic device, using communications with the one or more stationary controllers, may determine whether the electronic device (and in turn the healthcare provider wearing the electronic device) is moving toward or away from the patient area. In this regard, the tracking may be performed either external to a wristband (or other mobile electronic device) associated with the healthcare provider and/or may be performed by the wristband (or other mobile device) associated with the healthcare provider.

Thus, in one or some embodiments, the hygiene opportunity may be identified or predicted (without further confirmation). Merely by way of example, a provider's movements may be tracked in order to identify or predict the hygiene opportunity. Alternatively, the hygiene opportunity may be identified or predicted, and thereafter confirmed. In particular, in one or some embodiments, the hygiene opportunity may initially be identified or predicted based on a first set of inputs (such as by tracking the provider's movements) and thereafter confirmed based on a second set of inputs. The second set of inputs may include any one, any combination, or all of: sensor input (e.g., sensors positioned with an area to track the provider); communication zone identification (e.g., a communication zone within the area); or action(s) (e.g., actions, such as taking sanitizer, associated with the area). In one or some embodiments, the first set of inputs for the initial prediction may be generated by one of electronic device(s) associated with the provider or electronic device(s) not associated with the provider (such as associated with the area) and the second set of inputs for the confirmation may be generated by the other of electronic device(s) associated with the provider or electronic device(s) not associated with the provider. For example, the initial prediction may be based on data generated by the wristband associated with the provider and the confirmation may not be associated with the provider but be associated with the area to indicate that an action has been performed in the area or a presence is in the area, such as any one, any combination, or all of: (i) sensors associated with the area (such as ultrasonic or infrared sensors (providing tracking data if the provider crossed a threshold within the area); (ii) communication zones in the area (e.g., BLE identifying the wristband within a specific proximity zone identified within the area); or (iii) actions associated with the area (e.g., taking sanitizer from a dispenser within the area). By way of example, with regard to (ii), the area may include one or more communication zones with confirmation of the predicted opportunity being based on the wristband being within one or more of the communication zones (see FIGS. 8A-C). Further, in one embodiment, identification of at least two of (i), (ii), or (iii) result in a determination that a person (associated with the wristband) is within the area.

Associated with identifying a HH opportunity is determining compliance with the HH opportunity. As discussed in more detail below, compliance may comprise compliance with the HH action (e.g., determining whether hand cleaning agent has been dispensed and/or the required duration of movements and/or specific movements are performed). However, the events or actions to determine compliance with the HH opportunity (e.g., compliance with the hand hygiene action) may start before or after identifying the respective HH opportunity, thereby complicating matters. This is due to hand cleaning agent dispensers potentially being located outside and/or inside a patient area (e.g., at the entrance to a patient room and inside the patient room).

As one example, a healthcare provider may walk into the patient room (which may be indicative of HH opportunity moment (1), discussed above) and thereafter take hand sanitizer (or some other hand cleaning agent) from a dispenser positioned within the patient room. In such an example, the identification or prediction of the HH opportunity (e.g., due to tracking the healthcare provider) may occur before detecting the HH action (e.g., due to detecting dispensing of hand cleaning agent from a dispenser located within the patient room). As another example, the healthcare provider may take hand sanitizer (or some other hand cleaning agent) outside of the patient room, thereby triggering the HH action, in a hallway external to a patient's room before the HH opportunity is identified. In such an instance, the healthcare provider may either enter the patient's room or may continue to walk down the hallway. The former case (the healthcare provider entering the patient's room), in certain circumstances, may be a HH opportunity (e.g., moment (1)). In a first instance, the healthcare provider may immediately (or within a certain time period) enter the patient's room, thereby sufficiently connecting the HH action with the HH opportunity. In a second instance, the healthcare provider may wait an excessive amount (e.g., greater than the certain time period) to enter the patient's room, thereby decoupling the HH action from the HH opportunity and rendering any determination of compliance with the HH action as not being applicable to the identified HH opportunity (e.g., due to the elapsed time between the HH action and the HH opportunity, there is an increased likelihood that the healthcare provider has interacted with someone or something else prior to entering or exiting the patient area, thereby rendering compliance with the decoupled HH action as not being applicable to the HH opportunity). Though, the healthcare provider may have already taken sanitizer and began rubbing hands before the healthcare provider's movement into the patient room is detected (and thus before the HH opportunity is identified). As another example, the healthcare provider's taking of sanitizer from a dispenser inside the patient room and subsequently waiting an excessive amount before leaving the room may likewise decouple any HH action compliance determination with the HH opportunity of moments (4) and (5).

The latter case (the healthcare provider takes hand cleaning agent outside of the patient's room and continues to walk down the hallway) again may or may not be a HH opportunity depending on what occurs thereafter. In particular, if the healthcare provider takes the sanitizer and continues to walk down the hallway rubbing hands, but does not perform any action that indicates a HH opportunity within a certain period of time (e.g., the healthcare provider does not walk into a patient's room within 10 seconds), the determination of HH compliance (e.g., determination of compliance with the HH action) may be considered in certain embodiments to be too remote to be associated with any HH opportunity.

Various criteria may be used to determine closeness and/or remoteness of the HH opportunity with the HH action. Criteria include, for example, time and/or distance. As discussed below, the criteria of time may be static (e.g., a predetermined time period between one aspect of the HH action and one aspect of the HH opportunity) and/or may be dynamic (e.g., based on any one, any combination, or all of: the protocol(s) to be followed; positioning of dispensers; or the behavior of the healthcare provider). The HH opportunity may have an identified start time (e.g., identified based on tracking the movement of the healthcare provider) and/or an identified end time. Likewise, the HH action may have an identified start time (e.g., identified based on the HH predicate act of dispensing of hand cleaning agent) and/or an identified end time (e.g., based on completion of compliance with the HH action). Thus, the criteria (e.g., time) may be measured between one aspect of the HH action (such as the beginning of the HH action and/or the completion of the HH action) with one aspect of the HH opportunity (such as the identified start and/or end of the HH opportunity).

Thus, in one or some embodiments, responsive to the timing of one aspect of the HH action being within the timing of one aspect of the HH opportunity, the determination regarding compliance (e.g., compliant, non-compliant, partially compliant) with the HH action may be ascribed to the HH opportunity. In an example where detecting the dispensing of hand cleaning agent is indicative of the HH action, a dispensing time at which the hand cleaning agent is dispensed from the dispenser is determined, and may be either before or after identifying the HH opportunity. If the dispensing time is within a first period of time before identifying the HH opportunity or is within a second period of time after identifying the HH opportunity, the HH action is sufficiently tied in time to the HH opportunity. Otherwise, if the dispensing time is not within a first period of time before identifying the HH opportunity or is not within a second period of time after identifying the HH opportunity, the HH action is not sufficiently tied in time to the HH opportunity. In one embodiment, the first time period is different from the second time period, as discussed below. Alternatively, the first time period is the same as the second time period.

In one or some embodiments, the timing may be static and predetermined (e.g., 8 seconds after identifying the HH opportunity until detecting the HH action or 10 seconds after detecting the HH action until identifying the HH opportunity, as discussed further below). Alternatively, the timing may be dynamic based on any one, any combination, or all of: the protocol(s) to be followed (e.g., healthcare provider is required to follow HH protocol versus PPE protocol (with less time given between the aspect of the HH action and the aspect of the HH opportunity as opposed to more time given between the aspect of the PPE action and the aspect of the PPE opportunity since complying with the HH protocol is quicker); healthcare provider is required to follow only one protocol versus two protocols (with less time given between the aspect of the HH action and the aspect of the HH opportunity as opposed to more time given between the aspect of the HH/PPE action and the aspect of the HH/PPE opportunity since complying with two protocols such as HH and PPE, takes longer); the behavior of the healthcare provider (e.g., the backend server may analyze the behavior of a specific healthcare provider in order to determine the typical time the specific healthcare provider takes between an event (such as a HH and/or PPE action) and an opportunity (e.g., between the HH action and the HH opportunity); or the positioning of hardware (e.g., the position of dispensers in a healthcare setting (with more time given for dispensers placed further from the entrance of a patient area).

For example, a specific HH action may be identified when sanitizer dispensing is detected; even if the duration and/or movements render the specific HH action "compliant" for purposes of the hygiene protocol, that compliance is not associated with any specific HH opportunity if the compliant HH action is too remote in time (there has been too much time elapsed that can lead to subsequent hand contamination of the healthcare provider, between the triggering of the specific HH action and/or the completion of the duration and/or movements of the specific HH action to an identified HH opportunity). As such, any compliance determination with the HH action may be deemed too remote (such as too remote in time and/or too remote in distance) as to render the HH opportunity compliant as well. In this regard, there are instances where a HH action is not tied at all or not sufficiently tied to a HH opportunity.

By way of example, a configuration with a hand cleaning agent dispenser at the entrance to the room and in the interior of the room is considered. In particular, when entering, the healthcare provider may first take hand cleaning agent from the dispenser at the entrance, and then walk into the room. In this instance, the HH action is detected (e.g., by detecting the dispensing event) prior to identifying the HH opportunity (e.g., by tracking the movement into the patient room). In another instance when entering, the healthcare provider may first walk into the room (triggering identification of the HH opportunity) and then take hand cleaning agent from the dispenser in the interior of the patient room (triggering detection of the HH action). Similarly, when exiting, the healthcare provider may take hand cleaning agent from the dispenser in the interior of the patient room (triggering detection of the HH action) prior to leaving the patient room (which may trigger identification of the HH opportunity). Conversely, when exiting, the healthcare provider may first leave the patient room (triggering identification of the HH opportunity) and then take hand cleaning agent from the dispenser at the entrance of the patient room (triggering detection of the HH action). Thus, the HH action may begin before or after identifying the HH opportunity. Further, responsive to determining that the HH action and the HH opportunity are sufficiently close to one another (e.g., sufficiently close in time and/or in space), the determination of compliance of the HH action is imputed or associated with the identified HH opportunity. For example, closeness in time may be determined whether the HH action is detected before or after identifying the hand hygiene opportunity (e.g., the HH opportunity is identified within X seconds of detecting the HH action; the HH action is detected within Y seconds of identifying the HH opportunity, with X=Y in one embodiment and different in another embodiment). In this way, determining compliance with the HH opportunity may be based on both: (i) determining whether there is a sufficient connection of the identified HH opportunity with a specific HH action(s); and (ii) determining compliance with the specific HH action(s). This is in contrast to merely focusing on compliance with HH action completely divorced from any identified HH opportunity.

In one or some embodiments, the HH opportunity may be accompanied by a PPE opportunity. For example, in certain circumstances, a PPE opportunity may be present when the healthcare provider enters or exits the patient room, as discussed above. In a particular example, when entering the patient area, the PPE is typically outside of the patient area (such as near the entrance to the patient area and near the hand cleaning agent dispenser outside of the patient area). In this regard, the typical protocol prior to entry of the patient area is for the healthcare provider to clean hands first, and then put on PPE. As such, the initial trigger for checking for PPE may be the dispensing of hand cleaning agent (with the HH opportunity confirmed responsive to tracking the movement of the healthcare provider into the patient room within a certain period of time). In one or some embodiments, the PPE opportunity may be tied or connected to the HH opportunity. As one example, prior to entering the patient area, a healthcare provider may first clean hands and then don PPE. As another example, prior to exiting the patient area, a healthcare provider may first doff PPE and then clean hands. Thus, the PPE opportunity may be connected to the HH opportunity.

However, complicating matters is identifying or predicting an actual PPE opportunity from amongst the general behavior of a healthcare provider. As discussed above, a healthcare provider may take sanitizer from the dispenser outside of the patient room, thereby triggering a HH action. Likewise, a healthcare provider may take PPE, such as gloves or a mask, from a cabinet positioned outside of the patient room, thereby potentially triggering a PPE action (discussed below). After taking sanitizer or taking PPE, the healthcare provider may enter the patient room, or may continue to walk down the hallway. In order to better monitor compliance with a PPE opportunity, a trigger for determining a PPE opportunity is disclosed. Various triggers are contemplated. As one example, the trigger to detect a PPE action is the same as for a HH action (e.g., triggering detection or prediction of a PPE action is the same as the trigger to detect or predict a HH action, such as based on detecting dispensing of hand cleaning agent). Further, the trigger to identify the PPE opportunity is the same as for the trigger to identify the HH opportunity (e.g., a HH opportunity is based on tracking movement of the healthcare provider into and/or out of the patient area).

Alternatively, the trigger for checking for a PPE action may be different than for a HH action. As discussed above, upon entry, the proximity sensing-output generating device may be attached to a cabinet or a door, and may generate data responsive to opening the cabinet or door. Thus, when PPE is housed in a cabinet or in a drawer, the proximity sensing-output generating device may be attached thereto and may generate a sensor output when the cabinet or door is opened, thereby triggering detection of the cabinet/drawer containing PPE opening (thus leading to the conclusion that the healthcare provider is donning PPE prior to entering the patient area (e.g., the proximity sensing-output generating device, either directly or via the stationary controller, sends a communication to the wristband to monitor PPE movements). Further, upon exit, the trigger for monitoring a PPE action may comprise movement, such as moving past a beam, as discussed below.

As one example, when entering a patient room, the trigger for the HH action may comprise the taking of hand cleaning agent (e.g., the stationary controller may determine that hand cleaning agent was dispensed, and then send a message to the wristband(s) in the dispensing messaging zone to monitor hand movements associated with hand hygiene) whereas the trigger for the PPE action may comprise the taking of PPE (e.g., the proximity sensing-output generating device, discussed herein, may be attached to a cabinet or a door housing PPE, and may generate data responsive to opening the cabinet or door; responsive to generating the data from the proximity sensing-output generating device, a message, routed directly or via a stationary controller, may be sent to the wristband to monitor hand movements associated with PPE). As another example, when exiting a patient room, the trigger for the PPE action may comprise movement toward the exit (such as breaking an ultrasonic beam, discussed below) whereas the trigger for the HH action may comprise the taking of hand cleaning agent.

Alternatively, or in addition to opportunity-based monitoring, generating reminders for persons, such as the healthcare provider, visitors, patients, or the like, may be opportunity-based. Thus, in one or some embodiments, separate from, or in addition to, monitoring compliance with a hygiene opportunity (such as a HH opportunity and/or a PPE opportunity), a healthcare provider or a service provider is provided reminder(s) as to the protocol(s) to comply with the hygiene opportunity. For example, reminders may be generated for healthcare workers or service providers according to any one, any combination, or all of the following: responsive to identifying a hygiene opportunity (e.g., responsive to identifying a HH opportunity and/or a PPE opportunity); responsive to detecting a hygiene action (e.g., responsive to detecting a HH action and/or a PPE action); responsive to identifying both a hygiene opportunity and a hygiene action; responsive to detecting a hygiene opportunity and responsive to a determination of compliance or non-compliance with the hygiene opportunity; or responsive to detecting a hygiene action and responsive to a determination of compliance or non-compliance with the hygiene action.

As discussed above, there are various contexts in which people may be reminded of protocols, such as HH and/or PPE protocols. In one or some embodiments, the reminders associated with a patient area may be responsive to and dependent on one or both of identifying the area hygiene action, such as the patient area hygiene action (e.g., the patient area hygiene action follows one or both of a HH protocol for a HH action or a PPE protocol for a PPE action) or on identifying the area hygiene opportunity, such as the patient area hygiene opportunity (e.g., the HH opportunity and/or the PPE opportunity). Responsive to identifying one or both of the area hygiene action or the area hygiene opportunity, area protocol(s) (such as one or both of patient area PPE protocol or patient area HH protocol) are determined and an output for the area protocol(s) are generated. As discussed above, identifying the area hygiene opportunity may be performed in one of several ways, such as by tracking the movement of a person, such as a healthcare provider or a service provider. Further, the hygiene action may be determined based on detecting at least one action of the provider (e.g., taking sanitizer from a dispenser; taking PPE from a cabinet/drawer or other type of PPE dispenser; throwing away PPE into a trash can; interaction of a mobile electronic device (such as a wristband) with a stationary controller). In this way, by making the reminders opportunity-based (e.g., determining whether to generate a reminder based on an identified or predicted opportunity), the reminders may be generated in a more intelligent manner.

Further, reminders may be generated at any stage of determination of compliance (or lack thereof), thereby providing feedback to the healthcare provider as to the adequacy (or inadequacy) of compliance. For example, responsive to detecting an error in compliance (such as for hand hygiene any one, any combination, or all of: failing to take hand cleaning agent; failing to rub a sufficiently long time; or failing to perform the proper requisite movements), an output may be generated indicating the deficiency. Alternatively, responsive to detecting compliance with the hygiene protocol (such as for hand hygiene any one, any combination, or all of: taking hand cleaning agent; rubbing a sufficiently long time; or performing the proper requisite movements), an output may be generated indicating compliance.

As discussed above, the hygiene opportunity may be identified or predicted (e.g., based on identifying one or more moments or interactions with somebody or something). Alternatively, or in addition, one or more electronic devices may predict who, of a plurality of potential people, performed the hygiene action. The prediction may be based on any combination of data generated before performing the action (e.g., data indicative of approaching the dispenser including tracking data and or signal strength data), data contemporaneously with performing the action (e.g., analyzing hand movement data to determine whether palm is turned upward and/or analyzing signal strength), or after performing the hygiene action (e.g., analyzing hand movement data and/or analyzing signal strength). As discussed above, various hygiene actions may be detected, such as taking hand cleaning agent, taking PPE, or the like. In certain instances, there may be more than one person who potentially performed the hygiene action (e.g., where there are two workers in an area, such as a patient area). In other instances, there may be a single person who performed both actions (e.g., a single provider took two dispenses of hand cleaning agent in a row). In either instances, the system may predict which person performed the hygiene action. As discussed above, there may be a single device that performs the various actions, such as the wristband (e.g., the wristband predicts or identifies the hygiene opportunity; the wristband also predicts who performed the hygiene action(s)). Alternatively, multiple devices perform various actions, such as a mobile wristband and a stationary controller. In such an instance, any combination of the multiple devices may perform the determinations: (i) identifying or predicting the hygiene opportunity; (ii) detecting the hygiene action(s); (iii) predicting who performed the hygiene action(s); or (iv) determining compliance for the hygiene opportunity. In one example, compliance with a hygiene protocol necessitates taking hand cleaning agent. In this example, (i), (ii), (iii), or (iv) may be performed by one or both of the mobile wristband or the stationary controller. In this regard, each combination of which the mobile wristband or the stationary controller perform (i), (ii), (iii), and (iv) are contemplated. In a specific example, (i) may be performed by the mobile wristband (e.g., tracking the user to identify or predict the hygiene opportunity) and (ii) may be performed by the stationary controller (e.g., detecting whether hand cleaning agent was dispensed). (iii) may be performed by either the stationary controller (in what is considered a stationary controller-centric prediction) or the mobile wristband (in what is considered a wristband-centric prediction). Further, (iii) may be determined based on any combination of data taken before, during, or after the hygiene action is performed, as discussed above. (iv) may be performed by the stationary controller (e.g., the stationary controller detects dispensing of hand cleaning agent) and/or by the wristband (e.g., the wristband detects movements), depending on the requirements for compliance with the hygiene protocol.

In a stationary controller-centric prediction of which person performed the action(s) (such as taking hand cleaning agent from the dispenser that the stationary controller is associated with), the stationary controller may determine at least one aspect (such as closeness) of the mobile wristband(s) in order to predict which wristband (and in turn which person) performed the action. Merely by way of example, the stationary controller may communicate with one or more wristbands, and analyze the communication, such as the strength of the signal (e.g., the RSSI signal) in order to determine which signal is strongest (e.g., the highest RSSI signal). In turn, the specific wristband with the strongest signal is predicted to be closest to the stationary controller and therefore most likely to have performed the action. In response to the prediction, the stationary controller may send a communication to the specific wristband (e.g., addressed only to the specific wristband) indicating that the specific wristband is to monitor hand movement to determine compliance. In one embodiment, the stationary controller may analyze the strength of the signal and only send one communication (such as immediately responsive to the stationary controller detecting the dispensing of hand cleaning agent, the stationary controller may determine the strongest RSSI signal and send only one communication to the determined wristband with the strongest RSSI signal). Alternatively, the stationary controller may analyze RSSI signals periodically, such as in two or three intervals (e.g., 500 mSec intervals) after detecting the dispense, determine the strongest RSSI signal at each interval, and send communications based on the determination. Various ways for the stationary controller to communicate with the wristbands are contemplated. By way of example, the stationary controller's communications with individual wristbands may be based on establishing separate communication channels.

As one example, if wristband X is determined to have the strongest RSSI at both interval 1 and interval 2, the stationary controller may send a single communication to wristband X for wristband X to monitor movement. As another example, if wristband X is determined to have the strongest RSSI at both interval 1 and if wristband Y is determined to have the strongest RSSI at interval 2, the stationary controller may send a first communication to wristband X for wristband X to monitor movement and thereafter send a first communication to wristband Y for wristband Y to monitor movement. In response to receiving the communications, wristbands X and Y may monitor movement. In one embodiment, responsive to receiving the communication, the respective wristband may check whether there is movement detected (e.g., the movement data generated by motion sensors resident on the respective wristband indicate movement). In response to detecting movement, the respective wristband may continue its analysis (e.g., determine whether the movement is sufficient for compliance). In response to not detecting movement, the respective wristband may ignore the communication from the stationary controller, in effect determining that the respective wristband did not perform the action of taking hand cleaning agent.

In a wristband-centric prediction of which person performed the action(s), the respective wristband may determine at least one aspect in order to predict whether the respective wristband (and in turn the person associated with the respective wristband) performed the action. As discussed above, the stationary controller may detect an action, such as detecting dispensing of hand cleaning agent. In turn, the stationary controller may send a broadcast communication so that any wristband within range of the stationary controller may receive the broadcast communication. In turn, a respective wristband within the communication range may perform its own analysis to determine whether the person associated with the respective wristband performed the action. In one embodiment, the respective wristband may check whether there is movement detected. In response to detecting movement, the respective wristband may continue its analysis. In response to not detecting movement, the respective wristband may ignore the broadcast communication from the stationary controller, in effect determining that the respective wristband did not perform the action of taking hand cleaning agent.

As discussed above, data relating to HH and/or PPE compliance (such as any one, any combination, or all of HH action compliance, HH opportunity compliance, PPE action compliance, or PPE opportunity compliance) may be analyzed in order to perform one or both of: identifying provider(s) who may have contributed to an identified infection; or identifying potential future infection risks. For example, the analytics may determine who are the person(s) that contributed to infections and/or which patients are at risk of infection. Complicating matters is identifying whether the protocols were not followed upon entry of the patient area (thereby potentially resulting in infection of the patient in the patient area) and/or upon exit from an infected patient area (thereby potentially resulting in infection of the patient in a subsequently visited patient area). Thus, backend analytics, such as one or more servers, may be used to perform the data analysis, as discussed above. Various types of analysis are contemplated, including any one, any combination, or all of: infection root cause analysis; cluster root cause analysis; future cluster risk analysis and future infection risk analysis. In this way, one may identify healthcare providers that contribute to infections and/or patients at risk of infections.

In one or some embodiments, the infection analysis may be opportunity focused, such as focused on whether there is full, partial or no compliance with a HH opportunity and/or a PPE opportunity. Underlying the opportunity-focused analysis, pathogens may be transmitted via contact, such as via the WHO opportunities discussed above. In particular, five WHO opportunities are discussed above. In one or some embodiments, some of the opportunities may be identified directly (such as by tracking the movement of the provider into and/or out of a patient area) and other opportunities may be inferred from one or more aspects of the provider (e.g., healthcare provider activity, such as duration with in the patient area and/or status of the healthcare provider).

As discussed in more detail below, various types of infection analysis are contemplated, such as infection root cause analysis, cluster root cause analysis, future cluster risk analysis and future infection risk analysis. One, some or each of those may be opportunity focused in that the underlying infection analysis is based on analyzing compliance with opportunities in order to determine the underlying cause of an infection, determining clusters of infection, or estimating future risk of infections. This information may then be used in order to modify treatment of one or more patients and/or modify hygiene protocol(s) for the one or more patients. This opportunity-focused analysis is in contrast to typical infection analysis, which generally analyzes compliance or non-compliance with hygiene protocols but are not moored or tied to any identified opportunities. In this way, unlike typical infection analysis, the opportunity-focused analysis centers on identified interactions with patients that are identified as important, as opposed to general infection analysis that may include it its analysis irrelevant interactions, thereby resulting in erroneous results.

In this regard, an opportunity-based infection analysis system and method are disclosed, including: at least one memory configured to store hygiene opportunity compliance data, with the hygiene opportunity compliance data indicative of compliance by one or more healthcare providers of identified hygiene opportunities for interacting with a patient, the hygiene opportunities being identified based on tracking movement of the one or more healthcare providers; at least one output device; and at least one processor in communication with the memory and the output device. The processor is configured to: access the hygiene opportunity compliance data; identify some or all of the hygiene opportunity compliance data associated with a patient area during an identified period of time, with the identified hygiene opportunity compliance data being segmented into at least two separate opportunities; identify, based on the hygiene opportunity compliance data associated with the patient area during the identified period of time, the one or more healthcare providers that visited the patient area during the identified period of time; analyze, for the one or more healthcare providers that visited the patient area during the identified period of time, identified hygiene opportunity compliance data separately for the at least two separate opportunities; and generate an output based on the analysis.

For example, wherein the opportunities comprise (1) before touching a patient, (2) before clean/aseptic procedures, (3) after body fluid exposure/risk, (4) after touching a patient, and (5) after touching patient surroundings, (1) may be identified based on tracking the healthcare provider's movement into the patient area, (4) and (5) may be identified based on tracking the healthcare provider's movement into the patient area, and (2) and (3) may be estimated based on the tracking of the healthcare provider's movement. In particular, (2) and (3) may be estimated based on: determining, based on the tracking of the healthcare provider's movement, a duration within the patient area; determining a status of the healthcare provider; and estimating a number of hygiene opportunities based on the duration of the healthcare provider within the patient area and the status of the healthcare provider (e.g., the status of the healthcare provider may comprise a title or role associated with the healthcare provider, such as one of trainee, nurse, doctor, or hospital support staff (such as clinical assistants who take care of ward housekeeping, patient services assistants who bring meals and drinks, porters who take care of patient lifting and transport, volunteers who help with fundraising and ward visits, or ward clerks who staff the ward reception desks); in the example of a nurse, it is estimated that nurses touches a patient once every 5 minutes; so that, if a nurse spends 1 hour in patient room, it is estimated that there were 12 opportunities within the 1 hour spent in the patient room; in the example of a doctor, it is estimated that doctors touch patients more frequently than nurses, though this may depend on healthcare settings so that the healthcare setting may factor into the estimated number of touches in a predetermined time period). Further, based on the number of estimated hygiene opportunities, the system may then estimate a compliance rate for a specific healthcare provider with regard to the number of estimated hygiene opportunities based on historical data (e.g., examining data for a time period, such as the previous week, month, etc. a compliance rate for the specific healthcare provider).

In addition, depending on the type of analysis, different opportunities, such as different HH opportunities, may be analyzed. For example, with regard to infection root cause analysis, opportunities analyzed may, in one embodiment, consist of (1), (2) and (3) in order to perform a root cause analysis for an infection in the patient room. Specifically, the opportunities analyzed may be limited in time, such as during a predetermined number of days after confirming infection in the patient room. Thus, infection root cause analysis may be directed to a single patient area (e.g., the patient's room) where the patient became infected. In this regard, infection root cause analysis may determine, from a statistical standpoint, which healthcare provider(s) contributed to the infection of the patient. Practically speaking, the patient will be in contact with several healthcare providers, some of which result in infection(s). Thus, the patient may accumulate pathogens from one or more of the several healthcare providers. The infection root cause analysis may evaluate the contribution to infection from each opportunity (and from each healthcare provider) over time. In one or some embodiments, the infection root cause analysis may then generate an output to indicate the healthcare provider(s) more likely to have caused the infection, such as generate a ranked list output of healthcare providers based on risk of having caused the infection (e.g., determine which healthcare provider made the greatest contribution to the infection, such as indicate who is the highest risk healthcare provider to cause the infection). In turn, treatment and/or protocol(s) for patient(s) (such as those patients who have had contact with the healthcare providers ranked higher or highest on the ranked list) may be modified accordingly, such as in an anticipatory way in that an infection may be expected for those patient(s).

As another example, cluster root cause analysis may be performed. Typically, analysis only focuses on tracking a high-risk healthcare provider who traveled from room to room. However, cross contamination may occur because of any provider and not simply high-risk healthcare providers. In this regard, an analysis that only examines high risk providers may be wanting. Further, the opportunity-based focus for the analysis (rather than a person-based focus) may examine the opportunities, regardless of compliance rate, for a specific healthcare provider. For example, the specific healthcare provider may have only entered the patient area once (resulting in a healthcare opportunity), with a low compliance rate for that opportunity (e.g., zero compliance), potentially causing contamination. However, a high-risk analysis may discount such a non-compliant opportunity since the specific healthcare provider may have a high overall compliance rate. Thus, instead of focusing on overall compliance rate, focusing on different opportunities (and the associated compliance for those different opportunities) may result in more reliable contamination analysis.

Further, the opportunity-focused analysis may assist in the cross contamination analysis, particularly when opportunities are connected. For example, a healthcare provider may exit a first room (resulting in a first opportunity) and thereafter may enter a second room (resulting in a second opportunity). The healthcare provider's failure to wash hands when exiting the first room (e.g., a non-compliant first opportunity) impacts the connected second opportunity. In this way, the analysis may determine whether separate opportunities (whether those opportunities are from the same healthcare provider or different healthcare providers) are to be coupled, based on any one, any combination, or all of: (1) time (e.g., whether the two opportunities are within a certain time period of one another); (2) space (e.g., whether the two opportunities are within a certain distance from one another); or (3) compliance. For example, with regard to compliance, if a specific healthcare provider fails to comply both with the first opportunity and the second opportunity, the opportunities may be connected; otherwise, if the specific healthcare provider fails to comply with the first opportunity but complies with the second opportunity, the opportunities may be disconnected since the healthcare provider presumably remedied the previous failure with the first opportunity with compliance of the second opportunity. As another example, a first opportunity resulting from a first healthcare provider exiting the first room and thereafter returning to the nurses' station may be connected to a second opportunity from a second healthcare provider going from the nurses' station and entering a second room. More specifically, compliance failure by the first healthcare provider with the first opportunity and compliance failure by the second healthcare provider with the second opportunity may be connected. In the case of future infection risk analysis, opportunities for each room may be connected in order to determine the number and/or types of potential pathogens for each room the patient has been exposed to from the different healthcare providers. As one example, the future infection risk analysis may receive as input one or both of a date range for analysis (such as the past 24 hours, the past week, etc.) or patient area(s) (such as a specific patient room, a specific set of patient rooms, an entire healthcare facility (by default if no patient area input given), etc.). The future infection risk analysis may analyze the compliance data associated with opportunities connected to the patient area(s) in order identify a future risk of infection associated with the patient area(s). In this way, the analysis may connect opportunities (whether with the same healthcare provider or different healthcare providers).

Separate from opportunity-based analysis, the methodology used to identify an opportunity may be applied to different contexts of patient care. As one example, physician monitoring and/or billing may rely on such a methodology. Typically, physicians simply bill each patient based on an estimated time that the physician spends with a patient. As discussed in more detail below, the methodology may identify when the physician enters the patient area and exits the patient area. As such, the methodology may provide the exact visit time and/or the exact duration of the visit.

As another example, the methodology may be used for workload analysis of healthcare workers. In particular, the system may track the duration between entrance/exit opportunities with patients, thereby tallying a total time that a healthcare worker is with patients. Thus, the methodology may generally track how long a first nurse versus a second nurse has spent with patients. Further, the methodology may track any one, any combination, or all of: a total time that any healthcare worker spends with a specific patient; a total time any nurse (or any other type of healthcare worker, such as doctors) spends with a specific patient; or a total time a specific nurse (or other specific healthcare worker, such as a specific doctor) spends with a specific patient. The duration data may be used for human resources purposes and/or for workload analysis. Thus, the analysis may result in modification of workloads so that healthcare works may work more or less based on the analysis.

For example, in order to accurately analyze hygiene data, the system (such as the backend server) may store in a database hygiene records every time a healthcare provider enters and/or exits a room. In particular, the server may store each patient visit and its duration. With each stored entry being designated as a Hygiene action. By iterating through these records sequentially and pairing enter and exit events, the system may calculate how long a provider spent in a given patient room. In one or some embodiments, a user may input the area (e.g., one or a plurality of patient rooms) subject to analysis, as well as a time period (e.g., the last week, the last month, etc.). Thus, the system may any one, any combination, or all of: fetch all Hygiene actions in the input time period for the given area; record the Hygiene actions by staff member and room (e.g., "How long did each staff member spend in each room?"); or provide a statistical summary of each room and provider, including any one, any combination, or all of: mean visit duration; total visit duration; and visit count. In this regard, analyzing opportunities, which may be used to determine a duration that a healthcare worker spends with one or more patients, may be used for one or both of workload analysis or infection analysis.

As still another example, the methodology may be used for staff locating. Every healthcare provider may be easily located using the wristband worn by the healthcare provider. The location of each healthcare worker may be displayed on monitor for review and/or a healthcare provider may be contacted via message/reminder/call on the wristband worn or nearby stationary controllers. In this way, the methodology may be used for sending communications (such as electronic communications) to healthcare worker(s).

In one or some embodiments, assets, such as assets in a healthcare setting (e.g., hospital equipment), an office setting, a manufacturing setting, a home setting, or the like, may be tracked. Typically, an asset may be assigned a tag, such as an RFID tag, from which a beacon may be constantly sensed. In one or some embodiments, asset tracking comprises using a device attached to or associated with the asset that senses movement, and responsive thereto, wakes up in order to perform tracking functionality. After a period of time where there is no movement of the asset (e.g., 1 minute), the device may return to sleep, thereby conserving power. In this way, the device need not constantly generate a beacon for tracking.

As one example, a vibration sensor, such as a microvibration sensor, may be resident in the asset tracker in order to trigger a wake-up of at least a part of the functionality of the asset tracker. Responsive to waking up, any one, any combination, or all of the following functions may be performed: (i) determining movement and/or location of the asset (e.g., movement of the asset from one location to another, such as hospital equipment being moved from one room to another; movement of the asset itself such as where the asset is a dumbbell or other exercise equipment, monitoring movement of the dumbbell); (ii) determining who is moving the asset; determining timing of movement; (iv) determining whether operation of the asset is modified based on the movement (e.g., if the asset is in a first patient room with a first protocol (e.g., protocol for MRSA infection) to use the asset, and then the asset is moved to a second patient room with a second protocol (e.g., protocol for pneumonia) to use the asset, the operation of the asset may be modified to reflect the second protocol for the second patient room);

(v) determining how long the asset has been in movement (e.g., for exercise equipment, such as dumbbells, in order to track the amount of activity a patient performs, with the data later being uploaded and then reviewed by the doctor or physical therapist); or (vi) determining whether the asset is being moved from a predefined area and sounding an alarm when that occurs (e.g., if a piece of equipment is designated to remain in a predetermined patient area, responsive to determination that the piece of equipment is being moved, an alarm may be generated indicating that the piece of equipment should not be moved).

With regard to (i), it is contemplated that movement of the asset comprises movement of the entire asset (e.g., moving a machine from a first location to a second location; moving a dumbbell). Alternatively, it is contemplated that only a part of the asset is moved (e.g., a drawer/cabinet of an asset is opened or closed in order to access medicine, PPE or the like).

With regard to (ii), there are instances where it may not be necessary to determine the person performing the movement (e.g., in a home setting or a dementia care facility, it may be presumed as to the resident or the person with dementia performing the movement).

Alternatively, there are instances where it is desired to determine who is moving the asset. For example, in a hospital or business setting, it may be desirable to determine the healthcare provider that performs the movement. The asset tracker itself or another electronic device (such as a stationary controller) working in combination with the asset tracker may determine the person performing the movement. In particular, a controller resident on the asset tracker may directly communicate with a wireless device worn by the healthcare provider (e.g., a wristband (such as mobile wristband device, discussed below), RFID tag, or some other mobile electronic device) proximate to the asset tracker to identify the wireless device (and in turn the person associated with the wireless device) moving the asset. In this way, after wake-up of the asset tracker (such as due to movement), the controller on the asset tracker may begin to scan the vicinity in order to identify the wireless device (and optionally its location). Alternatively, responsive to movement, the asset tracker may generate a beacon, which may be received by another electronic device, such as a stationary controller resident in an area (such as a patient area). After wake-up, the asset tracker may generate the beacon for a limited period of time (e.g., 5 minutes, 1 hour, etc.) and then return to sleep. In turn, the stationary controller may communicate with wristbands in its proximity in order to identify the person moving the asset. The asset, in the course of moving between different rooms, may interact with multiple stationary controllers. This multiple interaction may be recorded in order to determine the path of the asset and the ultimate destination of the asset. Alternatively, the asset tracker itself may record the path of the asset and its ultimate destination.

Thus, a method and apparatus are disclosed for tracking an asset. The method may include: sensing, using an asset tracker that is associated with, connected to or part of the asset, movement of part or all of an asset: responsive to sensing the movement of part or all of the asset, waking up communication functionality of the asset tracker from a sleep state, wherein, in the sleep state, the asset tracker reduces power to the communication functionality of the asset tracker; transmitting, using the communication functionality of the asset tracker, an asset tracker communication, the asset tracker communication comprising an asset tracker identification, the asset tracker identification indicative of one or both of the asset tracker or the asset; responsive to transmitting the asset tracker communication, transmitting, by a mobile electronic device proximate to the asset tracker, a mobile electronic device communication comprising a mobile electronic device identification that is indicative one or both of a unique identifier for the mobile electronic device or of a person assigned to the mobile electronic device; receiving, by an asset tracking server, one or more communications comprising the asset tracker identification and the mobile electronic device identification; and responsive to the asset tracker determining that the asset tracker has not been moved for a predetermined amount of time, transitioning, by the asset tracker, to the sleep state thereby disabling the communication functionality of the asset tracker. In this way, the asset tracker may communicate with the mobile electronic device either directly, or indirectly (e.g., via a stationary controller).

In communicating indirectly, the asset tracker communication (such as a beacon) from the asset tracker is received by the stationary controller, and responsive to the stationary controller receiving the asset tracker communication, the stationary controller communicates with the mobile electronic device in order to trigger the mobile electronic device to transmit the mobile electronic device communication (e.g., either the stationary controller receives the mobile electronic device communication and transmits to the asset tracking server the one or more communications indicative of the asset tracker identification, the mobile electronic device identification, and a stationary controller identification, the stationary controller identification indicative of one or both of a unique identification of the stationary controller or of the area; or the mobile electronic device, communicating with the stationary controller, transmits the asset tracker identification, the stationary controller identification, and the mobile electronic device identification). In practice, the asset may be moved proximate to multiple stationary controllers, such as a first stationary controller associated with a first area and a second stationary controller associated with a second area. In moving to each of the respective stationary controllers: the respective stationary controller receives the communication from the asset tracker; responsive to the respective stationary controller receiving the communication, the respective stationary controller communicates with the mobile electronic device in order to trigger the mobile electronic device to transmit the mobile electronic device communication; and the respective stationary controller transmits to the asset tracking server the one or more communications indicative of the asset tracker identification, the mobile electronic device identification, and a first stationary controller identification, the first stationary controller identification indicative of one or both of a unique identification of the respective stationary controller or of the respective area.

Alternatively, the asset tracker may directly communicate with the mobile electronic device. In one instance, responsive to receiving the communication from the asset tracker, the mobile electronic device may access location functionality resident on the mobile electronic device (e.g., a GPS receiver) in order to determine a current location of the mobile electronic device and transmit to the asset tracking server the one or more communications indicative of the asset tracker identification, the mobile electronic device identification, and the current location of the mobile electronic device. In this regard, location information may be sent to the asset tracking server. In another instance, where location is not needed, the mobile electronic device may receive a plurality of the communications from the asset tracker responsive to movement of the asset tracker during a time period. In response to the mobile electronic device receiving the plurality of communications, the mobile electronic device may: determine respective times at which the mobile electronic device received the plurality of communications; determine, based on the respective times at which the mobile electronic device received the plurality of communications, the time period of movement of the asset tracker; and transmit to the asset tracking server the one or more communications indicative of the asset tracker identification and the determined time period movement of the asset tracker. In this regard, the mobile electronic device is configured to determine the time period of movement of the asset tracker. This type of functionality may be used in a situation where the time period movement of the asset is desired, such as an asset comprising weights, exercise equipment or the like, in which location of the asset may not necessarily be sought but time period of movement of the asset, such as movement of weights, is desired.

Still alternatively, the asset tracker may communicate with the asset tracker server, in which the asset tracker communicates bidirectionally with the mobile electronic device in order to obtain the mobile electronic device identification from the mobile electronic device and in which the asset tracker transmits to the asset tracking server the one or more communications comprising the asset tracker identification and the mobile electronic device identification. Further, the asset tracker may obtain a current location of the mobile electronic device from the mobile electronic device and may also transmit the current location received from the mobile electronic device. Thus, one, some or all of the asset tracker, the stationary controller, or the mobile electronic device may communicate with the asset tracker server.

Various items in a hospital setting may require replenishing periodically. For example, general use supplies, such as hand cleaning agent (e.g., hand sanitizer), gloves, or other PPE may be subject to inventory management. As another example, other medical items, such as drug items, medical equipment (e.g., supplies for catheterization), may likewise require monitoring/replenishing.

The discussion below is focused on monitoring hand cleaning agent use. However, the discussion may equally be applied to other items subject to monitoring/replenishing. In particular, hand cleaning agent, such as hand sanitizer or soap, may be dispensed from dispensers. Over time, the hand cleaning agent is dispensed so that no more hand cleaning agent remains in the dispenser. One manner to track the amount of hand cleaning agent in a respective dispenser is to include a level sensor inside of the dispenser to monitor the amount of hand cleaning agent remaining in the dispenser. Alternatively, a sensor separate from or associated with the dispenser may be used. For example, in one or some embodiments, the dispenser monitoring device, which may be separate from, integrated with, or associated with a stationary controller, may be used to monitor the amount of hand cleaning agent remaining in the dispenser. As discussed above, the stationary controller may determine, such as via a sensor (e.g., an ultrasonic sensor, a sound sensor, or the like), whether hand cleaning agent has been dispensed.

In particular, hand cleaning agent may be inserted into a dispenser using a bag or the like, so that according to specifications, a certain number of unit dispensing volume of the hand cleaning agent being projected for the bag (e.g., one bag translates into 1,000 unit dispensing volume of hand cleaning agent). Thus, the dispenser monitoring device may determine whether a dispense has occur and update the amount of hand cleaning agent in the dispenser accordingly (e.g., the dispenser monitoring device may determine any one, any combination, or all of: that there has been a certain number of dispenses since the bag was replaced; that there is a certain number of dispenses left in the bag; or that there is a certain number of dispenses left until triggering a communication to the backend server indicating that the bag of the dispenser should be replaced). In this regard, the dispenser monitoring device is unlike a level sensor that simply measures an amount of hand cleaning agent divorced or not triggered based on a dispensing event. Alternatively, instead of the dispenser monitoring device updating the amount of hand cleaning agent in the dispenser, responsive to the dispenser monitoring device determining that a dispense has occurred, the dispenser monitoring device may send a communication to the backend server, with the backend server then updating the amount of hand cleaning agent in the dispenser (e.g., determining the number of dispenses since the bad was replaced or the number of dispenses left in the bag).

As such, after a new bag is inserted into a dispenser, the stationary controller associated with the dispenser may be reset. Resetting may be performed in one of several ways. In one way, a software reset may be performed in which a technician, when installing the bag in the dispenser, may input via an app (or other software) on a mobile device of the installation. The input to the app on the mobile device may trigger a communication to the backend server. The communication may include one or both of the following: (1) an indication that a bag has been replaced; and (2) an indication as to the dispenser whose bag has been replaced. With regard to (2), the mobile device may obtain the indication of the dispenser in one of several ways. In one way, the app may include a field for the technician to manually input the indication (which may be labeled on the dispenser). In another way, the app may include a visual layout of the patient area, such as a floor of a hospital, so that the visual layout may be displayed on the display of the mobile device. The technician may indicate on the display (such as touching a part of the layout) to indicate the dispenser subject to refilling. In still another way, the mobile device may communicate with the dispenser, such as via near-field communication, in order for the dispenser to send its indication to the mobile device (and in turn for the indication to be sent in the communication).

In response to the input, a communication, either directly to the stationary controller or routed via the backend server, may be sent to the stationary controller associated with the dispenser of the new bag and the number of dispenses in the new bag (e.g., new bag installed with 1,000 dispenses). In this way, the software reset comprises a virtual button reset. In another way, a hardware reset may be performed in which a technician, when installing the bag in the dispenser, may press a button (or the like) on the stationary controller indicating the installation of a new bag, with the pressing of the button triggering a reset of the counter on the stationary controller (e.g., reset back to 1,000) and triggering a communication to the backend server indicating that the dispenser associated with the stationary controller has had its bag replaced.

After which, the stationary controller may track the number of dispenses of hand cleaning agent. When the number of dispenses reaches a predetermined amount (or where there are less than a certain number of dispenses remaining in the bag), the stationary controller may send a communication to another electronic device, such as the backend server, in order to notify that the bag of the dispenser needs replacing. For example, the stationary controller's communication may trigger an email or other notification to the facilities manager indicating the location of the dispenser needing its bag replaced. Alternatively, or in addition, the backend server allows polling of one, some, or all of the stationary controllers distributed throughout a facility in order for the stationary controllers to respond with a percentage or indication of an amount of hand cleaning agent remaining in their associated dispensers.

As discussed above, in one or some embodiments, proximity, such as temporal proximity, is analyzed in order to determine whether compliance with the hand hygiene and/or PPE action is sufficiently related to the hand hygiene and/or PPE opportunity. Further, in one or some embodiments, the hand hygiene and/or PPE opportunity may be deemed not to require compliance based on one or more rules. As one example, one or more criteria, such as any one, any combination, or all of role/status of healthcare provider, schedule of patient or location of the opportunity, may be used to determine whether a compliance determination with the hand hygiene and/or PPE opportunity is to be used in calculating statistics for compliance. For example, the healthcare provider may be a physical therapist. In practice, the physical therapist washes hands when entering a patient room or when entering a workout facility (e.g., where the patient is working out). The physical therapist can assist the patient to move to or from a workout facility and assist the patient out of the patient room or the workout facility. In such an instance, the physical therapist may be unable to wash his/her hands since the physical therapist is assisting the patient. Under typical circumstances, when the healthcare provider leaves a patient room, the healthcare provider is required to wash hands. However, when the healthcare provider is a physical therapist and is assisting a patient (such as during a scheduled physical therapy session), the physical therapist does not need to wash hands. In this regard, the system includes one or more rules to determine when the physical therapist does and does not need to wash hands. As such, the one or more rules may be used so that compliance with a specific opportunity, such as exiting a patient room, is not to be used in calculating statistical compliance for the physical therapist (e.g., the compliance determination for the exit opportunity is not determined at all, the compliance determination is performed for the exit opportunity but is tagged to indicate that the compliance determination is not to be used to calculating statistical compliance for the physical therapist).

Merely by way of example, the rules may be applied for a physical therapist scheduled to visit a first patient in a first room for physical therapy to be performed in another room. In such an instance, the physical therapist washes his/her hands prior to or upon entering the first room, helps the first patient out of the first room to the physical therapy room (whereupon exiting the first room, there is no requirement for the physical therapist to wash his/her hands), leave the physical therapy room (where there is also no requirement for the physical therapist to wash his/her hands), enter the first patient's first room (where there is also no requirement for the physical therapist to wash his/her hands), and then leave the first patient's first room (where there is a requirement for the physical therapist to wash his/her hands). The physical therapist may have a schedule in which to perform this for multiple patients (in room #1, #5, #8, etc.) so the sequence above may be followed accordingly for each patient in the respective rooms.

As another example, certain rooms or areas in a hospital may be designed as housing contaminated equipment. For example, healthcare workers entering a soiled utility room (or "dirty" room) need not clean hands, but need to clean hands upon exiting. As such, compliance with certain opportunities associated with these certain rooms (such as entrance opportunities) need not be used to calculate compliance statistics whereas other opportunities (such as exit opportunities) may need to be used to calculate compliance statistics. In particular, responsive to identifying that a certain type of opportunity (such as an entrance opportunity) is associated with a certain room or area (whether this is performed by the mobile electronic device associated with the healthcare worker, performed by the stationary controller (programmed to indicate that the stationary controller is a "special area" not subject to compliance), or performed by the backend server), any compliance determination associated with such opportunity may be excluded from compliance statistics for the healthcare worker. Conversely, responsive to identifying that another type of opportunity (such as an exit opportunity) is associated with the certain room or area, any compliance determination associated with such opportunity is included in compliance statistics for the healthcare worker.

In one or some embodiments, the rules may be applied in real-time (as the HH and/or PPE opportunity is occurring) or thereafter (e.g., after the HH and/or PPE opportunity has ended). For example, responsive to detecting the opportunity, the system, such as any one, any combination or all of the wristband, the stationary controller or the backend server, may determine that the opportunity does not need compliance. As such, any one, any combination, or all of the following may be performed: reminders to comply are output but compliance data is not determined, not transmitted, or tagged at the backend server as not to be used for compliance statistics; reminders to comply are disabled; the wristband does not determine compliance; the wristband determines compliance but does not transmit the compliance determination; the backend server determines not to log the compliance determination; or the backend server logs the compliance determination but tags the compliance determination as a special circumstance. As another example, the backend server, after the opportunity has ended and after receiving the compliance determination, may determine that compliance with the opportunity is not needed. As such, the backend server may either determine not to log the compliance determination or may log the compliance determination but tags the compliance determination as a special circumstance. Further, the application of the rules may be applied at any one, any combination, or all of: the wristband (e.g., the wristband may be programmed with the status of the healthcare provider and the rules stored locally in the wristband, and may determine which opportunities not to factor into compliance determination); at the stationary controller (e.g., the stationary controller may communicate with the wristband to determine the status of the healthcare provider and may access the rules stored locally in the stationary controller, and may determine which opportunities not to factor into compliance determination); or the backend server (e.g., the backend server may be access a database with the status of the healthcare provider and the rules, and may determine which opportunities not to factor into compliance determination).

As discussed above, HH and/or PPE may be relevant for a variety of settings, such as healthcare settings (e.g., hospitals, nursing homes, etc.) or other businesses (e.g., restaurants, schools, etc.). As a specific example, restaurants are typically tasked with following local or regional health codes. Typically, one of those health codes is following proper hand hygiene, such as proper hand washing in various areas of a restaurant including the kitchen and/or the bathroom. In order to monitor hand hygiene, the restaurant workers, such as chefs and/or waiters/waitresses, may wear a mobile electronic device, such as a wristband or the like.

Further, various parts of the restaurant may include additional hardware including any one, any combination, or all of: stationary controller(s) associated with hand cleaning agent dispensers (such as soap dispensers); electronic devices associated with moving objects (such as movement sensor(s) associated with doors (such as kitchen doors and/or bathroom doors)); stationary controller(s) associated with kitchen appliances (such as stoves, fryers, etc.); stationary controller(s) associated with bathroom appliances (such as commodes, toilets, etc.); or sound sensors positioned in or near the kitchen and/or bathroom.

Thus, depending on the layout and size of the kitchen and/or bathroom, one or more stationary controllers may be used. For example, in a smaller bathroom, a single stationary controller may solely be used or may be used with another sensor, such as a door sensor (sensing opening and/or closing of the door to the bathroom) and/or a sensor sensing flushing of the commode (e.g., a sound sensor configured to generate a signal to the stationary controller responsive to sending the sound of flushing). Responsive to the trigger (e.g., receiving a signal that the door has been opened and/or flushing sound has been detected), the stationary controller may set a timer in which the worker is to take hand cleaning agent. As another example, in a larger kitchen or bathroom, more than one stationary controller may be used, such as one stationary controller positioned proximate to the hand cleaning agent dispenser, another stationary controller positioned proximate to the door of the kitchen or bathroom, and still stationary controller positioned proximate to a device (such as a kitchen appliance or a bathroom appliance (e.g., a commode)). In this way, movement of the worker may be tracked in order to trigger a hand hygiene opportunity. For example, tracking movement into the kitchen or movement from the bathroom appliance to the dispenser may be used to identify a hand hygiene opportunity. Responsive to identifying the hand hygiene opportunity, the worker may be given a certain amount of time in which to take hand cleaning agent. If the worker does not take the hand cleaning agent within the certain amount of time (e.g., 2 seconds from identifying the hand hygiene opportunity), a reminder may be generated by one or both of the wristband associated with the worker or the stationary controller associated with the dispenser. In the event the worker fails to take hand cleaning agent with another amount of time (e.g., 6 seconds from identifying the hand hygiene opportunity), the hand hygiene opportunity is deemed non-compliant. Further, once hand cleaning agent is dispensed, the stationary controller may send a communication to the wristband to begin monitoring hand movements in order to determine either full or partial compliance. Similar to the discussion above, after the wristband determines compliance, the wristband may send the compliance determination to an external device, such as to the stationary controller or to the backend server.

Similar to determining compliance with one or more detected WHO hand hygiene opportunities, a method and system are disclosed that determines compliance with one or more detected restaurant hand hygiene opportunities, such as entering the kitchen, beginning a task in the kitchen (such as beginning to cook), and/or exiting the bathroom. In one or some embodiments, the method and system may comprise interaction between the wristband and another electronic appliance. As one example, interaction between the wristband and a stationary controller (which may be positioned or integrated with a hand cleaning agent dispenser) may trigger determination of compliance with a hand hygiene opportunity. In particular, responsive to interaction of the wristband with the stationary controller, the wristband may be triggered to determine hand hygiene action compliance (e.g., interaction results in the wristband being triggered to determine hand hygiene compliance, such as compliance with one or both duration of hand movements or specific hand movements). Various types of interaction are contemplated, as discussed above. As one example, communication between the wristband and stationary controller may trigger the wristband to determine hand hygiene action compliance (e.g., the wristband receives a communication from the stationary controller and determines that the communication has an RSSI signal indicative of being within the connection zone). As another example, the stationary controller's determination that hand cleaning agent has been dispensed triggers the stationary controller to send a communication (such as a dispensing communication) to the wristband in order for the wristband to determine hand hygiene action compliance (e.g., the wristband receives the dispensing communication from the stationary controller and is triggered to wake up and begin monitoring hand hygiene compliance).

As still another example, determination of movement into, out of, and/or within the kitchen and/or the bathroom may trigger determination of hand hygiene opportunity. In one instance, movement may be tracked using one or more stationary controllers, which may be located in different portions of the kitchen and or bathroom, such as at an entrance and/or in one or more interior portions. In particular, in communicating with multiple stationary controllers, the wristband may determine its movement, as discussed above.

In another instance, a sensor that is attached to the door, such as a proximity sensing-output generating device discussed above, may sense movement of the door (such as whether the door has opened or closed). Responsive to the sensor sensing movement of the door (such as opening the door to the kitchen or the bathroom), the sensor may send a communication to one or both of the wristband or the stationary controller, thereby triggering the sequence of determining hand hygiene compliance. In one or some embodiments, the sensor and/or the stationary controller are typically in sleep mode. For example, the sensor may include a micro-vibration sensor to wake up other parts of the sensor (such as communication functionality) responsive to movement from the door. As another example, the stationary controller may have its communication functionality awake in sleep mode but other aspects, such as sensing dispensing of hand cleaning agent, may be turned off. Responsive to the door moving (such as opening), the sensor may wake up and send a communication to the stationary controller. In turn, the stationary controller may wake up in order to begin monitoring whether someone has taken hand cleaning agent. In this way, one or both of the door sensor or the stationary controller may be in sleep mode and thus conserve power. Further, one or both of the sensor or the stationary controller may communicate with the wristband responsive to waking up in order to identify the person associated with the wristband. For example, responsive to the sensor waking up, the sensor may send an identify communication wirelessly, such as via Bluetooth, to wristbands within a certain range. Responsive to receiving the identify communication, the wristband may send a communication with a code identifying the person associated with the wristband. As another example, responsive to the stationary controller waking up, the stationary controller may send an identify communication wirelessly to wristbands within a certain range, and receive the identifying code in response.

In still another instance, a sensor, such as an audio sensor, may be used to trigger the hand hygiene action determination. For example, a sensor may be configured to sense a predetermined sound, such as a toilet flushing. Responsive thereto, the sensor may send a communication to the wristband to begin monitoring the hand hygiene action for compliance determination (e.g., responsive to receiving the communication from the sensor, the wristband sets a timer in which the wearer of the wristband is to comply with the hand hygiene action; otherwise, the hand hygiene action is determined as non-compliant).

Alternatively, in the restaurant or hospitality-industry setting, workers may typically be tasked with cleaning hands at a predetermined schedule (such as every 30 minutes). In one embodiment, the predetermined schedule (e.g., every 30 minutes) is static throughout the day. Alternatively, the predetermined schedule may vary and be dynamic throughout the day (e.g., during less busy times, such as 11:00 am-noon, set the predetermined schedule to every 30 minutes, while during busier times, set the predetermined schedule to every 10 minutes). Alternatively, or in addition, the predetermined schedule may be set based on status of role of the provider (e.g., a chef has a shorter predetermined schedule than a server). Thus, in one or some embodiments, a single device, such as a mobile electronic device associated with the worker, may be used to: (1) determine whether there is a hygiene opportunity; (2) detect whether hand cleaning agent has been dispensed; (3) detect hand movements; and (4) detect whether the hand movements are sufficient for hygiene compliance. With regard to (1), the mobile electronic device may include a timer, which indicates the schedule at which the hygiene opportunities are determined (e.g., time set to 30 minutes to indicate a hygiene opportunity every 30 minutes). In one embodiment, an output, such as an output generated by the mobile electronic device, may be generated when a hygiene opportunity is determined. Alternatively, no output is generated responsive to determining a hygiene opportunity. With regard to (2), the mobile electronic device may include one or more sensors whose data may be analyzed by a processor in the mobile electronic device in order to detect whether hand cleaning agent has been dispensed. In one example, the mobile electronic device may include a sound sensor, which may generate sound data at, approximately before, or approximately after the hygiene opportunity is determined. The processor on the mobile electronic device may analyze the sound data generated at, approximately before, or approximately after the hygiene opportunity is determined in order to determine whether the sound data is indicative of hand cleaning agent being dispensed. In another example, the mobile electronic device may include a motion sensor, which may generate motion data at, approximately before, or approximately after the hygiene opportunity is determined. The processor on the mobile electronic device may analyze the motion data generated at, approximately before, or approximately after the hygiene opportunity is determined in order to determine whether the motion data is indicative of a hand movement where the palm of a hand is moved to face upward or positioned to face upward, in turn indicating that the hand is positioned or has moved to receive hand cleaning agent from a dispenser. Still alternatively, the mobile electronic device may rely on a communication from a stationary controller indicative that the stationary controller has detected a dispense of hand cleaning agent.

With regard to (3) and (4), the mobile electronic device may include one or more sensors whose data may be analyzed by a processor in the mobile electronic device in order to detect whether hand movements are sufficiently performed. For example, the mobile electronic device may include one or more motion sensors, which may generate motion data at, approximately before, or approximately after detecting dispensing of hand cleaning agent. The processor on the mobile electronic device may analyze the motion data generated at, approximately before, or approximately after detecting dispensing of hand cleaning agent in order to determine whether the motion data is indicative of sufficient hand cleaning (e.g., at least a certain period of time, such as 20 seconds, of hand movement; at least one or more predetermined hand motions; etc.). In this way, the mobile electronic device need not rely on any external electronic device in order to perform each of (1), (2), (3), and (4). Alternatively, the mobile electronic device may rely on an external electronic device (such as a stationary controller) in order to perform any one, or any combination of (1), (2), (3), and (4). Further, in the event that the provider has not cleaned hands within the predetermined time period (such as 30 minutes), the mobile electronic device (and/or a stationary controller proximate to the mobile electronic device) may generate a reminder for the provider to clean hands. In one or some embodiments, in the event that the provider does clean hands, the time at which the hands were cleaned may be designated as the last time at which the provider cleaned hands. Going forward, the mobile electronic device may then use this last time to determine an elapsed time since the last cleaning of the hands, and compare the elapsed time with the predetermined time period.

Still alternatively, instead of the reminders being generated based on a predetermined schedule, determining when to remind a provider may be location-based. For example, responsive to determining that the provider has entered and/or exited the kitchen, exited the bathroom, went to a different location (such as a different room or a different table at a restaurant), a reminder may be generated (by the wristband and/or by a stationary controller). Thus, in one or some embodiments, the trigger to determine whether to monitor hand hygiene (and optionally to generate an output to remind a respective worker to perform hand hygiene) is based on location (such as identifying that the worker has moved from a first location to a second location). One or both of the first location or second location may be a service area, which may comprise an area for service of a customer, such as a patient, a restaurant patron, an airline passenger, or the like. The service area may be defined as having or potentially having a customer. As discussed above, the service area may comprise a patient area (whether the patient area includes a patient or not), a restaurant area, an airline check-in area, or the like. In one or some embodiments, the first location may be considered a "dirty" location (or a location may necessitate hand cleaning, where the location itself may be designated as a "dirty" location, the equipment stored therein (such as kitchen equipment preparing raw animal products or washing dishes, or patient equipment that is soiled or contaminated), or a patient therein diagnosed with a communicable disease) and/or the second location may be considered a clean location (or a location where hand hygiene is recommended prior to interacting with someone (such as a restaurant patron or a patient) or interacting with something (such as kitchen equipment or medical equipment)).

Alternatively, or in addition, reminders may be generated for the worker and/or for patrons of the restaurant to see and/or hear. As discussed above, outputs may be generated at various stages for the worker, such as reminder(s) to perform certain actions, feedback as to whether the worker complied or did not comply with the protocol at various stages, etc. In one or some embodiments, the output may be generated for someone other than the worker or the healthcare provider. As discussed above, hospitality workers, such as restaurant workers, serve patrons. Those patrons may be interested in knowing whether a hospitality worker serving them has complied with HH protocol(s). As such, the output, such as whether the hospitality worker complied or did not comply with the HH protocol(s), may be generated responsive to interaction of the hospitality worker with patron(s). In one or some embodiments, the mobile electronic device, such as the wristband, may be triggered to output the compliance determination responsive to the mobile electronic device, on its own, identifying an opportunity associated with interacting with a patron. As discussed above, there are various ways in which the mobile electronic device may identify approaching a patron, such as approaching a patron area. Likewise, in response to the mobile electronic device identifying a patron interaction (such as tracking the worker's movement into a designated dining area (or service area), the mobile electronic device may generate the output (such as a red LED light activated to indicate non-compliance and a green LED light activated to indicate compliance). Alternatively, the mobile electronic device may be triggered to output the compliance determination responsive to interaction with another electronic device, such as a stationary controller. For example, a stationary controller may be positioned proximate to a patron (such as at a dining table of the patron). Responsive to the mobile electronic device interacting with the stationary controller (e.g., the mobile electronic device communicates with the stationary controller via near-field communication), one or both of the mobile electronic device or the stationary controller may generate the output indicative of compliance (e.g., the wristband may generate an output and/or the stationary controller may generate the output). In this way, the output generated may be triggered based on interaction with the patron, thus being personalized to the patron.

As discussed above, an electronic device, such as a wristband, may be associated with a person, such as a provider. Assigning of the electronic device, such as a wristband, to a specific person, such as a specific healthcare provider, may be performed in one of several ways. As discussed above, the wristband may have wireless communication functionality, such as any one, any combination, or all of: Bluetooth communication functionality; Wi-Fi communication functionality; cellular communication functionality; or the like. The wristband, using the wireless communication functionality, may communicate with a remote server (such as via the Internet). In turn, the remote server may determine any one or both of the following: (1) who is currently assigned the wristband; and (2) assign (or reassign) the wristband to a specific person.

For example, the wristband may have a code (e.g., XYZA). The remote server may correlate that code in a database to an identification of the specific person (e.g., code XYZA is correlated to "Jane Doe"). In practice, the wristband may send, via its wireless communication functionality, its code to a local mobile controller (e.g., the wristband uses its near-field communication functionality to communicate with the local mobile controller). In turn, the mobile controller sends, via the Internet, the code to the remote server. The remote server may then access the database to determine the specific person assigned the wristband. With regard to assigning or reassigning, the remote server may simply reprogram the database so that a specific code is correlated to a different person (e.g., change correlation of XYZA to "Jane Doe" to XYZA to "John Roe"). Various communication protocols are contemplated. As one example, the remote server and the mobile controller may communicate with one another using web sockets technology. In this way, assigning, or reassigning, of the wristbands may be performed quickly and easily.

As another example, the wristband may be assigned for temporary or limited use, such as in the instance of a temporary worker or f a permanent worker who has misplaced his/her wristband. In order to assign the wristband, the worker may access an app (such as resident on a smartphone) in order to communicate with one or both of the wristband (such as wirelessly by near field communication, such as Bluetooth) and a backend server (such as wirelessly by Wi-Fi to a base station and then via the internet). In this way, the app may obtain an identification of the wristband, may obtain an identification of the worker (such as a name or an ID number), and may send them to the backend server in order for the backend server to store the correlation of the ID of the wristband with the ID of the worker. Further, the assignment may be designated as temporary in one of several ways, such as temporary in terms of time (the correlation is valid only for the next 8 hours) or until the ID of the wristband is reassigned.

FIG. 1A is a first example block diagram of a HH and/or PPE system 100, with a mobile wristband device 105, a local stationary controller 115 and a back-end server 130. The mobile wristband device 105 and the local stationary controller 115 may communicate wirelessly, such as via 110. Example wireless protocols may comprise near-field communication protocols, such as RFID, Bluetooth, ZigBee or the like. The local stationary controller 115 may likewise communicate with back-end server 130. As shown in FIG. 1A, the communication between the local stationary controller 115 and back-end server 130 is wireless 120 via a Wi-Fi base station 125. Other methods of communication are contemplated.

FIG. 1B is a second example block diagram of a HH system 150, with a mobile wristband device 153, a dispenser 151, a local stationary controller 152, wireless router 154 (e.g., Wi-Fi transceiver), cloud computing 156, compliance analysis 158, and output device 159 (e.g., smartphone or tablet). The HH system 150 is configured to perform any one, any combination, or all of the following four functions: data tracking, data collection, data analysis and provider motivation. Each provider wears a wristband 153 with built-in motion sensors, discussed in more detail below. In one implementation, each wristband is assigned to and worn by only one person (e.g., healthcare provider; service provider). Further, there is a one-to-one mapping between the person's information (e.g., name, role, etc.) and the MAC address of the wristband. As discussed further below, stationary controllers (e.g., positioned inside and/or outside a patient room) may be mapped to a particular area (e.g., a room location).

When the healthcare provider approaches the entrance of a patient's room, the wristband sensor on wristband 153 detects the beacon from the controller 152 installed close to, adjacent to, proximate to, or integrated with the sanitizer dispenser 151 and send a hand hygiene alert to the healthcare provider. Alternatively, the wristband 153 may transmit a beacon to the controller 152, which in turn may detect the wristband 153, with the controller 152 sending a signal to wristband 153, as discussed above. The wristband sensor in wristband 153 records the healthcare provider's hand motion data during the HH action, which is transmitted via the controller 152 and wireless router 154 to cloud computing 156, which may comprise a hospital server.

As discussed above, controller 152 may be mounted proximate to dispenser 151, such as within or less than 1 inch, within or less than 2 inches, within or less than 3 inches, etc. of dispenser 151. Controller 152 may include electronics that performs one or more functions. For example, controller 152 may generate a beacon (or other wireless signal) that is received by the wristband 153. As discussed above, in response to receiving the beacon, the wristband 153 is configured to generate an output indicative of the hand hygiene alert (e.g., an audible output and/or a visual output indicative to the healthcare provider to perform the hand cleaning process). In this regard, the controller 152 generates the beacon that begins the hand hygiene notification process. Alternatively, controller 152 may receive a beacon from wristband 153, such as a Bluetooth signal. In response, controller 152 may determine a proximity to wristband 153, and if sufficiently proximate, send a wake-up signal to wristband 153 to begin motion sensor monitoring.

As another example, the controller 152 may monitor one or more operations related to dispenser 151. In one implementation, the controller 152 may monitor at least one aspect of the dispenser 151 itself. For example, the controller 152 may monitor an internal operation of the dispenser 151. In a first specific implementation, the controller 152 may include a sensor, such as a sound sensor, that may monitor the internal operation of dispenser 151 (e.g., a sound sensor that senses sound generated by a motor within dispenser 151 that dispenses antibacterial product into the hand of the healthcare provider). Thus, in the first specific implementation, the controller 152 may monitor the dispenser 151, as opposed to movement of the provider. In a second specific implementation, the controller 152 may include a sensor, such as an infrared sensor, that may monitor the movement of the provider in an area proximate to the dispenser 151. In a third specific implementation, the controller 152 may include multiple sensors that monitor the internal operation of the dispenser 151 and the movement of the provider in an area proximate to the dispenser 151.

Responsive to the controller 152 determining that the monitored aspect of the dispenser 151 has occurred (e.g., the controller 152 determining that the dispenser 151 has dispensed the antibacterial product and/or the controller 152 determining that the healthcare provider is proximate to the dispenser 151), the controller 152 may send a communication to the wristband 153. Responsive to the communication, the wristband 153 may begin to track the hand movements of the healthcare provider and/or may generate one or more outputs in order to provide instruction to comply with protocol(s) (such as hand hygiene protocols). In one embodiment, the communication sent from controller 152 is a broadcast communication. Alternatively, the communication sent from controller 152 to wristband 153 is a communication sent via a communication channel to wristband 153. For example, the wristband may generate the one or more outputs responsive to receiving the communication and/or responsive to determination of compliance or non-compliance (e.g., responsive to determination of non-compliance (such as not rubbing for at least the predetermined amount of time and/or not performing the proper hand movements, the wristband may generate the output indicating the deficiency). Alternatively, the wristband 153 may begin to track the hand movements responsive to receiving the beacon from the controller 152.

The wristband 153 may thus record the provider's hand motion data during the HH action. In one implementation, the wristband 153 may analyze the hand motion data locally (within the wristband 153), and transmit the analysis (and/or the hand motion data) to the controller 152. Alternatively (or in addition), the wristband 153 may transmit the hand motion data to controller 152 for analysis by the controller 152 and/or for analysis by cloud computing 156.

After the analysis of the hand motion data (either by wristband 153, controller 152 and/or cloud computing 156), an indication of the results of the analysis may be transmitted to the provider. In one implementation, the indication may be output on wristband 153. In one example, the wristband 153 may perform the analysis and may output the indication of the results of the analysis (e.g., whether the healthcare provider adequately cleaned his/her hands; whether the healthcare provider inadequately cleaned his/her hands; an indication how to improve hand cleaning (e.g., aurally outputting to the healthcare provider to clean the hands for a longer period of time, such as for 10 more seconds responsive to determining that the healthcare provider rub his/her hands for 10 seconds less than the hand hygiene protocol dictates)). In another example, the controller 152 may perform the analysis and may transmit to the wristband 153 the indication for output by the wristband 153 of the indication of the results of the analysis and/or may output the indication itself. In still another example, the controller 152 may perform the analysis and may transmit to cloud computing 156 the indication, which may transmit to (or may be available for download by) a mobile app running on a mobile electronic device associated with the healthcare provider. In yet another example, cloud computing 156 may perform the analysis using compliance analysis 158 (e.g., a computer associated with the infection control team may analyze hand hygiene data) and may transmit to (or may be available for download by) a mobile app running on a mobile electronic device associated with the healthcare provider (e.g., output device 159).

In one implementation, the hygiene protocol, including the HH protocol, is standard and consistent for different locations within a premises. In one embodiment, the hygiene protocol may include any one, any combination, or all of the following: HH protocol; mask protocol (e.g., whether or not to wear a face mask); gown protocol (e.g., whether or not to wear a hospital gown); gloves protocol (e.g., whether or not to wear latex rubber gloves); footwear protocol (e.g., whether or not to wear booties over the shoes); etc. For example, the hygiene protocol may be the same for a first hospital room and a second hospital room, or may be the same for a first section of the hospital and a second section of the hospital. As discussed further below, various HH protocols may be used, such as those issued by WHO. Alternatively, the hygiene protocol is different for different locations within a premises. For example, a first hospital room may have a first hygiene protocol and a second hospital room may have a second hygiene protocol, with the first hygiene protocol being different than the second hygiene protocol. In particular, the first hygiene protocol may be different from the second hygiene protocol in any one, any combination, or all of: hand hygiene protocol (e.g., whether to use hand sanitizer or use soap/water), mask protocol, gown protocol, or footwear protocol. As another example, a first section of the hospital, such as the ICU (or ICU-A), may have the first hygiene protocol whereas a second section of the hospital, such as the neonatal unit or ICU B, may have the second hygiene protocol (e.g., the ICU requires face masks whereas the neonatal unit requires gowns). In another embodiment, the protocol may be different based on different areas in a restaurant premises, such as a first protocol for the kitchen and a second protocol for the dining area.

The hygiene protocol may be communicated to one or both of the stationary controller or the wristband in one of several ways. In one way, the stationary controller may have the specific protocol pre-programmed thereon (either upon installation or sent from the server). For example, responsive to a determination that a patient with pneumonia is staying in a particular room, the server may send a communication to the stationary controller (assigned to that particular room) to indicate the hygiene protocol for a patient with pneumonia. Similarly, the wristband may determine the specific protocol in one of several ways. In one way, the stationary controller in the specific location may send or push the protocol to the wristband. For example, a stationary controller in the first section of the hospital may send the first protocol (e.g., the correct hand movements or the requirement of a face mask) to the wristband in response to the stationary controller determining that the wristband is in proximity (see 638 of FIG. 6C). In another way, the wristband may, itself, determine its location, transmit the location to a server, with the server in response sending the specific protocol to the wristband.

In practice, the stationary controller and/or the wristband may generate an output indicating the protocol (e.g., the deviation in the protocol, such as wearing a face mask). For example, responsive to the stationary controller determining that the wristband is in proximity, the stationary controller may generate an output (e.g., an audio output stating: "please put on a face mask"; "please use soap and water to wash hands"; "please use hand sanitizer to wash hands"; "please first use soap and water to wash hands, then put on a gown, finally put on gloves, and then enter the room"; "please first use hand sanitizer, then put on mask, and then enter the room"; "please first remove your gloves, then your gown, and then use soap and water to wash your hands"). In this way, the output may provide a reminder as to the protocol(s) to be followed (e.g., a specific protocol that is assigned to a patient room or a general protocol that is assigned to an entire hospital). As another example, the wristband may generate the output, such as the audio output.

Further, the determination whether to generate the output may be dependent on one or more factors, such as any one, any combination, or all of: the status (interchangeable termed a role) of the person; the type of protocol (e.g., whether the protocol is changeable); whether the protocol has changed; etc. For example, status may be defined in one of several ways, such as: a trainee (e.g., a new employee); an existing employee; a visitor; etc. In this regard, the output, either from the stationary controller and/or from the wristband, may be dependent on the status of the person (e.g., for a trainee, generate one or more outputs such as: generating a reminder to wash with soap and water; generating a reminder as to the correct sequence for performing the PPE protocol; generating a reminder as to the correct HH protocol and/or the correct PPE protocol; generating a reminder as to the correct sequence for the HH protocol and the PPE protocol when entering and/or exiting the patient area). As one example, the status of the person may be an employee. As another example, the status may be more specific, such as "chef" or "server". The status may be stored, for example, on the wristband. In the example of the stationary controller generating the output, the stationary controller may first receive the status of the person (e.g., the wristband transmitting the status of "trainee" to the stationary controller upon the wristband coming into proximity with the stationary controller). The stationary controller may determine whether to generate the output (e.g., generating a reminder to wear a mask) dependent on whether the person is designated as a trainee. If so, the stationary controller may generate the output. Conversely, in the event that the person is an "employee" (meaning more experienced than a trainee in the protocols of the hospital), responsive to the stationary controller determining the status of the person as "employee", the stationary controller may determine not to generate the output (e.g., not generate a reminder to wear a mask). As another example, status of "chef" may indicate generating an output, whereas status of "server" may indicate not to generate an output. Alternatively, the system may generate the reminder (and/or monitor hygiene compliance) based on both the status of the worker and the location of the worker. For example, a worker assigned the status of "chef" who enters the specific area, such as a kitchen area (triggered based on entry to the kitchen area alone or triggered based on entry to the kitchen area from an area considered unclean (such as the bathroom)), may receive a reminder (and optionally be evaluated for compliance), whereas a worker assigned the status of "server" who enters the same area will not receive a reminder (and optionally will not be evaluated). As another example, the worker assigned the status of "server" who enters a different area (such as the dining area or a different table in the dining area) may receive a reminder (and a compliance determination). In one embodiment, a momentary presence within a location (such as a respective area or a respective table) may trigger the reminder (and compliance determination). Alternatively, a presence of at least a predetermined amount of time (e.g., 3 seconds of communication with the stationary controller located in the respective area) may trigger the reminder (and compliance determination). Alternatively, or in addition, a sensor, such as an ultrasonic or infrared sensor, positioned to identify a transition into the respective area and/or a presence of at least the predetermined amount of time may trigger the reminder (and compliance determination). Similarly, in the context of the wristband generating the output, the wristband may determine whether to generate the output based on the status of the person. As discussed above, the wristband may determine, either based on a communication from the stationary controller or from another external device, to output a particular protocol for a specific room or section of a hospital. The wristband may condition the output of the particular protocol on the status of the person. Specifically, the wristband may indicate that the wearer is a trainee. Responsive to the wristband determining that the wearer is a trainee, the wristband may determine to output the special protocol (e.g., generate a vibration, generate an audio and/or display output). Conversely, responsive to the wristband determining that the wearer is an "employee", the wristband may determine to output the special protocol (e.g., generate a vibration, generate an audio and/or display output).

As another example, determination whether to output the reminder may be based on the type of protocol. For example, the protocol may comprise a hygiene protocol that may be changed. In one particular example, a patient area may have an associated hand hygiene protocol selected from either hand sanitizer or soap/water based on the patient assigned to the patient area. Responsive to identifying that the hand hygiene protocol associated with the patient area may be changeable, an output may be generated in order to remind a healthcare worker interacting with the patient in the patient area (such as reminding the healthcare worker upon exit from the patient area to comply with the hand hygiene protocol currently associated with the patient area).

As still another example, determination whether to output the reminder may be based on whether the protocol has changed. In particular, responsive to identifying that the protocol has changed, such as having been changed within a period of X days since the present time at which the output is to be generated, it may be determined to generate the output.

Alternatively, or in addition, the wristband may include a simple and robust algorithm for hand rubbing detection. Rubbing hands with an alcohol-based formulation is one manner for routine hygienic hand antisepsis. Alternatively, soap and water may be used mostly for cleaning soiled hands.

In still another implementation, the wristband may generate sensor data that may be analyzed by HH and/or PPE analytics. In particular, the sensor data may be stored in a HH and/or PPE database, which provides a variety of data to hospital management team and individual healthcare providers. Detailed HH and/or PPE compliance reports generated by date, location (floor, unit or room), or department are available to hospital administrators and can be used to set up incentive/penalty programs to motivate healthcare providers. Infection control professionals also have access to the information to differentiate between staff groups and identify trends based on time of shift, protocols, or other desired metrics. Further, a mobile app may be used, whereby healthcare providers can compare their performance to their colleagues' and be motivated through peer pressure and team competition. Thus, in one implementation, only HH compliance is stored and/or analyzed. In another implementation, only PPE compliance is stored and/or analyzed. In still another implementation, both HH and PPE compliance are stored and/or analyzed.

Figure 1D:
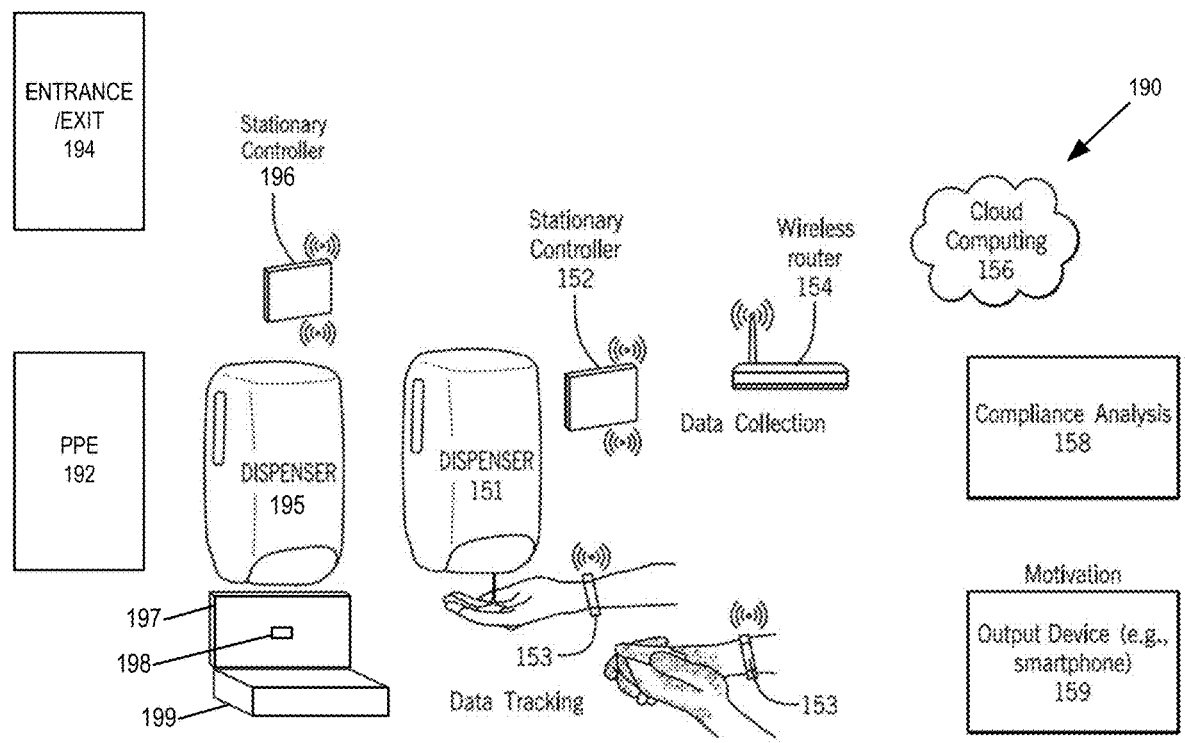
FIG. 1D is an example block diagram of a hand hygiene and personal protective equipment system, with a mobile wristband device, personal protective equipment, an entrance/exit, a dispenser, a local stationary controller, compliance analysis, one or more output devices, and cloud computing.
Figure 1C:
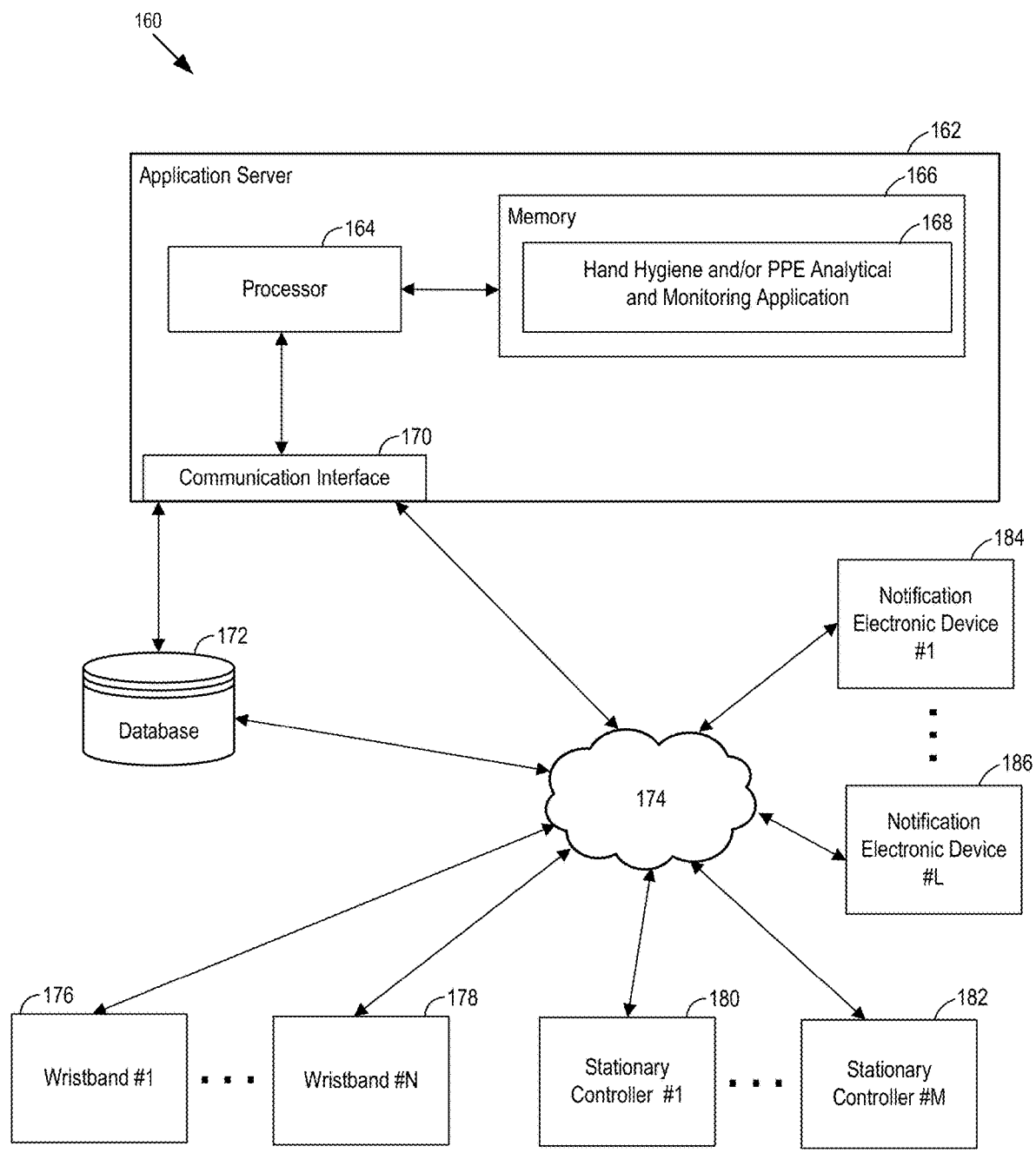
FIG. 1C is a third example block diagram of a hand hygiene and/or PPE system, with an application server, a database, one or more wristbands, one or more stationary controllers, and one or more notification electronic devices.

FIG. 1C is a third example block diagram of a HH and/or PPE system 160, with an application server 162, a database 172, one or more wristbands (wristband #1 (176) to wristband #N (178)), one or more stationary controllers (stationary controller #1 (180) to stationary controller #M (182)), and one or more notification electronic devices (electronic device #1 (184) to electronic device #L (186)). FIG. 1C shows N wristbands, M stationary controllers and L electronic devices. Any numbers of wristbands, stationary controllers, and electronic devices are contemplated.

The application server 162 is configured to include the hardware, software, firmware, and/or middleware for operating the HH and/or PPE analytical and monitoring application 168. In a first implementation, the application server 162 is configured for analysis and/or monitoring of HH compliance. In a second implementation, the application server 162 is configured for analysis and/or monitoring of PPE compliance. In a third implementation, the application server 162 is configured for analysis and/or monitoring of both HH and PPE compliance. In the third implementation, the application server 162 may analyze and/or monitor the HH compliance and PPE compliance independent of one another. Alternatively, the application server 162 may analyze and/or monitor the HH compliance and PPE compliance dependent on one another. Application server 162 is shown to include a processor 164, a memory 166, and a communication interface 170. The HH and/or PPE analytical and monitoring application 168 is described in terms of functionality to manage various stages of managing the HH and/or PPE data as generated by one or more wristbands (wristband #1 (176) to wristband #N (178)) and/or one or more stationary controllers (stationary controller #1 (180) to stationary controller #M (182)), and for notification via electronic device #1 (184) to electronic device #L (186).

HH and/or PPE analytical and monitoring application 168 (and HH and/or PPE analytics 306 and access control 374, 482 resident in wristband, HH and/or PPE control 432, and access control 434 in stationary controller, discussed further below), may be a representation of software, hardware, firmware, and/or middleware configured to implement the management of any one, any combination, or all of the stages of hand hygiene compliance.

The HH and/or PPE system 160 may further include a database 172 for storing data for use by the HH and/or PPE analytical and monitoring application 168. For example, data generated by one or both of wristbands 176, 178 and stationary controllers 180, 182 may be stored in database 172.

The application server 162 may communicate with the database 172 directly to access the data. Alternatively, the application server 162 may also communicate with the database 172 via network 174 (e.g., the Internet). Though FIG. 1C illustrates direct and indirect communication, in one implementation, only direct communication is used, in an alternate implementation, only indirect communication is used, and still in an alternate implementation, both direct and indirect communication is used.

The application server 162 may communicate with any number and type of communication devices via network 174. As illustrated in FIG. 1C, application server 162 may communicate with electronic devices associated with one or more users. For example, FIG. 1C depicts N wristbands 176, 178, M stationary controllers 180, 182, and L electronic devices 184, 186. The wristbands 176, 178 may communicate directly with application server 162 or may communicate via stationary controllers 180, 182 (not shown). The depiction in FIG. 1C is merely for illustration purposes. Fewer or greater numbers of wristbands, stationary controllers, and electronic devices are contemplated.

Electronic device #1 (184) to electronic device #L (186) shown in FIG. 1C may be used to notify one or more individuals, such as the healthcare provider associated with one of wristbands 176, 178, or another healthcare provider not associated with one of wristbands 176, 178. Further, electronic device #1 (184) to electronic device #L (186) may comprise smartphones, tablet computers, personal computers (PCs), server computers, handheld or laptop devices, multiprocessor systems, microprocessor-based systems, network PCs, or devices, and the like.

FIG. 1D is an example block diagram 190 of a HH and PPE system, with a mobile wristband device 153, personal protective equipment 192, an entrance/exit 194, one or more dispensers 151, 195, one or more stationary controllers, 152, 196, compliance analysis 158, one or more output devices 159, and cloud computing 156. As discussed further below, the stationary controller may be associated (such as proximate to) entrance/exit 194, which is the entrance and/or exit to a patient area (e.g., a patient room). In one implementation, two dispensers are used, with one dispenser located outside of the room near or proximate to the entrance/exit 194 (e.g., dispenser 151 in FIG. 1D) and a second dispenser located inside the room near or proximate to the entrance/exit 194 (e.g., dispenser 195 in FIG. 1D). For example, one typical clinical setting has a sanitizer dispenser (and/or a washing station) and PPE station positioned at the entrance to a patient room and another sanitizer dispenser (and/or a washing station) inside the patient room.

In practice, when the wristband 153 is proximate to dispenser 151 (as the provider is outside the room and moving toward the entrance), stationary controller 152 may communicate with wristband 153 in order to identify or predict the HH and/or PPE opportunity upon entrance. As discussed above, identifying or predicting the HH opportunity and the PPE opportunity may be dependent on one another; alternatively, identifying or predicting the HH opportunity and the PPE opportunity may be independent of one another. Likewise, when the wristband 153 is proximate to dispenser 195 (as the provider is inside the room and moving toward the exit to leave), stationary controller 196 may communicate with wristband 153 in order to identify the HH and/or PPE opportunity upon exit. Again, identifying or predicting the HH opportunity and the PPE opportunity upon exit may be dependent on one another; alternatively, identifying or predicting the HH opportunity and the PPE opportunity upon exit may be independent of one another. Alternatively, instead of having two stationary controllers, a single stationary controller (such as stationary controller 152 outside of the room) may be used with an electronic device inside of the room that communicates with stationary controller 152.

As discussed above, the stationary controller (such as stationary controller 152, 196) may be associated with a dispenser (such as dispenser 151, 195), such as positioned proximate to the respective dispenser and/or integrated within the respective dispenser. The stationary controller 152, 196 may sense the action of the dispensing in one of several ways, such as sensing that there is movement within the dispenser 151, 195 (e.g., sensing movement of a motor or a mechanical arm in the dispenser 151, 195 that dispenses hand cleaning agent) and/or sensing that there is hand movement proximate to the dispenser 151, 195 (e.g., positioning a sensor, such as an infrared sensor or an ultraviolet sensor positioned relative or within the dispenser 151, 195 in order to sense the hand movement in order to take hand cleaning agent from the dispenser 151, 195). The sensor (whether infrared or ultraviolet) may be positioned relative to the dispenser 151, 195 in one of several places, such as underneath and to a side of the dispenser 151, 195 (in order to sense a sweeping movement, placed to the right of the dispenser 151, 195 to sense a right to left sweeping hand movement or placed to the left of the dispenser 151, 195 to sense a left to right sweeping hand movement) or directly underneath the dispenser 151, 195 (such as illustrated by sensor 198 positioned facing directly outward and placed within backplate 197). Further, drip tray 199 may be positioned directly underneath dispenser 195, with in one embodiment the drip tray housing the stationary controller 196. Alternatively, the stationary controller 196 may be housed in backplate 197.

As discussed above, one or more electronic devices, such as depicted in FIGS. 1B and 1D, may determine whether a person is entering or exiting the area (e.g., patient room) in one of several ways. In one way, one or both of the stationary controllers 152, 196 may determine interaction (and in turn whether the person is entering or exiting the room) based on timing of the interaction. As one example, it may be assumed that the wristband worn by the person who is entering/exiting the room communicates (e.g., via Bluetooth) for a longer period of time than a person who is merely walking past the entrance to the room. In particular, the healthcare provider will remain at the proximity of the entrance for several seconds (to wash hands, don/doff PPE, open door, etc.), unlike someone simply walking by the patient room. Thus, in one implementation, the wristband signal, as detected by stationary controller (e.g., stationary controller 152 positioned at or outside of the entrance to patient room) will be strong (greater than a predetermined threshold) for a longer period of time when entering/exiting the room (as compared to walking by). In this way, the stationary controller may count the amount of time this pattern occurs (e.g., greater than the predetermined threshold) and responsive to determining that the amount of time is greater than the predetermined threshold, thereby detect a hygiene opportunity, such as if a healthcare provider is entering or exiting the room.

Thus, one or both of the wristband or the stationary controller may determine a period of time that the wristband (with its unique ID) and the stationary controller (also with its unique ID) interact. The wristband and/or the stationary controller may determine an entrance/exit opportunity responsive to determining that the interaction is greater than a predetermined time period. More specifically, the wristband and/or the stationary controller may determine whether the opportunity is an entrance or exit opportunity based on timing. For example, responsive to determining that this interaction is less than a predetermined time (such as 30 seconds), the interaction may be determined to be an entrance. Responsive determining that this interaction is greater than a predetermined time (such as 30 seconds), the interaction may be determined to be an exit.

Alternatively, multiple controllers, such as depicted in FIG. 1D, may be used to determine whether a person is entering or exiting the patient area. In particular, one stationary controller, such as stationary controller 152 is positioned outside of the patient room and a second stationary controller, such as stationary controller 196, is positioned inside the patient room. In this way, stationary controller 152 may be tasked with monitoring wristband interaction in order to identify a person entering the room and stationary controller 196 may be tasked with monitoring wristband interaction in order to identify a person exiting the room. Further, the stationary controller network (e.g., such as a stationary controller positioned at respective patient rooms, or multiple stationary controllers positioned at respective patient rooms) may perform multiple tasks, such as monitoring a healthcare provider entering/exiting room, and also monitoring the trace of each provider.

In still an alternate implementation, one or more movements associated with entering or exiting the patient area may be detected. As discussed herein, one or more motion sensors may detect movement of a movable item, such as a door opening and/or a door closing. The door may move in one of several ways, such as swinging open/closed or sliding open/closed. In one implementation, the wristband may sense movements (such as using the accelerometer and/or gyroscope housed therein) in order for the wristband to analyze the sensed movement in order to determine whether a door has been opened or a door has been closed (e.g., swing open or swung closed; slid open or slid closed). In an alternate implementation, an electronic device, separate from the wristband and the stationary controller, may sense the movements and may determine whether the door has opened or closed. In this regard, responsive to the one or more motion sensors sensing a door opening, the one or more motion sensors may transmit a communication (such as a near-field Bluetooth communication) indicative that a door opening has been sensed, which may be received by one or both of the wristband and the stationary controller. Responsive to receipt of the communication indicative that a door opening has been sensed, the wristband and/or the stationary controller may determine that the healthcare provider is entering the room. Conversely, responsive to the one or more motion sensors sensing a door closing, the one or more motion sensors may transmit a communication (such as a near-field Bluetooth communication) indicative that a door closing has been sensed, which may be received by one or both of the wristband and the stationary controller. Responsive to receipt of the communication indicative that a door closing has been sensed, the wristband and/or the stationary controller may determine that the healthcare provider is exiting the room. Alternatively, the separate electronic device may transmit the sensed movements in order for the wristband and/or stationary controller to make the determination.

Alternatively, in the instance where the door is on a spring (and automatically closes after opening), the one or more motion sensors may still output indications of door openings/closings (e.g., sensor outputs indicative of door opening closing in quick succession).

In the instance where a separate sensor detects the door opening/closing and transmits the indication of the door opening/closing, responsive to receipt of the communication indicative that a door has opened or closed, the wristband and/or the stationary controller may determine whether the indication is for an entrance or an exit. For example, responsive to the wristband determining that the indication of entrance/exit has not been received within 1 minute (meaning that the wristband has not received an indication within 1 minute of any opening/closing of a door), the wristband may determine that the healthcare provider is entering the room. Conversely, responsive to the wristband determining that the indication of entrance/exit has been received within 1 minute, the wristband may determine that the healthcare provider is exiting the room.

FIG. 2 is another example block diagram of a HH and/or PPE system 200, with mobile wristband device 210 and local stationary controller 230 communicating wirelessly 120 with one another. As shown, HH and/or PPE system 200 does not include a back-end server. Rather, all analytics discussed herein are performed by one or both of the mobile wristband device 210 and the local stationary controller 230.

Figure 3A:
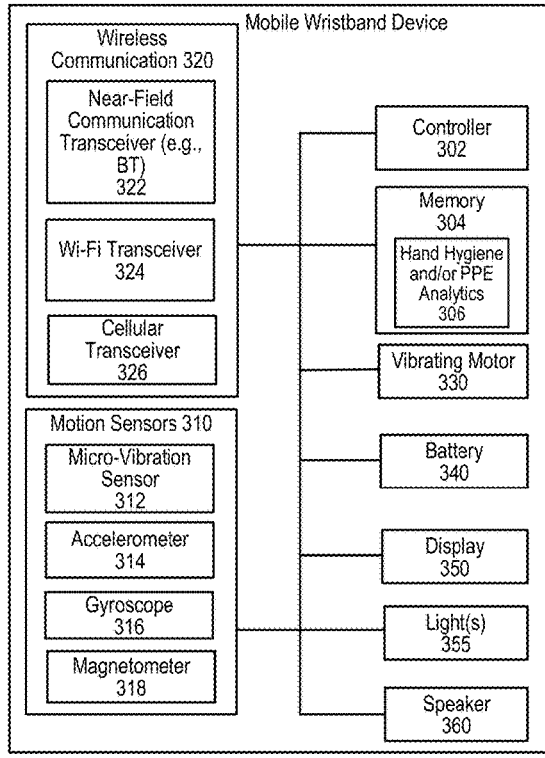
FIG. 3A is a first example block diagram of the mobile wristband device.

FIG. 3A is a first example block diagram of the mobile wristband device 300. As illustrated, the mobile wristband device 300 may include a controller 302, a memory 304, motion sensor(s) 310, wireless communication 320, vibrating motor 330, battery 340, display 350, light(s) 355, and speaker 360. The components illustrated in FIG. 3A may be housed in a mechanical structure that is configured to be attached to a wrist. For example, the mechanical structure may be in the form of a bangle or the like. In one implementation, all of the elements depicted in FIG. 3A are incorporated into the wristband. Alternatively, fewer than all of the elements depicted in FIG. 3A are incorporated into the wristband. For example, vibrating motor 330, display 350, light(s) 355, speaker 360, fewer than all of the motion sensors 310 and fewer than all of the wireless communication 320 need be included in the wristband.

Mobile wristband device 300 may be used in any one of FIG. 1A-D or 2. The controller 302 may comprise a microprocessor, a microcontroller/DSP, PLA, or the like. Further, the memory 304 may include software, such as hand hygiene and/or PPE analytics 306, and may include storage for storing data from motion sensor(s) 310. Thus, memory 304 may be configured for: (1) HH analytics; (2) PPE analytics; or (3) both HH and PPE analytics. FIG. 3A illustrates multiple motion sensors. In one implementation, a single motion sensor is used. Thus, in one implementation, mobile wristband device 300 includes only a single motion sensor, such as only accelerometer 314 or only gyroscope 316. Alternatively, multiple motion sensors may be used include any two, any three, or any four of the following: micro-vibration sensor 312, accelerometer 314, gyroscope 316, or magnetometer 318. In an alternative implementation, mobile wristband device 300 includes multiple sensors, such as both accelerometer 314 and gyroscope 316.

In addition, wristband device 300 includes wireless communication 320. In one implementation, a single wireless communication protocol is used. Alternatively, multiple wireless communication protocols may be used include any two, any three, or any four of the following: One or more near-field communication transceiver 308 may comprise functionality to communicate in any one, any combination, or all of the following: near-field communication transceiver 322 (e.g., Bluetooth, RFID, and ZigBee); Wi-Fi transceiver 324; cellular transceiver 326; or other far-field communication.

Figure 3B:
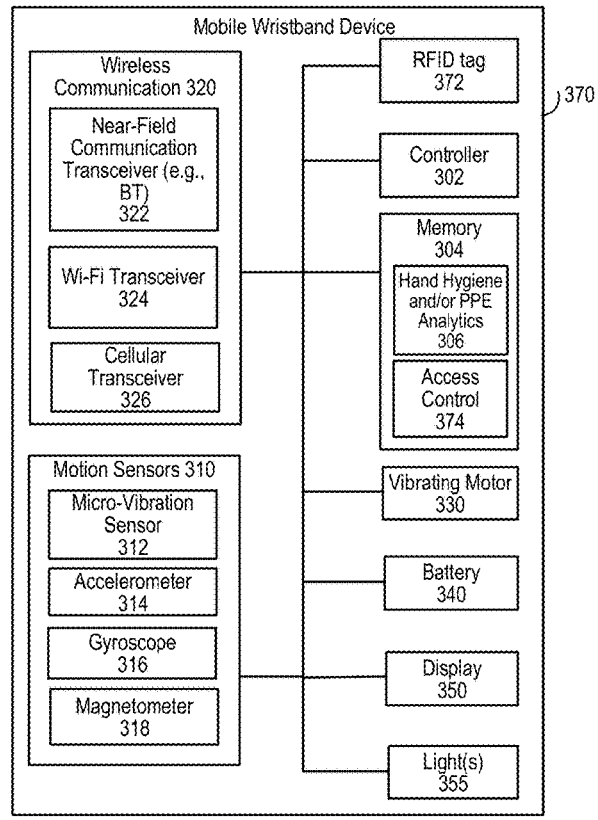
FIG. 3B is a second example block diagram of the mobile wristband device.

FIG. 3B is a second example block diagram of the mobile wristband device 370. Wristband device 370 has functionality similar to wristband device 300, with the additional functionality of access control. In particular, wristband device 370 may be used in combination with an RFID access control system and includes RFID tag 372. Further, wristband device 370 includes access control 374, which may be used to provide additional access control functionality to wristband device 370, as discussed further below.

Figure 3C:
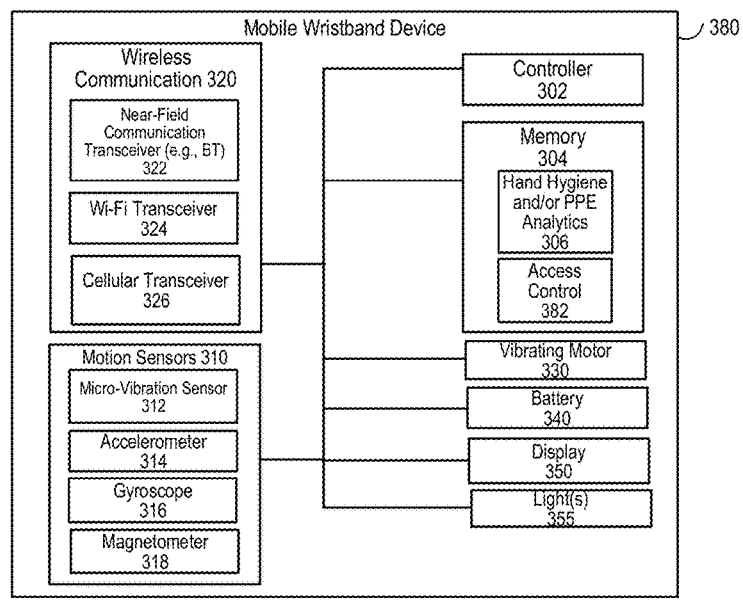
FIG. 3C is a third example block diagram of the mobile wristband device.

FIG. 3C is a third example block diagram of the mobile wristband device 380. Wristband device 380 has functionality similar to wristband device 300, with the additional functionality of access control. In particular, wristband device 380 may be used in combination with an access control system that uses a communication method included in wireless communication 320 (such as using near-field communication transceiver 322). In this regard, the identification code associated with the user of wristband 380 need not be stored in RFID tag 372, but may be stored in access control 382 (or other memory resident in wristband device 380). Further, wristband device 380 includes access control 382, which may be used to provide additional access control functionality to wristband device 380, as discussed further below.

FIG. 4A is a first example block diagram of local stationary controller 400. As illustrated, local stationary controller 400 may include a controller 402, a memory 404, one or more communication protocols, such as near-field communication transceiver 308, and a far-field communication transceiver (such as Wi-Fi transceiver 408 or cellular transceiver (not shown), proximity sensor 410, sound sensor 412, speaker 414, light(s) 416, and display 418. In one implementation, all of the elements depicted in FIG. 4A are incorporated into the stationary controller. Alternatively, fewer than all of the elements depicted in FIG. 4A are incorporated into the wristband. For example, proximity sensor 410, sound sensor 412, speaker 414, light(s) 416, display 418 need be included in the stationary controller.

Local stationary controller 400 may be used in any one of FIG. 1A-D or 2. The controller 402 may comprise a microprocessor, a microcontroller/DSP, PLA, or the like. Further, the memory 404 may include software, such as analytics 406 (e.g., HH analytics, PPE analytics, or HH and PPE analytics). As discussed above, analytics of the motion sensor data may be performed by the mobile wristband device and/or by the local stationary controller. Further, near-field communication transceiver 308 may be used to communicate via one or more near-field protocols with mobile wristband device. As discussed above, examples of near-field communication protocols include, but are not limited to Bluetooth, RFID, and ZigBee. Other near-field communication protocols are contemplated. Further, local stationary controller 400 may communicate with a back-end server, such as back-end server 130 or cloud computing E.

As discussed further below, in one implementation, stationary controller 400 may sense the proximity of the user (such as the provider). In a specific implementation, stationary controller 400 may sense the proximity of the wristband worn by the user. Proximity sensor 410 is a representation of the functionality to sense the proximity of the wristband worn by the user. As discussed herein, stationary controller 400 may sense a communication signal, such as a received signal strength indicator (RSSI) signal, which is an example of sensing the proximity of an electronic device. The stationary controller 400, via proximity sensor 410 or the like, may sense the RSSI signal of the wristband at being greater than a predetermined amount or strength (e.g., indicating that the wristband is within 1 meter, within 2 meters, within 3 meters, etc.) for at least a predetermined amount of time (e.g., at least 1 second, at least 2 seconds, at least 3 seconds, etc.) in order to determine whether the wristband is proximate to the stationary controller 400. Alternatively, or in addition, stationary controller 400 may determine which RSSI signal has the highest signal strength in order to predict which wristband is closest.

Further, as discussed below, sound sensor 412 may be used in order to sense sounds, such as sounds generated by dispenser 151 or sounds generated by user. Speaker 414, light(s) 416, and display 418 may be used as means for output of information to the user.

FIG. 4B is a second example block diagram of the local stationary controller 430. Stationary controller 430 is similar to stationary controller 400, with the addition of access control 434. As discussed further below, access control may comprise additional functionality that may be performed by stationary controller 430, such as illustrated in FIGS. 5A-J.

Further, as discussed above, the wristband and stationary controller may interact with one another during various times of a HH and/or PPE action and/or a HH and/or PPE opportunity. As discussed further below with regard to the flow charts, the following may comprise a sequence of interaction that includes any one, any combination, or all of: (1) proximity sensing of the stationary controller relative to and wristband or vice-versa in order to identify a HH and/or PPE opportunity; (2) generation of output on one or both of the stationary controller or the wristband to indicate the HH and/or PPE opportunity; (3) sensing whether hand cleaning agent has been dispensed (e.g., the stationary controller reviewing audio sensor data to determine whether the motor on the dispenser has dispensed the hand cleaning agent); (4) waking up part of the wristband responsive to determining that the hand cleaning agent has been dispensed (e.g., stationary controller sends a signal to wake-up the microcontroller and/or the accelerometer and/or gyroscope); (5) the awakened motion sensors generate sensor data; (6) the sensor data is analyzed to determine whether certain hand motions, indicative of sufficient hand hygiene, are detected in order to determine whether there is compliance with hand hygiene protocols; and (7) the sensor data is analyzed to determine whether certain hand motions, indicative of putting on or removing PPE garment(s), are detected in order to determine whether there is compliance with PPE protocols.

As discussed above, in one or some embodiments, one or more actions may trigger the HH and/or PPE action, such as proximity to a dispenser, entrance into a room, or the like. Alternatively, other actions, such as an action as part of the HH and/or PPE action, may trigger the event, such as the dispensing of hand cleaning agent. In such embodiments, other actions, such as entrance into the room or the like, may be identified as opportunities to interact with the patient.

Figure 6A:
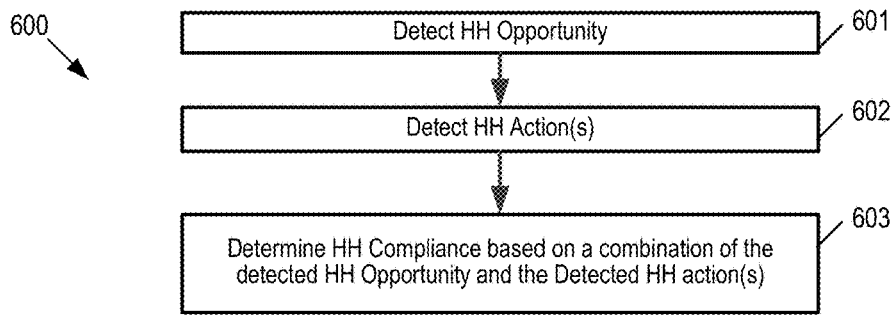
FIG. 6A is a flow diagram for detecting both the HH opportunity and the HH action and determining HH compliance based on a combination of the detected HH opportunity and the HH action.

FIG. 6A is a flow diagram 600 of detecting both the HH opportunity and the HH action(s) and determining HH compliance based on a combination of the detected HH opportunity and the HH action(s). At 601, the HH opportunity is detected. At 602, the HH action(s) are detected. As discussed above, the HH opportunity may be detected before detecting the HH action(s) (e.g., entering the room and then taking sanitizer). Conversely, the HH opportunity may be detected after detecting the HH action(s) (e.g., taking sanitizer in the hallway before entering the room; taking sanitizer in the hallway before exiting the room). Thus, while flow diagram 600 depicts detecting the HH opportunity before detecting the HH action, the converse may be true.

Further, at 603, HH compliance is determined based on a combination of the detected HH opportunity and the detected HH action(s). As discussed above, in one or some embodiments, the HH action (such as the detection of and/or determined compliance with the HH action(s)) is sufficiently connected to the HH opportunity in order for the compliance with the HH action(s) to be associated with or assigned to the HH opportunity. Discussed in more detail below in FIGS. 6B and 8A, the determination of compliance may be based on whether there is sufficient connection (such as connection in time) between the detected HH action(s) and the detected HH opportunity.

Figure 6B:
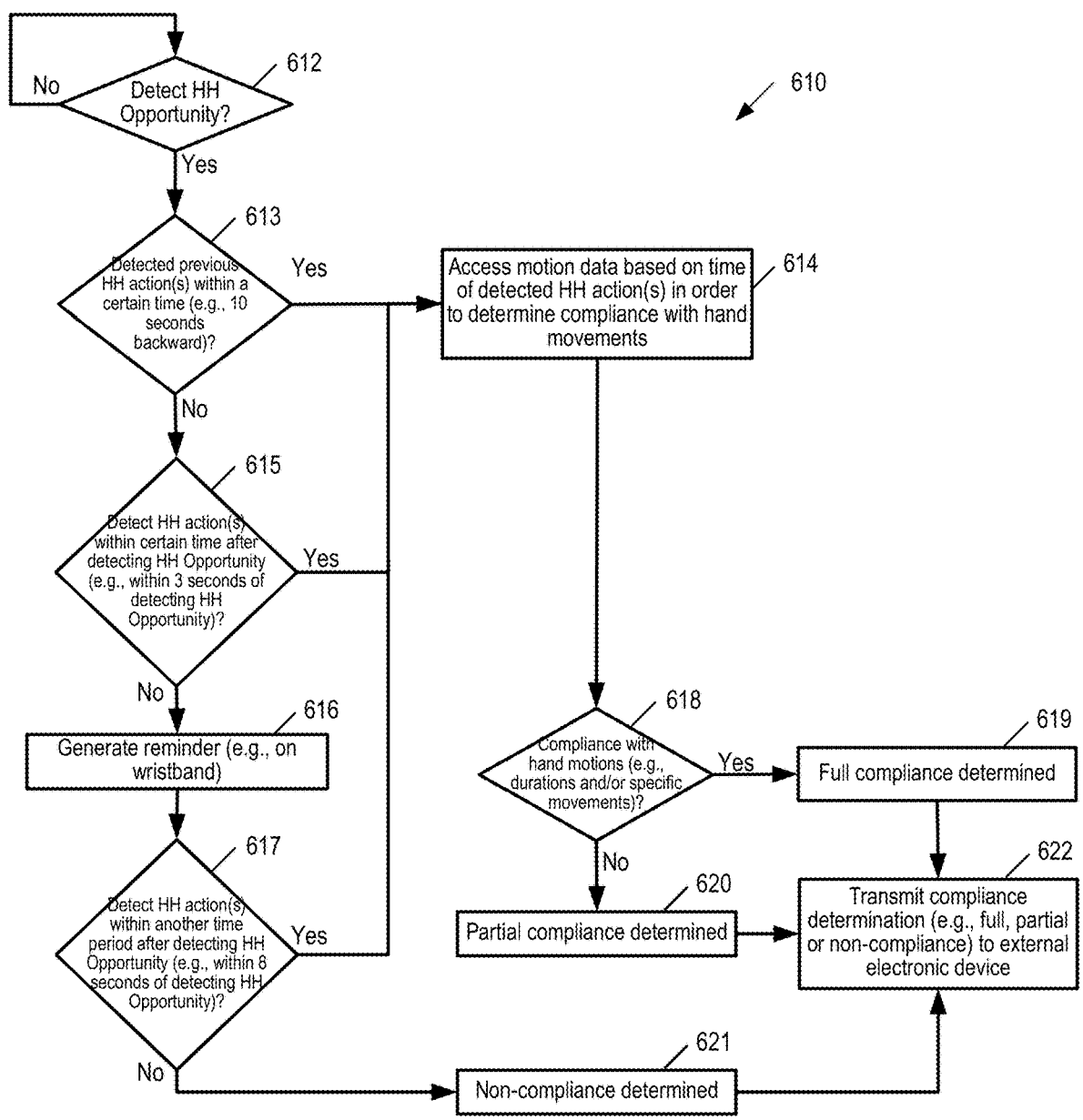
FIG. 6B is a flow diagram of one example of determining whether there is sufficient connection between the detected HH action and the detected HH opportunity.

FIG. 6B is a flow diagram 610 of one example of determining whether there is sufficient connection between the detected HH action and the detected HH opportunity. At 612, it is determined whether there is a HH opportunity detected. As discussed above, various ways are contemplated to detect the HH opportunity, including based on tracking movement of the healthcare provider. Further, various devices are contemplated to detect the HH opportunity, including one or both of the wristband or the stationary controller.

Responsive to detecting a HH opportunity (at 612), at 613, it is determined whether a HH action has previously been detected within a certain time period. For example, this is illustrated in FIG. 6C, which shows a time window 626 for the start of a qualified HH action. As discussed above, various qualified actions are contemplated, including, for example, one or both of taking hand cleaning agent or performing hand movements. In this regard, any discussion herein regarding closeness (in time and/or in space) of a hygiene action to an opportunity, various actions, including taking hand cleaning agent and/or performing hand movements, may be analyzed for closeness to the opportunity. Specifically, 627 is the furthest time of detecting dispensing hand cleaning agent from detecting the HH opportunity 628 (e.g., 10 seconds) while still qualifying the HH action as being sufficiently tied to the HH opportunity. Otherwise, the detected HH opportunity 628 is considered too remote (such as too remote in time) to be a qualifying HH action for purposes of determining compliance with a HH opportunity.

If at 613 it is determined that the HH action was detected within a certain time, at 614, the motion data (such as stored in the wristband) may be accessed based on time of detected HH action in order to determine compliance with hand movements. As discussed above, responsive to the stationary controller detecting the HH action (e.g., detecting dispensing of hand cleaning agent), the stationary controller may send a message to wristbands proximate to the stationary controller (e.g., in the dispensing messaging zone). Responsive thereto, the wristband may wake up and begin detecting and/or analyzing hand movements. Thus, prior to determination of a HH opportunity, the wristband already may have stored motion data based on when the HH action has been detected, with the trigger (such as the communication from the stationary controller) focusing the wristband's analysis of the stored motion data (e.g., the wristband selects the motion data for analysis based on its time stamp so that the motion data analyzed for compliance begins at, or approximately begins at, the time at which the communication is received from the stationary controller).

If at 613 it is determined that the HH action was not detected within a certain time, at 615, it is determined whether the HH action was or will be detected within a certain time of detecting the HH opportunity. For example, this is illustrated in FIG. 6C at 629 as a certain period (e.g., 3 seconds). If the HH action has not been detected at 615 (e.g., no dispensing of hand cleaning agent detected), at 616, a reminder may be generated. For example, in one or some embodiments, if the stationary controller does not detect a dispensing of hand cleaning agent within the certain period (e.g., 3 seconds), the stationary controller may generate an output (such as an auditory output on a speaker associated with the stationary controller and/or visual output on a light associated with the stationary controller) reminding the healthcare provider to take hand cleaning agent. Alternatively, or in addition, the stationary controller may send a message to wristbands (such as in the dispensing messaging zone, discussed herein) indicating to the wristbands to generate the reminder output (such as an auditory output on a speaker resident on the wristband and/or visual output using a light resident on the wristband). Still alternatively, responsive to the wristband identifying the HH opportunity, and if in 3 seconds after identifying the HH opportunity, the wristband fails to receive a communication from a stationary controller, indicating dispensing of hand cleaning agent has occurred, the wristband may generate the reminder output. In one or some embodiments, responsive to receiving the message from the stationary controller, the wristband generates the reminder output regardless of the status of the healthcare provider. Alternatively, responsive to receiving the message from the stationary controller, the wristband determines whether to generate the reminder output dependent on the status of the healthcare provider (e.g., the status (e.g., trainee or non-trainee) of the healthcare provider may be stored in the wristband; responsive to receiving the reminder message from the stationary controller, the wristband determines to generate the reminder output responsive to identifying the healthcare provider wearing the wristband as a trainee and determines not to generate the reminder output responsive to identifying the healthcare provider wearing the wristband as a non-trainee). Still alternatively, no reminder (such as reminder 629) need be issued.

At 617, it is determined whether the HH action was detected within another time period after detecting the HH opportunity. For example, this is illustrated in FIG. 6C at 630 as a certain period (e.g., 5 seconds from the reminder 629). Thus, in one embodiment, the amount of time looking backward from detecting the HH opportunity is different from the amount of time looking forward from detecting the HH opportunity (e.g., 10 seconds versus 8 seconds). Alternatively, the amount of time looking forward and backward from detecting the HH opportunity may be the same. It is noted that the figures illustrate detecting the HH opportunity and then determining whether a HH action is proximate (such as in time or space). Alternatively, the HH action may first be detected and then it may be determined whether a HH opportunity is proximate.

In the event that the HH action has not been detected within the time period, at 621, non-compliance is determined. For example, if it is determined that there has been no dispensing of hand cleaning agent within a certain time period of detecting the HH opportunity, it may then be determined that there is no compliance with the HH opportunity. In one or some embodiments, the stationary controller may determine this non-compliance. Alternatively, the wristband, in combination with receiving a communication from proximate stationary controller(s), may determine this non-compliance. Still alternatively, the wristband, identifying the HH opportunity and failing to receive a communication with the certain time period from the stationary controller indicating dispensing of hand cleaning agent, determines there is no compliance with the HH opportunity.

At 618, compliance with hand motions (e.g., durations and/or specific movements) may then be determined. For example, as discussed above, one or both of duration and/or specific movements may be monitored by the wristband in order to determine compliance. If so, at 619, full compliance is determined. For example, the wristband, responsive to reviewing the motion data stored thereon, may determine whether the motion data is indicative of compliance. If not, at 620, partial compliance may be determined. As discussed above, partial compliance may be based on several criteria including: taking hand cleaning agent but not complying with hand motions; or taking hand cleaning agent and only partially complying with hand motions (e.g., complying with duration but not with specific hand motions; complying with duration and partially complying with specific hand motions).

At 622, the compliance determination may be transmitted. As discussed above, HH actions may be insufficiently tied to a HH opportunity. In that regard, merely focusing on determining compliance for HH actions (without sufficient connection to an identified HH opportunity) may be misplaced. Rather, in one or some embodiments, one, some or all of transmission, recordal, or tagging of compliance with HH actions may be dependent on sufficient connection to the identified HH opportunity. As one example, responsive to determining that the HH action is not sufficiently connected to the identified HH opportunity, no transmission of the compliance determination (e.g., compliance, partial-compliance or non-compliance) with the detected HH action is made. In particular, without the connection of the HH action to the identified HH opportunity, the compliance determination is not transmitted external to the wristband and/or the stationary controller so that the back-end servers have no knowledge thereof (e.g., no knowledge of a detected HH action or of compliance with the detected HH action). As another example, responsive to determining that the HH action is not sufficiently connected to the identified HH opportunity, the results of compliance, partial-compliance or non-compliance may be transmitted (with an indication that the HH action is not sufficiently connected to any identified HH opportunity), but that the back-end server may treat the results differently than if the results were tied to an identified HH opportunity (e.g., the back-end server may decide not to record the results or may decide to record the results but to tag the compliance determination to indicate that the results are not sufficiently connected to any identified HH opportunity). In this way, in one or some embodiments, hand hygiene results may be more focused on the identified HH opportunities, which are typically the focus, rather than more generally relating to compliance with detected HH actions.

As shown, FIG. 6B begins by determining whether a HH opportunity has been detected, and thereafter checking either forward or backward in time whether the HH action has been detected. Conversely, the flow may comprise determining whether a HH action has been detected, and thereafter checking either forward or backward in time whether the HH opportunity has been detected, as discussed above.

Figure 8A:
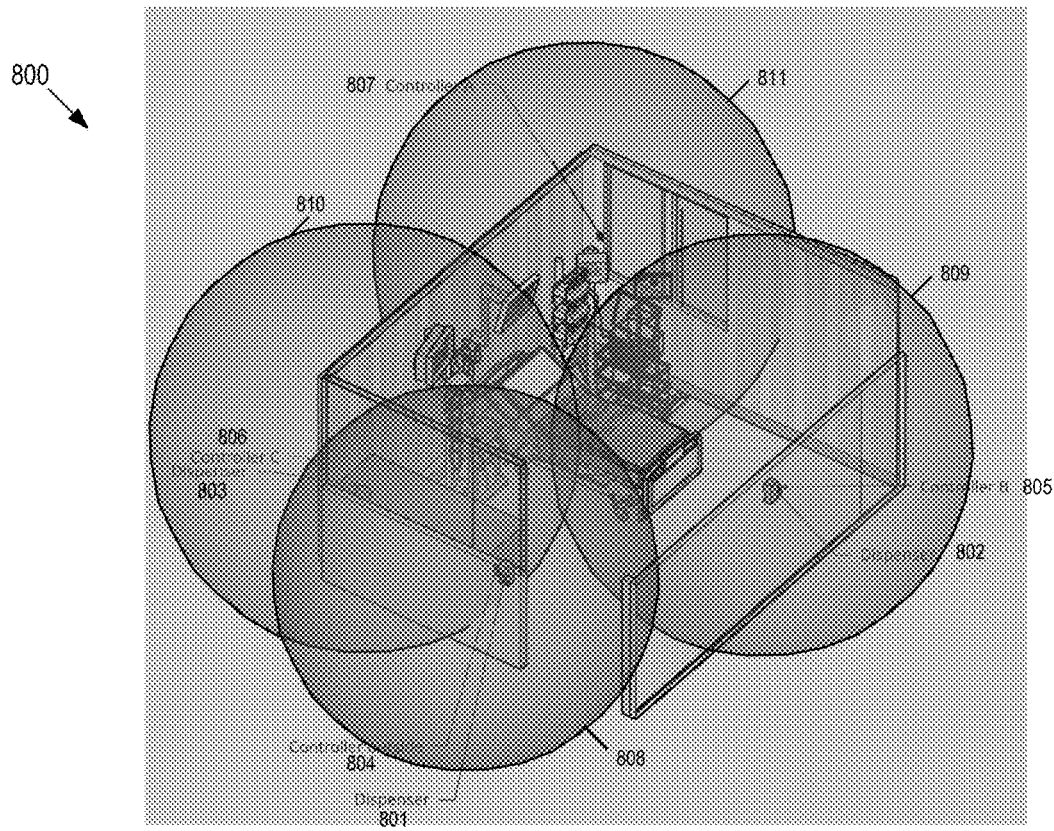
FIG. 8A illustrates a 3-D perspective view of a patient room with a plurality of communication zones.

As discussed above, tracking movement of the healthcare provider may be performed in one of several ways. As one example, communication(s) with the wristband of the healthcare provider may be used to track the movement of the healthcare provider, as illustrated in FIG. 8A. In particular, FIG. 8A is a perspective view 800 of one example of an area (e.g., a patient room), with a plurality of stationary controllers (controller outside 804 of patient room, controller A 807, controller B 805, controller C 806) and associated communication zones 808, 811, 809, 810. As shown in FIG. 8A, some of the controllers are associated with a respective dispenser, such as dispenser 801 associated with controller outside 804, dispenser 802 associated with controller B 805, and dispenser 803 associated with controller C 806. As one example of tracking, communication with a single controller (and more particularly communication with a single controller for at least a predetermined amount of time) may be indicative of tracking movement of the healthcare provider. In particular, communication of the mobile electronic device with controller outside 804 for at least 1.5 seconds may be indicative that the healthcare worker is planning to enter the patient area. Alternatively, communication of the mobile electronic device with controller B 805 for at least 1.5 seconds may be indicative that the healthcare worker has already entered the patient area. As another example of tracking, communication with multiple controllers (and more particularly communication with the multiple controllers for at least a predetermined amount of time) may be indicative of tracking movement of the healthcare provider. In either instance, the mobile electronic device, itself, may (using communication with stationary controller(s)) make the determination as to the tracking of movement of the healthcare provider the mobile electronic device is associated with. As discussed above, the controller may be associated with a respective dispenser in one of several ways, such as being integrated with or proximate to the respective dispenser. Further, a controller, such as controller A 807, need not be associated with a respective dispenser.

Thus, it is noted that the time period between a previous HH action determination and a subsequent HH opportunity determination may vary depending on whether PPE is required for the patient room. For example, in compliance only with the HH protocol, FIG. 6B (at 613) and FIG. 6C (between 627 and 628) have a span of 10 seconds between detecting the HH action and detecting the subsequent HH opportunity, discussed below. However, in the event that the patient room requires PPE, 10 seconds may not be sufficient to comply with the HH protocol, comply with the PPE protocol (e.g., by putting on PPE) and also enter the room. Thus, in one or some embodiments, the time period between the HH action determination and the subsequent HH opportunity may be dynamic, such as dependent on whether there is another protocol (separate from hand hygiene) to follow, such as to follow a PPE protocol.

FIG. 6D is a second timing diagram 632 for determining whether there is sufficient connection between the detected HH action and the detected HH opportunity in which multiple communications from the stationary controller are received before the detected opportunity. As discussed above, a wristband may receive multiple communications from a stationary controller indicating that a hygiene action (such as a dispensing event) has occurred. The wristband may, in turn, perform one or both of: (i) predicting whether the action was performed by the person wearing the wristband; and (ii) determine whether the action is sufficient close (such as in time) to be associated with the detected hygiene opportunity for purposes of hygiene compliance with the opportunity. With regard to (i), as discussed above, responsive to receiving the communication from the stationary controller, the wristband may determine whether there is movement within a certain time period. If so, the wristband predicts that the person associated with the wristband performed the action (e.g., took the sanitizer) and then determines whether the action (as indicated by the time at which the communication from the stationary controller was received) is sufficient close in time to be attributed to the detected hygiene opportunity. As shown in FIG. 6D, the wristband receives two separate communications at 633 and at 634, each indicating that hand cleaning agent has been dispensed. For each of communications 633 and 634, a window of time (e.g., shown as 3 seconds) is set to determine whether motion has been sensed by the wristband. As shown in FIG. 6D, no motion is sensed within the 3 seconds from communication 633, whereas motion is sensed on the wristband within the 3 second from communication 634. As such, the wristband predicts that communication 634, for purposes of determining closeness to the detected hygiene opportunity, is attributed to the person wearing the wristband, meaning that the time when communication 634 was received is used to determine closeness to the detected hygiene opportunity. As shown in FIG. 6D, if the detected hand hygiene opportunity 628 is within a certain period of communication 634 (such as within 10 seconds of communication 634), then the taking of hand cleaning agent (indicated by communication 634 and attributed to the wristband due to the detected motion within 3 seconds of communication 634) is attributed to the detected hand hygiene opportunity 628. Though not shown, it is possible for motion to be sensed within 3 seconds of communication 633. If so, the time when communication 633 was received is used to determine closeness to the detected hygiene opportunity.

FIG. 6E is a third timing diagram 640 for determining whether there is sufficient connection between the detected HH action and the detected HH opportunity in which multiple communications from the stationary controller are received after the detected opportunity. As shown in FIG. 6E, the wristband receives two separate communications at 641 and at 642, each indicating that hand cleaning agent has been dispensed. For each of communications 641 and 642, a window of time (e.g., shown as 3 seconds) is set to determine whether motion has been sensed by the wristband. As shown in FIG. 6E, motion is sensed within the 3 seconds from communication 641, whereas motion is sensed on the wristband within the 3 second from communication 634. As such, the wristband predicts that communication 641, for purposes of determining closeness to the detected hygiene opportunity, is attributed to the person wearing the wristband, meaning that the time when communication 641 was received is used to determine closeness to the detected hygiene opportunity. As shown in FIG. 6E, if the detected hand hygiene opportunity 628 is within a certain period of communication 634 (such as within 10 seconds of communication 641), then the taking of hand cleaning agent (indicated by communication 641 and attributed to the wristband due to the detected motion within 3 seconds of communication 641) is attributed to the detected hand hygiene opportunity 628. Though not shown, it is possible for motion to be sensed within 3 seconds of communication 642. If so, the time when communication 642 was received is used to determine closeness to the detected hygiene opportunity. FIG. 6E further illustrates time period 643 (shown as 3 seconds) after detecting opportunity 628. In the event that there is no indication of the hygiene action taken within time period 643 (such as no receipt of communication 641 or 642 with the 3 seconds after detecting opportunity 628, one or both of the stationary controller or the wristband may generate an output (such as an aural output) in order to remind the wearer of the wristband to take sanitizer.

Figure 6F:
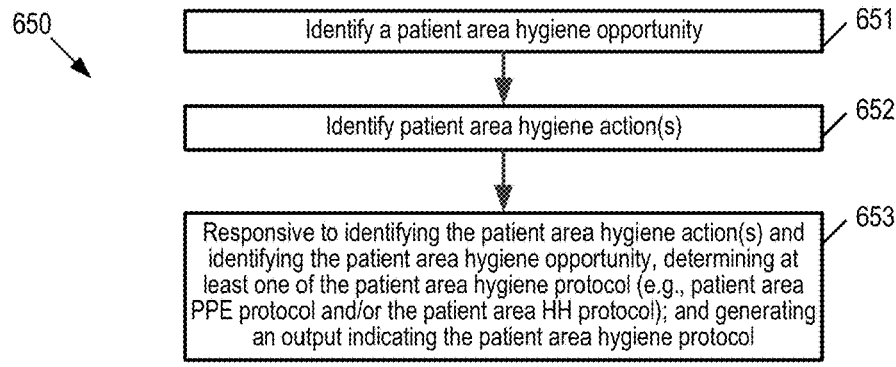
FIG. 6F is a flow diagram for identifying a patient area hygiene opportunity, identifying a patient area hygiene action, and determining whether and what to output regarding protocol(s) responsive to identifying the patient area hygiene opportunity and patient area hygiene action.

FIG. 6F is a flow diagram 650 of identifying an area hygiene opportunity, identifying an area hygiene action, and determining whether and what to output regarding protocol (s) responsive to identifying the area hygiene opportunity and area hygiene action. As discussed above, the healthcare provider may be notified regarding one or more protocols associated with a patient area. This notification may be provided either in conjunction with monitoring compliance (e.g., monitoring HH compliance with HH protocol(s) and/or PPE compliance with PPE protocol(s)). Alternatively, the notification may be provided separate from any monitoring compliance. In this regard, any discussion herein regarding notification may be performed in conjunction with compliance determination or may not be performed in conjunction compliance determination. As discussed above, notification may be opportunity-based. Specifically, healthcare providers may be constantly inundated with notifications of compliance with various protocols. In order to minimize the number of notification while still providing notification when believed necessary, an opportunity-based notification is provided in which notification occurs responsive to identifying an opportunity for patient interaction (such as the 5 WHO opportunities discussed above). Thus, at 651, a patient area hygiene opportunity (such as one or both of a HH opportunity or a PPE opportunity) is identified. As discussed above, various ways to identify a patient area hygiene opportunity are contemplated. At 652, a patient area hygiene action (such as one or both of a HH action or a PPE action) is identified. As discussed above, various ways to identify a patient area hygiene action are contemplated (e.g., detecting dispensing of hand cleaning agent; detecting removing of PPE; etc.). At 653, responsive to identifying the patient area hygiene action(s) and identifying the patient area hygiene opportunity: determining at least a part of the patient area hygiene protocol (e.g., the patient area hygiene protocol includes one or both of the patient area PPE protocol or the patient area HH protocol); and generating an output indicating at least a part of the patient area hygiene protocol (e.g., at least one of the patient area PPE protocol or the patient area HH protocol). As discussed above, one or more protocols, such as one or both of a HH protocol or a PPE protocol may be associated with a patient area, such as a patient room. As such, responsive to identifying the patient area hygiene action(s) and identifying the patient area hygiene opportunity, the protocol(s) associated with the patient area may be determined (e.g., using the stationary controller associated with the patient area, which has stored therein the protocol(s) and/or communicating with a back-end server, which includes a database correlating patient areas with corresponding protocol(s)). Further, at least one aspect of the protocol(s) may be output. As one example with regard to HH, the type of hand cleaning agent to use, such as either soap or hand sanitizer, may be output. As another example with regard to PPE, the type of PPE garments (e.g., only gloves; only a mask and gloves; etc.) may be output. Alternatively, the sequence of PPE to put on, such as first the mask and then the gloves, may be output. Still alternatively, in combination with monitoring the movements of the healthcare provider, the outputs may track the sequence (e.g., in the example of putting on a mask and gloves, the wristband may monitor the movements for putting on a mask; after confirmation that the healthcare provider has performed the movements for putting on the mask, the wristband may generate an output to put on the gloves). Yet alternatively, the sequence of HH and PPE may be output (e.g., when entering the patient area, the wristband may output: "first wash hands with soap, and then put on a mask and gloves"; when exiting the patient area, the wristband may output: "first remove gloves and then mask, and then wash hands with soap"). Or, the output may be dynamic based on the tracked movements (e.g., when entering the room, the wristband may monitor hand movements for hand washing; after confirmation that the healthcare provider has performed the movements for washing hands, the wristband may generate an output indicative of "now put on the mask and then the gloves"). Though FIG. 6F illustrates identifying the patient area hygiene opportunity prior to identifying the patient area hygiene action(s), the converse may be true.

Figure 6G:
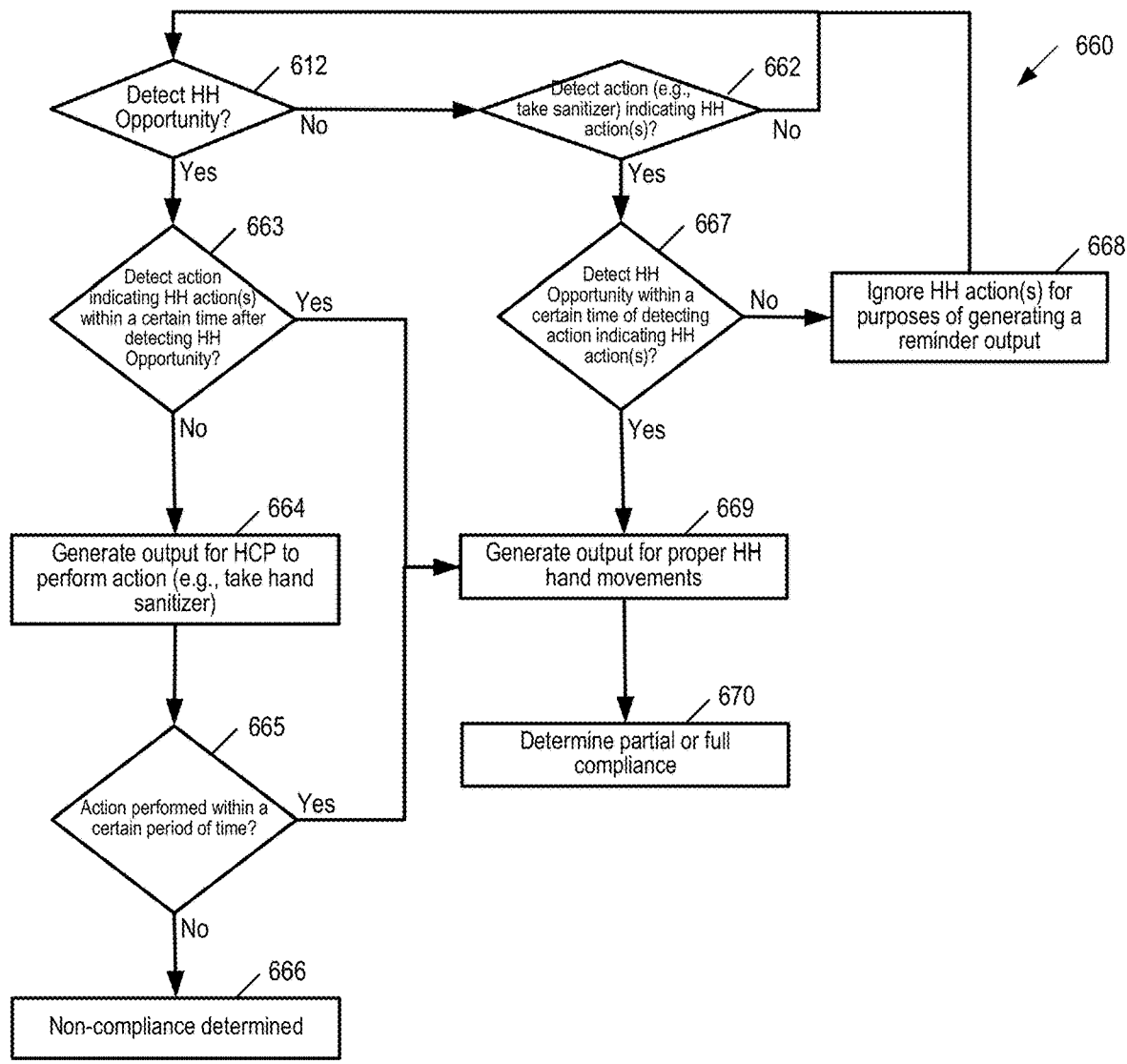
FIG. 6G is a flow diagram for determining whether to generate reminder outputs for HH protocol(s) and what outputs to generate for the HH protocols when detecting a HH opportunity.

FIG. 6G is a flow diagram 660 of determining whether to generate reminder outputs for HH protocol(s) and what outputs to generate for the HH protocols when detecting a HH opportunity. At 612, it is determined whether the HH opportunity is detected. For example, the wristband may determine whether there is movement either into or out of the patient area. If yes, at 663, it is determined whether an action indicating the HH action has occurred within a certain time after detecting the HH opportunity (e.g., the time period between 628 and 629 in FIG. 6C or time period 643 in FIG. 6E). As one example, an action may comprise the healthcare provider taking hand cleaning agent from a dispenser. If not, at 664, an output may be generated for the healthcare provider (HCP) to perform the action (e.g., take hand sanitizer). This output is illustrated at 629 in FIG. 6C. If so, flow diagram 660 moves to 669.

At 665, it is determined whether the action (e.g., taking hand sanitizer) has been performed with a certain time period (such as the time period between 629 and 630 of 5 seconds). If not, at 666, one or both of the wristband or the stationary controller may determine non-compliance. If so, flow diagram 660 moves to 669.

If at 612 no HH opportunity is detected, the system (such as the stationary controller) may determine whether an action has been detecting indicating a HH Action (such as taking hand sanitizer). If not, flow diagram loops back to 612. If so, at 667, the system determines whether a HH opportunity has been detected or identified within a certain time of detecting the action indicating the HH action. If not, at 668, the HH action is ignored for purposes of generating a reminder output. If so, at 669, an output, such as via one or both of the wristband or the stationary controller, may be generated for proper HH movements (e.g., one or both of an indication of the amount of time, such as 20 seconds of rubbing, or the proper sequence of hand movements). After which, at 670, partial or full compliance with the HH opportunity is determined.

Figure 6H:
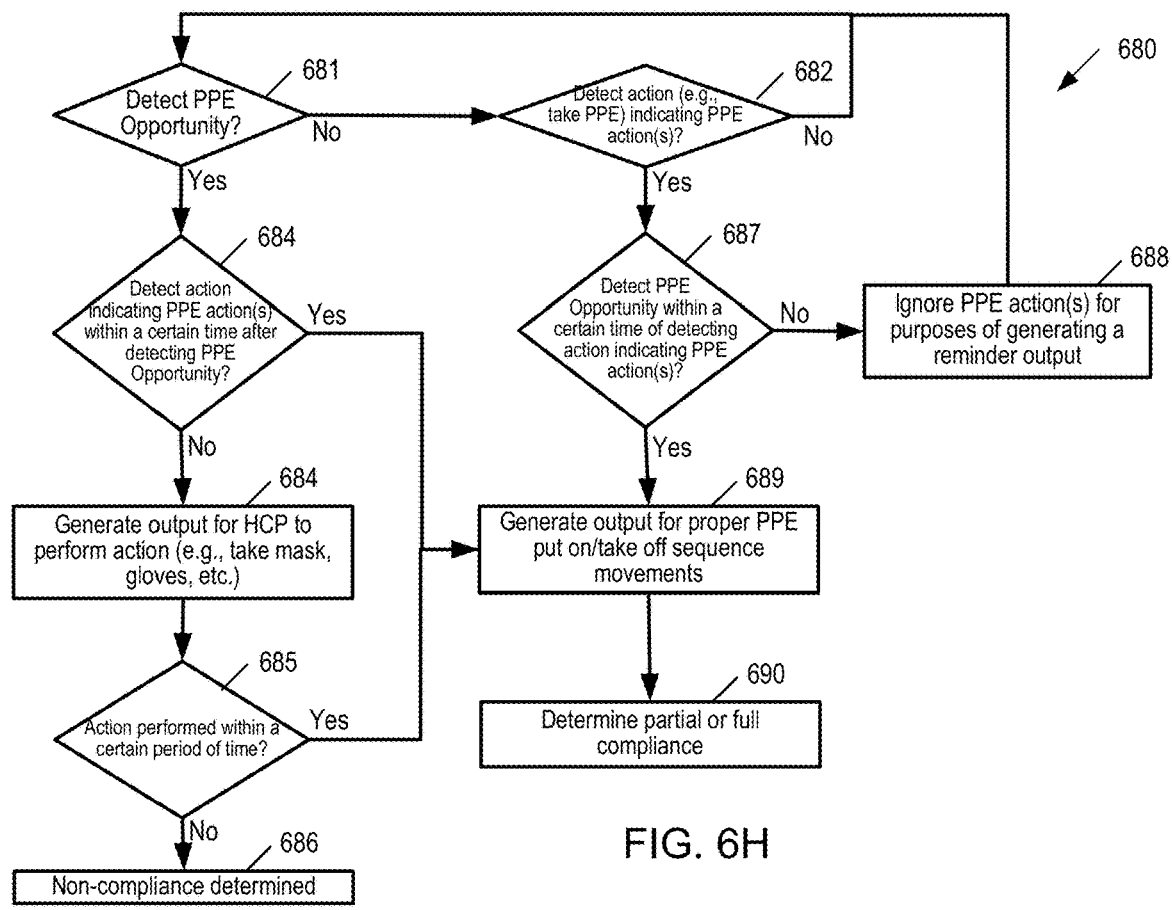
FIG. 6H is a flow diagram for determining whether to generate reminder outputs for PPE protocol(s) and what outputs to generate for the PPE protocols when detecting a PPE opportunity.

FIG. 6H is a flow diagram 680 of determining whether to generate reminder outputs for PPE protocol(s) and what outputs to generate for the PPE protocols when detecting a PPE opportunity. At 681, it is determined whether a PPE opportunity has been detected. For example, the wristband may determine whether there is movement either into or out of the patient area. If yes, at 684, it is determined whether an action indicating the PPE action has occurred within a certain time after detecting the HH opportunity. As one example, an action may comprise the healthcare provider taking PPE from a PPE container. If not, at 684, an output may be generated for the healthcare provider (HCP) to perform the action (e.g., take PPE). If so, flow diagram 680 moves to 689.

At 685, it is determined whether the action (e.g., taking PPE) has been performed with a certain time period. If not, at 686, one or both of the wristband or the stationary controller may determine non-compliance. If so, flow diagram 680 moves to 689.

If at 681 no PPE opportunity is detected, the system (such as the stationary controller) may determine whether an action has been detecting indicating a PPE Action (such as taking PPE). If not, flow diagram 680 loops back to 681. If so, at 687, the system determines whether a PPE opportunity has been detected or identified within a certain time of detecting the action indicating the PPE action. If not, at 688, the PPE action is ignored for purposes of generating a reminder output. If so, at 689, an output, such as via one or both of the wristband or the stationary controller, may be generated for proper PPE movements (e.g., proper sequence of PPE to put on or take off). After which, at 690, partial or full compliance with the PPE opportunity is determined.

As discussed herein, a patient area may have associated therewith a patient area protocol, such as a HH protocol and/or a PPE protocol. The patient area protocol may be dynamically assigned, such as based on a diagnosis associated with the patient. For example, the patient, upon admittance to a specific hospital room, may already have been diagnosed with a MRSA infection. As such, the specific hospital room may be assigned the HH protocol and/or a PPE protocol for treating a MRSA infection. Alternatively, after the patient was admitted to the specific hospital room, the patient may thereafter have been infected, such as having been infected with a MRSA infection. Thus, the specific hospital room may have its associated protocol be dynamically changed from a first patient area protocol to a second patient area protocol, with the second patient area protocol being different from the first patient area protocol (e.g., prior to being diagnosed with a MRSA infection, the specific hospital room has assigned a non-MRSA infection protocol; after being diagnosed with the MRSA infection, the specific hospital room has assigned a MRSA infection protocol). In this way, the various patient areas in a hospital, nursing home, or other healthcare environment may dynamically change its protocols based on changed circumstances.

In order to assist the healthcare providers in awareness of the changing patient area protocols, the system may identify a patient area hygiene opportunity, and responsive to identifying the patient area hygiene opportunity, intelligently determine whether to generate an output to remind the healthcare provider. In this way, reminders may be kept to a minimum, thereby being less intrusive to the healthcare provider, while still being used when a patient area hygiene opportunity is identified.

Figure 6I:
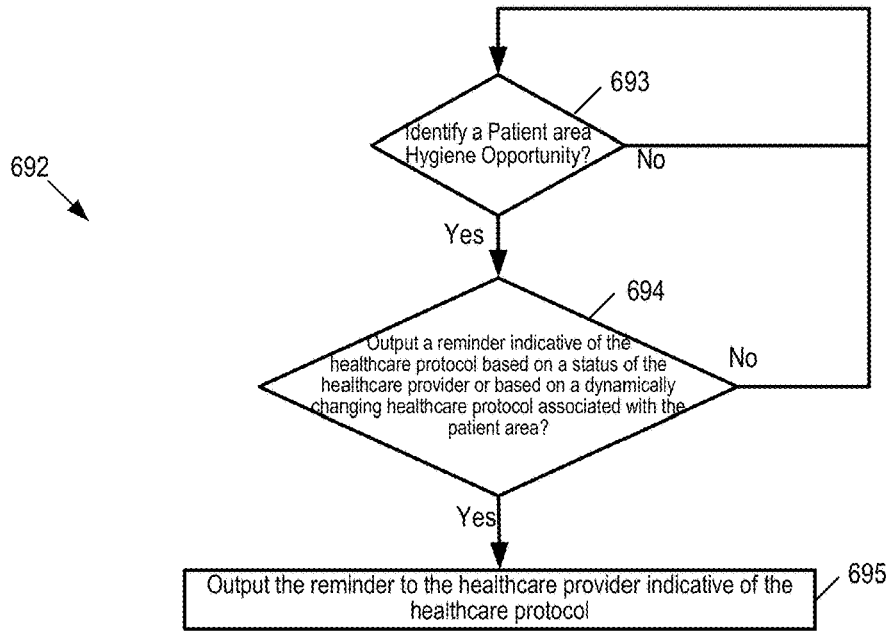
FIG. 6I is a flow diagram for identifying a patient area hygiene opportunity associated with a patient area and determining whether to generate a reminder indicative of the healthcare protocol associated with the patient area.

One example of the intelligent reminder system is illustrated in the flow diagram 692 in FIG. 6I for identifying a patient area hygiene opportunity associated with a patient area and determining whether to generate a reminder indicative of the healthcare protocol associated with the patient area. At 693, it is determined whether a patient area hygiene opportunity is present, such as an opportunity associated with a specific patient room. As discussed above, the patient area hygiene opportunity may be indicative of interaction of the healthcare provider with a patient in the patient area. Further, various hygiene opportunities are contemplated, such as one or both of a HH opportunity or a PPE opportunity.

Responsive to not identifying the patient area hygiene opportunity, flow diagram 692 loops back to 693. Responsive to identifying the patient area hygiene opportunity, at 694, it is determined whether to output a reminder indicative of the healthcare protocol associated with the patient area. As discussed above, several ways are contemplated to associate a healthcare protocol with a patient area. The association may be performed at the server level, and may be dynamically accessed at the server level (e.g., one or both of a mobile electronic device or a local stationary controller (positioned in or about the patient area) may dynamically access the healthcare protocol on a server). The association may be performed at the server level, and may be dynamically accessed at the patient area level (e.g., the healthcare protocol may be sent (e.g., pushed or pulled) from the server to a local stationary controller positioned in or about the patient area; a mobile electronic device, when proximate to the local stationary controller, may communicate with the local stationary controller to determine the healthcare protocol). Still alternatively, the association may be performed at the patient area level, and may be dynamically accessed at the patient area level (e.g., the local stationary controller may be programmed with the healthcare protocol and may dynamically access the healthcare protocol (and/or send the healthcare protocol to a proximate mobile electronic device). Yet alternatively, the association and the access may be at the mobile electronic device level (e.g., the mobile electronic device locally stores patient area rooms (with associated location coordinates and associated healthcare protocols); the mobile electronic device, using its GPS receiver, determines its current location determines the patient area closest to its current location, and accesses the associated healthcare protocol for the determined patient area).

Further, various bases to determine whether to output the reminder are contemplated. One manner to determine whether to output the reminder is based on a status of the healthcare provider (e.g., responsive to determining that the healthcare provider is a trainee, output the reminder; responsive to determining that the healthcare provider is not a trainee, decide not to output the reminder). Another manner to determine whether to output the reminder is based on a dynamically changing healthcare protocol associated with the patient area based on a diagnosis of the patient in the patient area. For example, a protocol associated with the patient area may dynamically change based on the diagnosis of the patient associated with the patient area (e.g., the patient is diagnosed with a MRSA infection). In one particular manner, in deciding whether the protocol has dynamically changed, the healthcare provider may interact with the patient area at a current time, it may be determined whether one or both of the PPE protocol or the HH protocol associated with the patient area has changed within a predetermined time period prior to the current time, and if so, the reminder indicative of the healthcare protocol may be output. In this regard, responsive to identifying that the patient area has a dynamically changing protocol and/or that the protocol has been changed within in a certain time period (e.g., the protocol has changed within the past week), it is determined to output the reminder.

Responsive to determining to output the reminder, at 695, the reminder is output to the healthcare provider indicative of the healthcare protocol. Responsive to determining not to output the reminder, flow diagram 692 loops back to 693. Further, in order to avoid an excessive number of reminders, even though the patient area has a dynamically changing protocol and/or that the protocol has been changed within a certain time period, the system, under certain circumstances, may determine not to output the reminder. As one example, responsive to outputting the reminder a certain set number of times, such as a certain number of times for a specific healthcare provider, for a group of healthcare providers, etc., no further reminders are given.

Figure 7A:
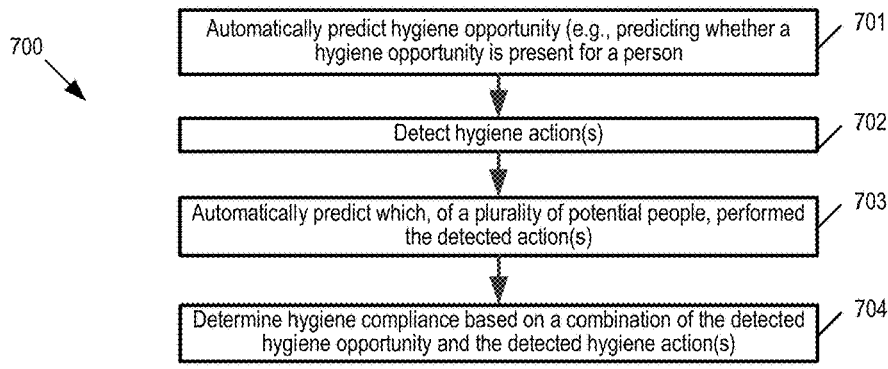
FIG. 7A is a flow diagram of predicting a hygiene opportunity and which person performed a detected hygiene action.

As discussed above, the system (including one or both of the stationary controller or the wristband) may predict which, from a plurality of potential people, perform a hygiene action. This prediction may be performed separate from any hygiene opportunity determination or prediction. Alternatively, this prediction may be performed in combination with a hygiene opportunity determination or prediction. FIG. 7A is a flow diagram 700 of predicting a hygiene opportunity and which person performed a detected hygiene action. At 701, a hygiene opportunity is automatically predicted. For example, a wristband may predict whether a hygiene opportunity is present for a person. At 702, one or more hygiene actions are detected. As discussed above, various ways are contemplated to detect hygiene actions, such as via one or both of the stationary controller or the wristband. At 703, a device, such as one or both of the stationary controller or the wristband, automatically predicts which, of a plurality of potential people, performed the detected action(s). As discussed above, various ways are contemplated to predict which of the plurality of people performed the detected action(s). For example, any one, any combination, or all of data generated by the wristband, data generated by the stationary controller, communication data between the stationary controller and the wristband, or data generated by sensors in an area (e.g., UV or IR sensors in the patient area) may be analyzed in order to make the prediction. Merely by way of example, the stationary controller may determine a location of the wristband relative to the stationary controller based on the strength of the communication signals. As discussed above, in one or some embodiments, the stationary controller may determine a closest wristband (e.g., based on the RSSI signal with the greatest strength) and predict that the person wearing the closest wristband took the sanitizer. Alternatively, the stationary controller may determine the wristbands that are in a zone around the stationary controller, such as a designated hand hygiene zone, (e.g., based on signal strengths or based on communications with wristbands, such as RSSI is at least 60 dB). In response to the stationary controller determining that only one wristband is in the designated zone, the stationary controller may determine that the person wearing the one wristband took the sanitizer. In response to the stationary controller determining that there are multiple wristbands in the designated zone, the stationary controller may send a communication to the wristbands in the designated zone, with the wristbands performing further analysis (such as analyzing the hand movement data) to predict which wristband took the hand cleaning agent. Alternatively, multiple stationary controllers (positioned within or proximate to the patient area, such as in FIGS. 8A-C) may be used to predict whether person with a specific wristband performed the hygiene action. At 704, hygiene compliance is determined based on a combination of the detected hygiene opportunity and the detected hygiene action(s).

Figure 7B:
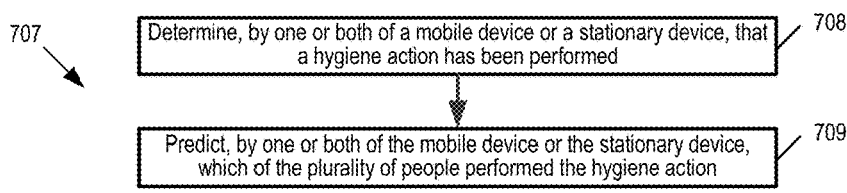
FIG. 7B is a flow diagram of one example of predicting which person performed a detected hygiene action.

FIG. 7B is a flow diagram 707 of one example of predicting which person performed a detected hygiene action. At 708, one or both of the mobile device (e.g., the wristband) or the stationary device determines or detects that a hygiene action has been performed. At 709, one or both of the mobile device or the stationary device predict which of the plurality of people performed the hygiene action.

Figure 7C:
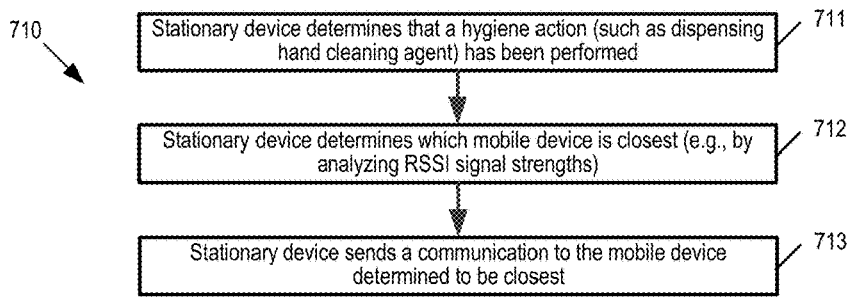
FIG. 7C is a flow diagram of one example of a stationary controller-centric prediction in which the stationary controller predicts which person performed a detected hygiene action.

FIG. 7C is a flow diagram 710 of one example of a stationary controller-centric prediction in which the stationary controller predicts which person performed a detected hygiene action. At 711, the stationary device determines that a hygiene action (such as dispensing hand cleaning agent) has been performed. At 712, the stationary device determines which mobile device is closest (e.g., by analyzing RSSI signal strengths). At 713, the stationary device sends a communication to the mobile device determined to be closest (with the person who is wearing the closest mobile device presumed to have performed the hygiene action).

Figure 7D:
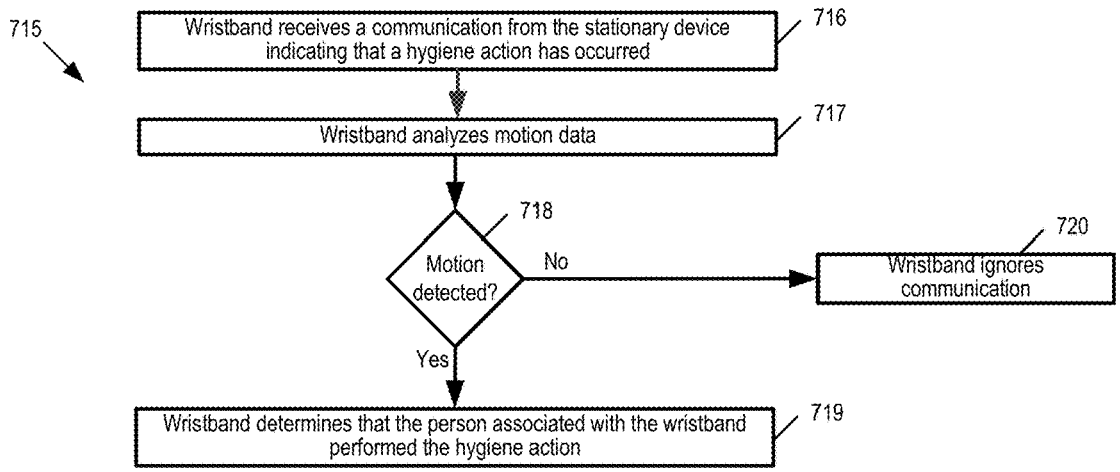
FIG. 7D is a flow diagram of one example of a wristband-centric prediction in which the wristband predicts which person performed a detected hygiene action.

FIG. 7D is a flow diagram 715 of one example of a wristband-centric prediction in which the wristband predicts which person performed a detected hygiene action. In one embodiment (illustrated in FIG. 7D), the wristband performs the wristband-centric prediction independently of other wristbands. Alternatively, the wristband may perform the wristband-centric prediction at least partly dependent of other wristbands (e.g., a respective wristband may receive the RSSI signal strength from one or more other wristbands proximate to the stationary controller in order for the respective wristband to determine whose RSSI signal is strongest). At 716, the wristband receives a communication (such as a broadcast communication) from the stationary device indicating that a hygiene action has occurred. Optionally, motion sensor(s) on the wristband may be awaked from sleep mode in response to receipt of the communication. At 717, the wristband analyzes motion data generated by a motion sensor resident on the wristband. At 718, it is determined, based on analysis of the motion data, whether hand motion is detected (thereby indicating potential rubbing of hand sanitizer or hand soap). If yes, at 719, the wristband determines that the person associated with the wristband performed the hygiene action. If not, at 720, the wristband ignores the communication received at 716.

Thus, the figures illustrate various systems for identifying and determining compliance of a worker, such as one or both of predicting a hygiene opportunity or predicting who performed hygiene action(s). The systems may include one or more electronic devices, such as only the wristband, only the stationary controller, or both the wristband and the stationary controller, that may be configured to: automatically detect a hygiene opportunity, the hygiene opportunity indicative of interaction for which compliance is to be monitored, the compliance requiring one or more hygiene actions; automatically detect at least one action, the at least one action comprising at least one of the one or more hygiene actions; automatically determine whether at least one criterion associated with the at least one action is within a criterion amount of the hygiene opportunity; and automatically determine compliance or non-compliance with the hygiene opportunity dependent on automatically determining whether the at least one action is within the criterion amount of the hygiene opportunity. As one example, a first mobile electronic device (e.g., the wristband) may be configured to automatically detect the hygiene opportunity and a second stationary electronic device (e.g., the stationary controller) may be configured to automatically detect the at least one action. As another example, a single electronic device (e.g., the wristband) may automatically detect the hygiene opportunity and automatically predict which of a plurality of people performed the at least one action. As still another example, a first electronic device (e.g., the wristband) may automatically detect the hygiene opportunity and a second electronic device (e.g., the stationary controller) may automatically predict which of a plurality of people performed the at least one action. Still alternatively, the predictions of the opportunity and/or who performed hygiene action(s) may be performed in multiple stages, such as with an initial prediction (e.g., an initial prediction of a hygiene opportunity and/or an initial prediction of who performed a hygiene action) and then a confirmation (or rejection) of the initial prediction. In one or some embodiments, the initial predication and the confirmation may be performed by different devices (e.g., initial prediction performed by the wristband using tracking data generated by the wristband and the confirmation performed by the stationary controller (which is associated with a specific area) using data generated by the stationary controller, such as dispensing data). Alternatively, the initial predication and the confirmation may be performed by the same electronic device.

The identification of the patient area hygiene opportunity and/or the determination as to whether to output the reminder indicative of the patient area healthcare protocol may be performed by the same device or, alternatively, may be performed by different devices. In one embodiment, the mobile electronic device may identify the patient area hygiene opportunity and determine whether to output the reminder indicative of the patient area healthcare protocol. For example, the mobile electronic device may communicate with an external device, such as the stationary controller and/or the backend server in order to determine whether the patient area healthcare protocol associated with the patient area is dynamically changeable (e.g., determine whether the protocol associated with the area indicates a dynamically changing protocol; determine whether the protocol has changed within a certain time period; etc.). Alternatively, separate devices may identify the patient area hygiene opportunity and determine whether to output the reminder indicative of the patient area healthcare protocol. For example, the mobile electronic device may identify the healthcare opportunity and a backend server determines whether to cause an output of the reminder. Specifically, the backend server may: responsive to identifying a healthcare opportunity for a healthcare worker to interact with the patient associated with the patient area, access a database storing the patient area healthcare protocol associated with the patient area that is dynamically changeable; and cause an output to be generated, the output indicative to the healthcare worker of the patient area healthcare protocol (e.g., send a command so that one or both of the mobile electronic device or the stationary controller outputs the indication of the patient area healthcare protocol). Still alternatively, the stationary controller may be programmed with the protocol (which may be changed) and also may be programmed with a time window in which to output reminders. Responsive to interaction with a wristband in near-field communication range of the stationary controller and responsive to the stationary controller determining that a current time is within the time window, the stationary controller may output the reminder and/or may send a command to the wristband to output the reminder.

FIG. 8A illustrates communication zones 808, 811, 809, 810, with some communication zones 808, 811, 809, 810 in one embodiment at least partially overlapping one another. Alternatively, the communication zones do not overlap one another at all. Thus, each sphere in FIG. 8A represents a communication zone 808, 811, 809, 810 for a respective controller (controller outside 804, controller A 807, controller B 805, controller C 806). In one or some embodiments, the size (e.g., distance from an electronic device to the stationary controller) of each zone may be programmed by setting a threshold for the Received Signal Strength Indicator (RSSI) values obtained from the wristbands. Thus, the wristband may receive a signal from an external electronic device, such as a respective stationary controller, and determine a zone relative to the external electronic device.

In one or some embodiments, multiple zones, such as three zones, may be programmed for each controller. However, fewer or greater numbers of zones are contemplated. As one example, the following three zones comprise: (1) connection zone; (2) a dispensing messaging zone; and (3) a proximity zone. Specifically, a respective stationary controller may connect to all wristbands in its respective connection zone. Further, in the example of three zones, the connection zone may be set as the largest (e.g., ~15-20 ft). When a respective stationary controller detects a dispensing event (e.g., on the dispenser the respective stationary controller monitors), the respective stationary controller sends one or more messages (e.g., a dispensing message) to all wristbands in the dispensing messaging zone. As discussed in more detail below, this dispensing message triggers the determination of HH action compliance. For example, responsive to a wristband receives the dispensing message and the wristband determining (based on the RSSI value) that the wristband is within the dispensing messaging zone, the wristband starts the HH detection algorithm to determine compliance with one or both of duration of hand rubbing or detection of specific hand movements. In this way, rather than the wristband constantly attempting to review its movements to determine compliance, the wristband may have a trigger (such as based on the wristband receiving the dispensing message from the stationary controller and the wristband determining the wristband received the dispensing message within the dispensing message zone) that allows the wristband to focus its analysis of hand movements and/or duration on a time period for the HH action. Further, the wristband may receive "pings" from the stationary controller (e.g., messages at predetermined intervals), with the wristband determining whether the RSSI signal for the "pings" indicating that the wristband is within the proximity zone. In one or some embodiments, the proximity zone is smaller than the dispensing message zone (e.g., 3-5 feet). Alternatively, the proximity zone is larger than the dispensing message zone.

As discussed above, the location and/or movement of the healthcare provider may be used to identify a HH opportunity. Thus, in one or some embodiments, the electronic device (such as a wristband) associated with the healthcare provider, may determine the movement of the healthcare provider (and in turn identify the HH opportunity). For example, wristbands in the proximity zone may be considered very close to the respective stationary controller. Thus, when a wristband enters/exits a proximity zone of the respective stationary controller, the wristband may receive a "ping" from the respective stationary controller and determine from the signal strength of the "ping" that the wristband is within the proximity zone. In this way, the wristband may determine its location and or associated movement, and then the wristband may determine if there is a hand hygiene opportunity. Thus, in one or some embodiments, communication zones 808, 811, 809, 810 each comprise a proximity zone for the respective controller. Alternatively, at least one of the communication zones 808, 811, 809, 810 is different (such as in size) from another of the communication zones 808, 811, 809, 810.

As one example, the wristband may determine movement from outside of a patient area to an interior of the patient area. In a specific implementation, a first stationary controller (such as controller outside 804) is positioned at the entrance of a specific patient area and a second stationary controller (controller A 807, controller B 805, or controller C 806) is positioned in an interior of the specific patient area. In moving from outside of the specific patient area to the inside, the first stationary controller (such as controller outside 804) may send a "ping" to the wristband (with the "ping" from the first stationary controller indicating that it is a message from an electronic device on the exterior of the specific patient area). In turn, the wristband determines that the wristband is within the proximity zone of the first stationary controller that is on the exterior of the specific patient area. As the healthcare provider moves to the interior of the specific patient room, the wristband receives the "ping" from the second stationary controller (controller A 807, controller B 805, or controller C 806) (with the "ping" from the second stationary controller indicating that it is a message from an electronic device in the interior of the specific patient area) and determines that the wristband is within the proximity zone of the zone stationary controller that is in the interior of the specific patient area. Thus, from the series of pings, the wristband may determine movement from outside to inside the patient area. Alternatively, determining movement from outside to inside the patient area may comprise determination of the proximity zone (e.g., 808) with controller outside 804 and then the proximity zones (e.g., 807, 809, 810) of at least two interior controllers (e.g., at least two of controller A 807, controller B 805, controller C 806).

Conversely, the wristband may receive a sequence of pings from the second stationary controller (e.g., controller A 807, controller B 805, or controller C 806) and then from the first stationary controller (e.g., controller outside 804), indicating to the wristband that there was movement from the interior of the specific patient area to the exterior. Alternatively, determining movement from inside to outside the patient area may comprise determination of the proximity zones (e.g., 807, 809, 810) of at least two interior controllers (e.g., at least two of controller A 807, controller B 805, controller C 806) and then the proximity zone (e.g., 808) with controller outside 804. Thus, the wristband, analyzing communications with one or more external devices, such as one or more stationary controllers, may determine its respective location and/or its movement.

Figure 8B:
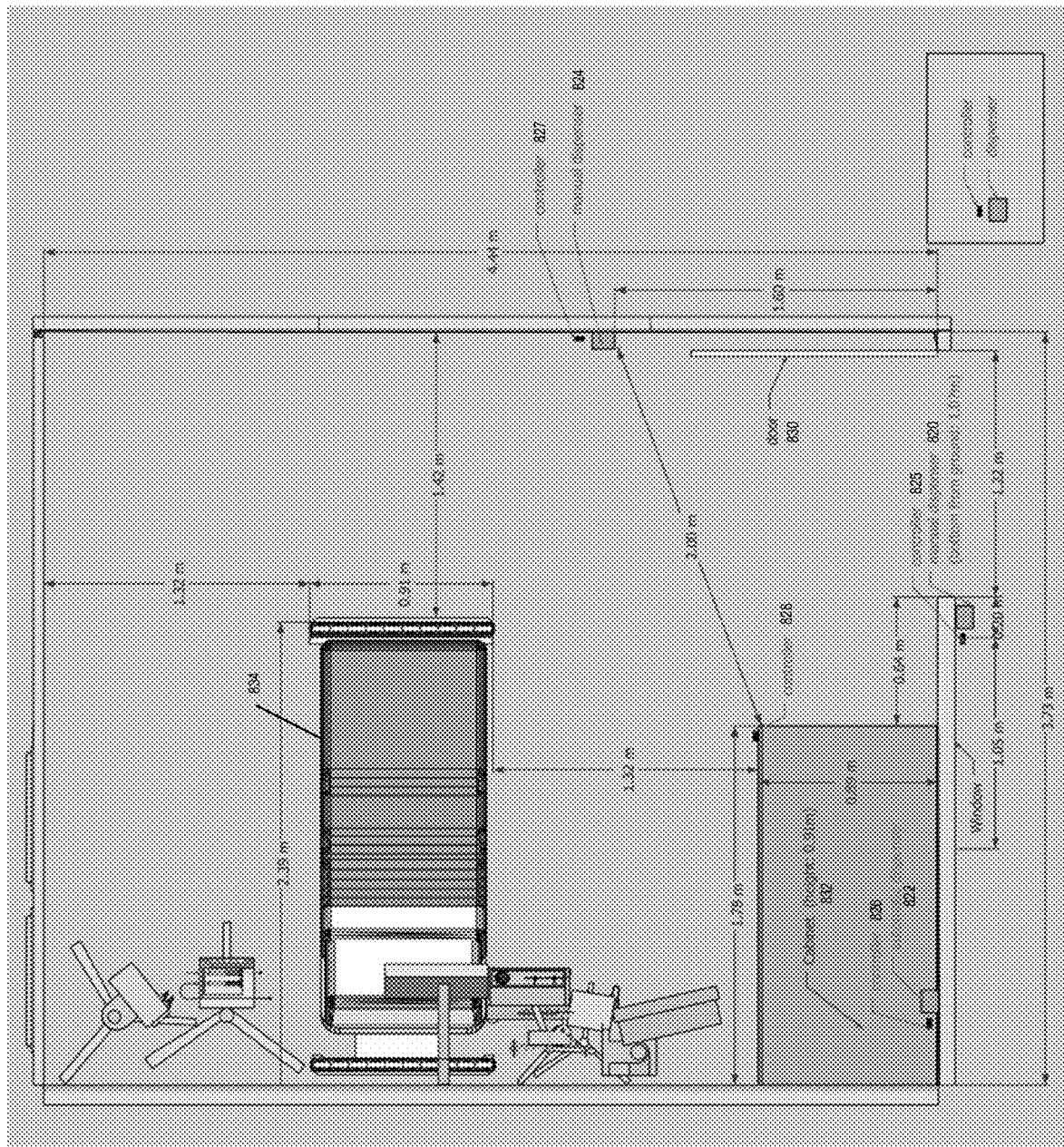
FIG. 8B illustrates a top view of a patient room with sensors and stationary controllers.

FIG. 8B illustrates a top view 818 of another example of a patient area (e.g., a patient room), with a plurality of stationary controllers 825, 826, 827, 828, associated dispensers 820, 822, 824, positioned in various areas in the patient area, such as relative to the door 830, a cabinet 832, and a bed 834. As shown, the stationary controller may be associated with dispenser (such as stationary controllers 825, 826, 827 associated with dispensers 820, 822, 824) or may not be associated with any dispenser (such as stationary controller 828). Further, placement of the stationary controllers in various locations about the patient area enables detection of the HH opportunity and the HH action, as discussed above.

Figure 8C:
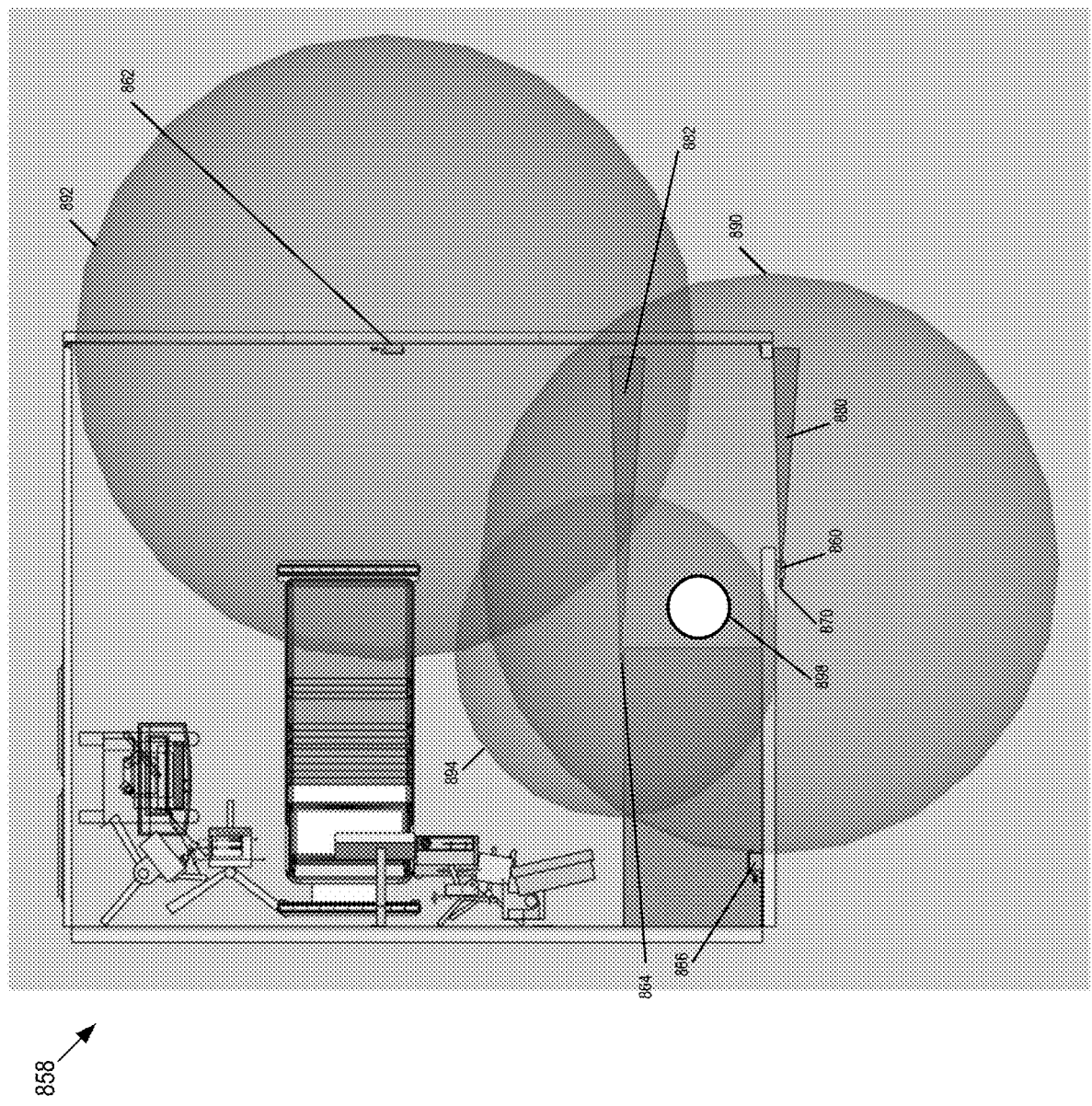
FIG. 8C illustrates a top view of a patient room with sensors, stationary controllers and communication zones.

FIG. 8C illustrates a top view 858 of yet another example of a patient area with a plurality of stationary controllers 860, 862, 864 (and associated communication zones 890, 892, 894) and one or more sensors 870. In one or some embodiments, the sensor(s) 870 may comprise ultrasonic or infrared sensors, which may be configured to measure distance from the sensor and may thus be used to determine whether there has been a transition (such as a person walking from outside of the patient area to inside of the patient area). For example, the ultrasonic or infrared sensors may comprise time-of-flight sensors that transmits a wave and senses the reflected wave to determine the time-of-flight, and in turn distance. As shown, the sensors may have an associated beam 880, 882 (with beam 882 formed by combination controller/sensor 864). Thus, as a healthcare provider crosses beams 880, 882, the sensors 870 may sense the crossing, and provide the sensor reading(s) to the associated stationary controller (such as 860, 864). In this way, based on the sensor readings, such as based on analyzing the timing of a person crossing beams 880, 882, it may be determined whether a healthcare provider is walking into or out of the patient area. For example, in one or some embodiments, the stationary controller(s) may determine, communicating with an associated ultrasonic sensor and with each other, whether the healthcare provider is walking into or out of the patient area. Further, because the stationary controller(s) communicate with the wristband of the healthcare provider (such as communicating in one of the zones, discussed above), the stationary controller(s) may identify which wristband is proximate to the stationary controller(s) when the data indicative of crossing beams 880, 882 is sensed. In one embodiment, the stationary controller(s) may identify that a respective wristband is proximate based on a momentary identification of the respective wristband within a communication zone. Alternatively, the stationary controller may require that the respective wristband be within the communication zone for a predetermined amount of time (e.g., 3 seconds) prior to identifying that the wristband is proximate (thereby avoiding someone momentarily stopping in the patient area as being identified as proximate). Alternatively, the wristband associated with the healthcare provider may receive the data indicative of crossing beams 880, 882, either directly from the ultrasonic sensors or via the stationary controller(s), and determine the movement of the healthcare provider. Further, the patient area may include a trash can 898 or some other disposal device which is located between beams 880, 882, and may be used for disposing PPE. In one or some embodiments, trash can 898 may further include a sensor (such as an ultrasonic sensor) and/or a stationary controller (for establishing communication with wristbands) in order to identify movement (such as using only its sensor readings and/or its sensor readings with other sensors such as other ultrasonic sensors or communication with other stationary controllers) into and/or out of the patient area. For example, when exiting the patient area, passing beam 882 (closer to the interior of the patient room) may trigger the start of monitoring movements to remove PPE (e.g., stationary controller may receive the sensor data from passing beam 882 identifying a crossing and, responsive thereto, send a communication to the wristband to trigger the wristband to monitor PPE movements). After which, detecting dispensing of hand cleaning agent may trigger the start of monitoring hand movements for compliance with hand hygiene (e.g., stationary controller may detect dispensing of hand cleaning agent and, responsive thereto, send a communication to the wristband to trigger the wristband to monitor HH movements).

Figure 9A:
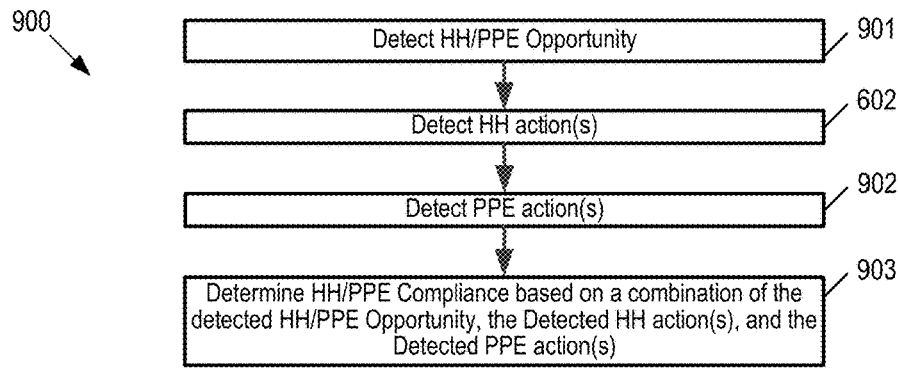
FIG. 9A illustrates is a flow diagram of detecting both the HH/PPE opportunity, the HH action, the PPE action and determining HH compliance based on a combination of the detected HH/PPE opportunity, the HH action and the PPE action.

FIG. 9A illustrates is a flow diagram 900 of detecting both the HH/PPE opportunity, the HH action, the PPE action and determining HH compliance based on a combination of the detected HH/PPE opportunity, the HH action and the PPE action. At 901, the HH/PPE opportunity is detected. At 602, the HH action is detected. At 902, the PPE action is detected. As discussed above, in one way, the PPE action may be detected on its own, such as by using the proximity sensing-output generating device. In another way, the PPE action may be detected in combination with detecting the HH action. Further, similar to the discussion above, the HH/PPE opportunity may be detected before detecting the HH action or after detecting the HH action (e.g., taking sanitizer in the hallway before entering the room). Thus, while flow diagram 900 depicts detecting the HH/PPE opportunity before detecting the HH action or the PPE action, the converse may be true.

At 903, HH/PPE compliance is determined based on a combination of the detected HH/PPE opportunity, the detected HH action, and the detected PPE action. As discussed above, in one or some embodiments, the HH action/PPE action (such as the detection of and/or determined compliance with the HH action/PPE action) is sufficiently connected to the HH/PPE opportunity in order for the compliance with the HH action/PPE action to be associated with or assigned to the HH/PPE opportunity. As discussed further below, the determination of compliance may be based on whether there is sufficient connection (such as connection in time) between the detected HH action/PPE action and the detected HH/PPE opportunity.

Figure 9C:
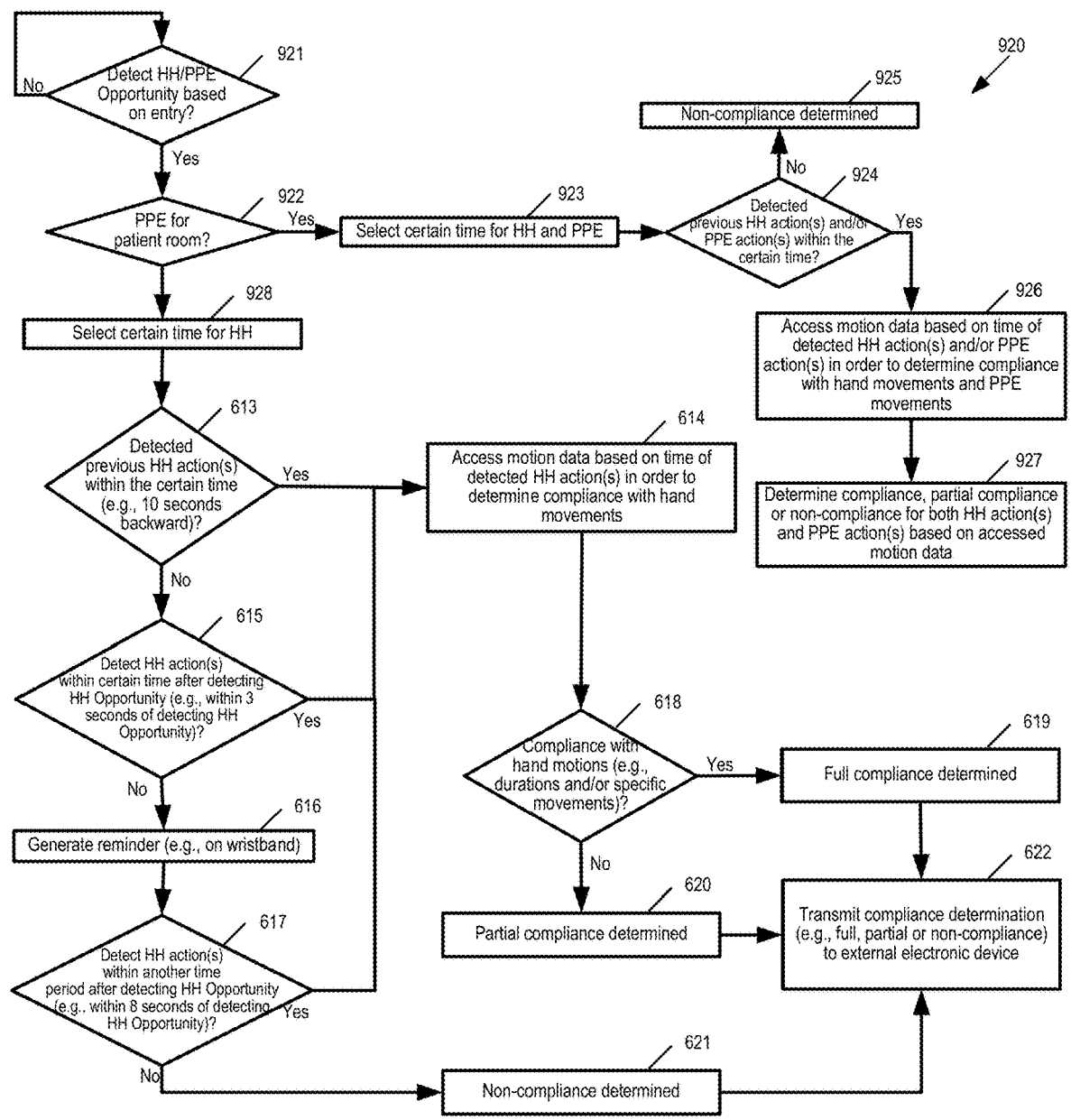
FIG. 9C is a flow diagram of one example of determining whether there is sufficient connection between the detected HH action/PPE action and the detected HH/PPE opportunity when entering a patient area.
Figure 9B:
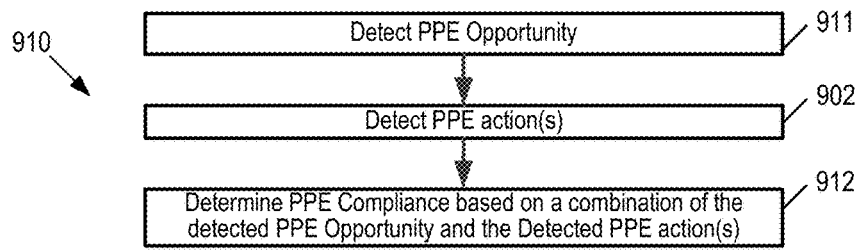
FIG. 9B illustrates is a flow diagram of detecting the PPE opportunity and the PPE action and determining compliance based on a combination of the detected PPE opportunity and the PPE action.

FIG. 9B illustrates is a flow diagram 910 of detecting the PPE opportunity and the PPE action and determining compliance based on a combination of the detected PPE opportunity and the PPE action. At 911, the PPE opportunity is detected. At 902, the PPE action is detected. At 912, PPE compliance is determined based on a combination of the detected PPE opportunity and the detected PPE action. Though flow diagram 910 depicts detecting the PPE opportunity before detecting the PPE action, the converse may be true.

FIG. 9C is a flow diagram 920 of one example of determining whether there is sufficient connection between the detected HH action/PPE action and the detected HH/PPE opportunity when entering a patient area. At 921, it is determined whether there is a HH/PPE opportunity detected on entry. As discussed above, various ways are contemplated to detect the HH/PPE opportunity, including based on tracking movement of the healthcare provider. Further, various devices are contemplated to detect the HH/PPE opportunity, including one or both of the wristband or the stationary controller.

At 922, it is determined whether there is a PPE protocol for the patient area (such as the patient room). As discussed above, the PPE protocol may be associated with a patient area. In this regard, a first patient room may have a first PPE protocol, a second patient room may have a second PPE protocol, and a third patient room may have no PPE protocol. In the action that a specific patient room has no PPE protocol (meaning that there is only a hand hygiene opportunity and not a hand hygiene/PPE opportunity), flow diagram 920 goes to 928 in order to select a time period to allow for performing hand hygiene prior to the detection of the HH opportunity. In the action that a specific patient room has a PPE protocol (meaning that there is a HH/PPE opportunity), flow diagram 920 goes to 923 in order to select a time period to allow for performing hand hygiene and PPE prior to the detection of the HH opportunity. In other words, if the healthcare provider both cleans his/her hands and puts on PPE prior to entering the room (and thus triggering the HH/PPE opportunity), the system provides for a longer time to perform this. In contrast, if the healthcare provider only cleans his/her hands prior to entering the room (and thus triggering the HH opportunity), the system provides for a shorter time to perform this. In this way, the time set at 928 is shorter than the time set in 923 (e.g., 10 seconds versus 20 seconds). In particular, the wait time may be dynamic based on the different protocols determined (e.g., dynamic waiting time dependent on whether there is a PPE protocol for the patient room).

At 924, it is determined whether the HH action and/or PPE action has been detected within the certain time. In the situation in which the healthcare provider enters the room, the PPE is positioned outside of the patient room. Thus, the healthcare provider will have taken the hand cleaning agent outside of the patient room, and then put on the PPE prior to entering the room. In this way, 924 determines whether one or both of the triggers have been detected (e.g., sensing dispensing of hand sanitizer and/or sensing a cabinet/drawer opening). If not, it is determined that there has been no hand cleaning or PPE donning prior to entry, and at 925, non-compliance is determined. If so, at 926, motion data in the wristband may be accessed based on the time of detected HH Action and/or PPE action in order to determine compliance with hand movements and PPE movements. Further, at 927, compliance, partial compliance or non-compliance for both the HH action and PPE action may be determined based on accessed motion data. As shown in FIG. 9C, flow diagram 920 after 928 is similar to FIG. 6B.

Figure 9D:
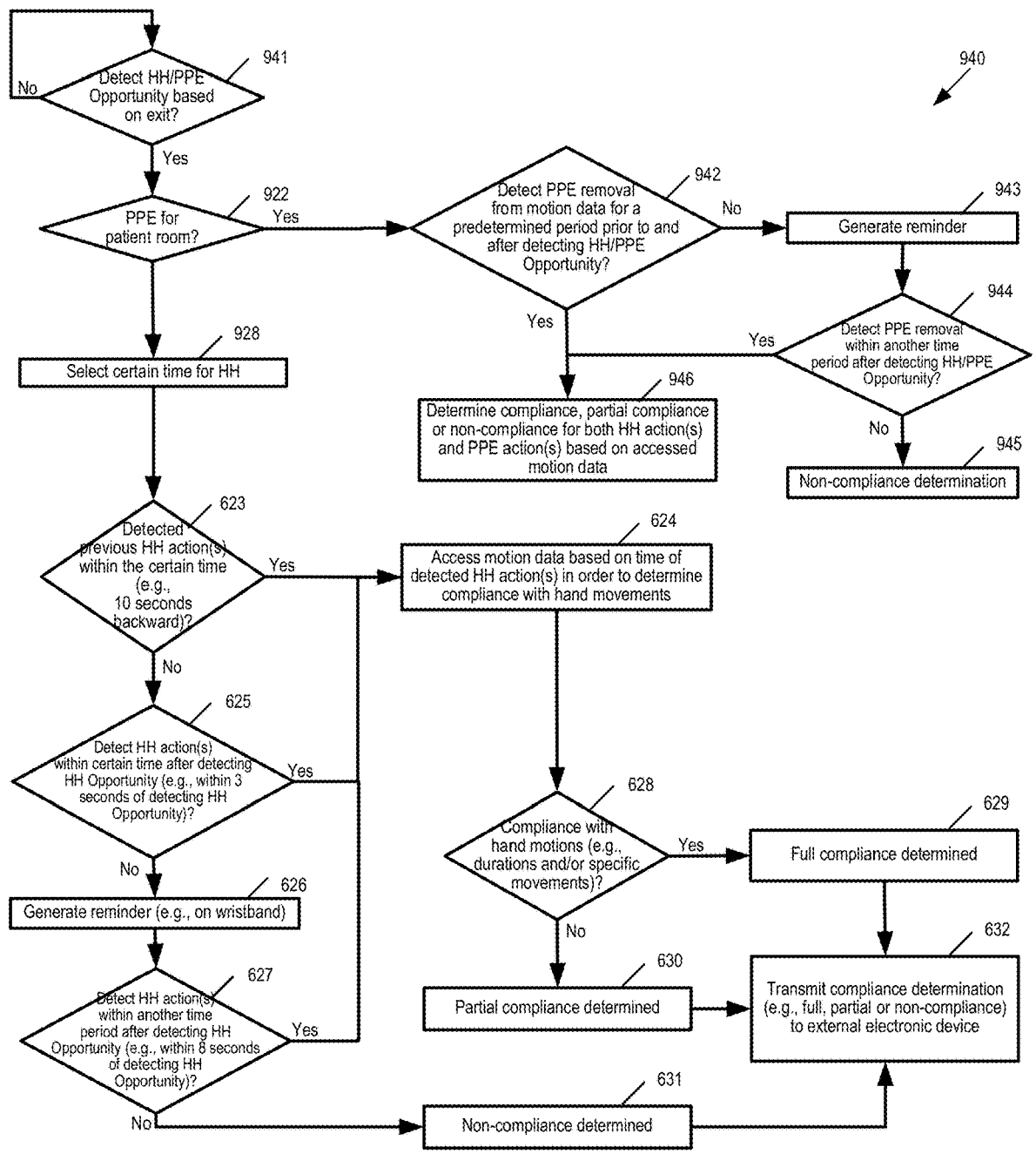
FIG. 9D is a flow diagram of one example of determining whether there is sufficient connection between the detected HH action/PPE action and the detected HH/PPE opportunity when exiting a patient area.

FIG. 9D is a flow diagram 940 of one example of determining whether there is sufficient connection between the detected HH action/PPE action and the detected HH/PPE opportunity when exiting a patient area. At 941, it is determined whether there is a HH/PPE opportunity detected on exit. As discussed above, guidelines dictate that PPE is removed prior to hand cleaning. Further, the healthcare provider may begin to remove the PPE prior to or after detecting the HH/PPE opportunity. For example, the healthcare provider may toss the PPE in the trash can 2498 or in a trash can outside of the room. Thus, in detecting whether PPE has been tossed, the motion data both before and after detecting the HH/PPE opportunity may be reviewed. For example, at 942, it is determined whether PPE removal has been detected from motion data for a predetermined period prior to and after detecting HH/PPE opportunity (e.g., for 2 seconds before and 3 seconds after detecting HH/PPE opportunity). If not, at 943, a reminder to the healthcare provider (such as via the wristband may be output). The healthcare provider is then given a short time period thereafter to comply with removing PPE and hand hygiene. This is determined at 944 where it is determined whether PPE removal is detected within another time period after detecting the HH/PPE Opportunity. If it is not determined that PPE removal was detected within the another time period, at 945, non-compliance is determined (thus meaning that any PPE removal was too remote from the detected HH/PPE Opportunity). Otherwise, at 946, the accessed motion data is used to determine compliance, partial compliance or non-compliance for one or both of the HH action and PPE action, as discussed above. In this way, the compliance determination for PPE removal and/or hand hygiene is sufficiently proximate to the detected HH/PPE Opportunity.

Figure 10A:
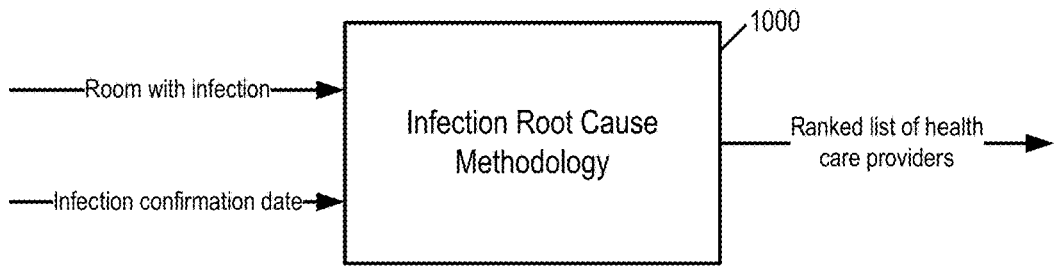
FIG. 10A is an example block diagram of the infection root cause methodology.

FIG. 10A is a block diagram for the infection root cause methodology 1000, which may be programmed to perform the infection root cause analysis. As shown in FIG. 10A, infection root cause methodology 1000 receives as input the area, such as the patient room, with the infection and the infection confirmation date. As output, infection root cause methodology 1000 may generate a ranked list of healthcare providers. In one implementation, infection root cause methodology 1000 may identify some or all visits of hygiene opportunities (such as any of the opportunities discussed above) within a predetermined period (such as a critical time period). For example, the critical period may be 7 days after confirming infection of the patient, although other critical periods are contemplated. As another example, the critical period may be automatically identified based on the type of infection in the area (e.g., different infections have different incubation periods; as such, the critical period may be selected based on the identified incubation period). In this way, an electronic medical record (EMR) may identify when an infection is diagnosed. To determine what caused the infection, the time period before the infection is confirmed may be examined.

Infection root cause methodology 1000 may then identify healthcare providers, associated with the hygiene opportunities, that visited the area during the critical period that may have contributed to the infection in the room. Infection root cause methodology 1000 may, for each provider, analyze compliance for one, some, or all of the opportunities. As discussed above, opportunities may be directed to: entry into the patient area; while in the patient area; and exit from the patient area. Infection root cause methodology 1000 is directed to infection in the patient area. As such, opportunities with regard to exit from the patient area are not considered. In this regard, infection root cause methodology 1000 may analyze for each provider any one or both of: the quantity and/or quality of hygiene when entering a patient area; or the quantity and/or quality of hygiene while in the patient area. As discussed above, one may track the location of the healthcare provider in order to identify when the healthcare provider is entering the patient area. However, tracking activity within the patient area may be more difficult. As such, infection root cause methodology 1000 may estimate a number of opportunities within the patient area based on any one, any combination, or all of: the duration of the visit by the healthcare provider; the role of the healthcare provider (e.g., nurse versus doctor versus custodian); or the patient precautions. Thus, the quantity and/or quality of hygiene within the room for a specific healthcare provider may be estimated based on given the estimated the number of opportunities for the specific healthcare provider multiplied by the historical compliance rate for the specific healthcare provider. Based on the analysis, the infection root cause methodology 1000 may assign each healthcare provider an assessment, such as a score (e.g., poor hygiene quality entering/in a room correlates with a higher score; more frequent hygiene entering/in a room correlates with a higher score). Thus, the score may comprise an objective measure based on a healthcare provider's hygiene opportunity count and performance. In instances where total visit duration is not available due to missing data, visit duration may be estimated to be the population's average.

Alternatively, ranking healthcare providers for infection root cause analysis may be based on one or more criteria, such as any one, any combination, or all of: number of visits; quality of hand hygiene (e.g., full compliance; partial compliance; no compliance); quality of PPE (e.g., compliance with donning and doffing; percentage compliance); total duration of visits (e.g., longer visits tend to indicate a higher likelihood of transmitting infection); or details of each visit (e.g., when healthcare provider entered and/or exited; compliance upon entering versus leaving). In one example, the ranking of the healthcare providers may be based on any one, any combination, or all of: total number of visits; total % compliance of visits; or total duration of visits. For example, the ranking may comprise a local rank. In particular, healthcare providers may be ranked from highest to lowest rank by being assigned a Local Rank score. This score represents a weighted score based on any one, any combination, or all of: visit duration (e.g., total visit duration of a respective healthcare provider in the patient room); hand hygiene compliance (e.g., better hand hygiene compliance translates into a lower (e.g., better) score); PPE compliance (e.g., better PPE compliance translates into a lower (e.g., better) score); Room Precautions (e.g., specific PPE requirements and/or hand hygiene requirements); and confirmation date of infection. The rank is titled "Local Rank" because a score is calculated for one healthcare provider relative to other healthcare providers in the population. In this regard, the Local Rank score in one room with one date range may be different for the same room (or for a different room) with a different date range. Thus, the Local Rank score is tailored to the specific patient area and specific critical time period.

Figure 10B:
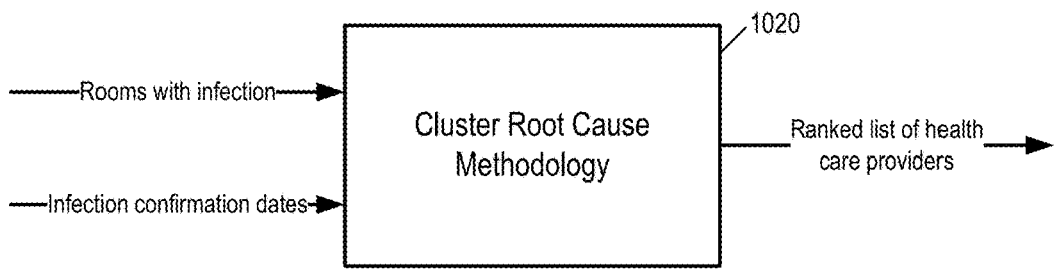
FIG. 10B is an example block diagram of the cluster root cause methodology.

FIG. 10B is a block diagram for the cluster root cause methodology 1020, which may be programmed to perform the cluster root cause analysis. In one or some embodiments, cluster root cause analysis is an extension of the infection root cause analysis. Cluster root cause methodology 1020, like infection root cause methodology 1000, may return a list of providers who may have contributed to an infection. However, cluster root cause methodology 1020 may consider multiple rooms in order to determine how the infection spread from room to room. For example, cluster root cause methodology 1020 may focus on how a pathogen is transmitted from room to room, typically called cross-contamination. Cross-contamination may occur when a provider leaves one identified infection room (representing one opportunity) with poor hygiene, and subsequently enters a second room (representing another opportunity). As discussed above, the opportunities may be connected, such as in time (e.g., a time period between opportunities of less than 60 minutes for pathogen transmission to occur).

As shown in FIG. 10B, cluster root cause methodology 1020 receives as input the areas, such as the patient rooms, with the infections, and the infection confirmation dates. As output, cluster root cause methodology 1020 generates a ranked list of healthcare providers. In one implementation, cluster root cause methodology 1020 may perform root cause analysis in which each healthcare provider is assigned a root cause analysis score. In one or some embodiments, one score is assigned for every input room's hygiene opportunities. Thus, cluster root cause methodology 1020 may assign each provider a cross contamination score (e.g., frequent cross-contamination correlates with a higher score; cross-contamination with worse hygiene correlates with a higher score).

Thus, cluster root cause methodology 1020 may identify some or all visits of healthcare providers to the area within a predetermined period (e.g., a critical period, which may be a predetermined time or dependent on the underlying infection). Cluster root cause methodology 1020 may then rank healthcare providers based on one or more criteria, such as any one, any combination, or all of: number of infected rooms visited; number of visits to each infected room; quality of hand hygiene; quality of PPE; or total duration of visits. In one example, the ranking of the healthcare providers as output may be based on any one, any combination, or all of: total number of visits; total % compliance of visits; or total duration of visits.

Separate from, or in addition to, performing infection analysis to identify higher-risk healthcare providers, the infection analysis may also identify higher-risk patients/ patient rooms for potential future infections. In one or some embodiments, future infection analysis may be based on one or more factors, such as one or both of: environmental spread (e.g., healthcare providers pick up pathogens from the environment (air, water, fomites) and, with poor hygiene, may carry these pathogens into a patient room); or cross contamination (e.g., a provider leaves an infected room with poor hygiene and subsequently enters a yet-uninfected room with poor hygiene). In this way, future infection analysis may take one or more forms, such as independent of infections previously diagnosed (e.g., environmental spread) or dependent on infections previously diagnosed (e.g., cross contamination).

Figure 10C:
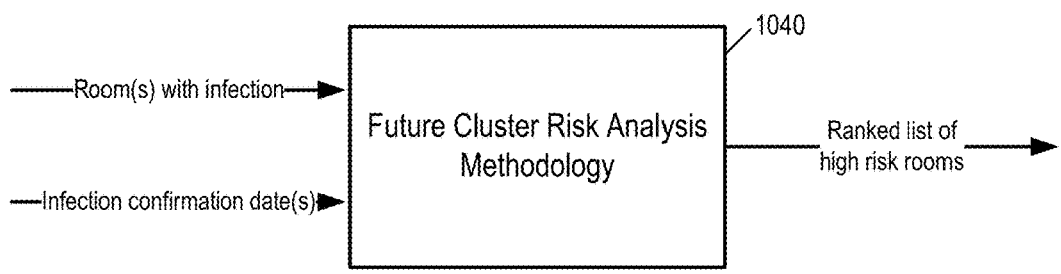
FIG. 10C is an example block diagram of the future cluster risk analysis methodology.

As one example, future infection analysis may be based on infections previously diagnosed in order to determine a future risk that the previously diagnosed infections will spread to other patients/patient areas. This is depicted in FIG. 10C, which is an example block diagram of the future cluster risk analysis methodology 1040, embodying a cross-contamination algorithm, in order to determine future cross contamination risk. As shown, future cluster risk analysis methodology 1040 has as its inputs room(s) with a confirmed infection and associated date(s) of confirmed infection. Future cluster risk analysis methodology 1040 may thus analyze opportunity data, such as compliance data, in order to determine whether an infection, which is confirmed in a first patient area, may spread or be transferred to a second patient area. In this regard, future cluster risk analysis methodology 1040 may divide the analysis infection room by infection room (e.g., infected rooms comprise patient room #2, patient room #8, patient room #12, and patient room #24), and determine for each infected room, a future risk of spread of infection to other (not as-of-yet-infected with the pathogen in the respective room) patient rooms, and determine an overall future risk of spread of infection to the other rooms (e.g., summing the future risk of infection for a respective room due to the spread from all the infected rooms). For example, responsive to identifying an infection in patient room #2 with an associated infection confirmation date, opportunity data (and associated compliance data) may be analyzed to determine other patient rooms connected with patient room #2. Specifically, of note, exit opportunities from a first infected patient room that are connected to entrance opportunities to another patient room (whether the another patient room is generally uninfected or is specifically uninfected with the infections from the first infected patient room).

Figure 10D:
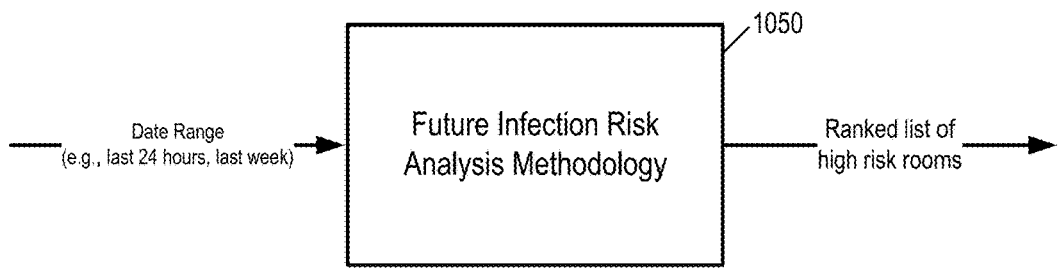
FIG. 10D is an example block diagram of the future infection risk analysis methodology.

FIG. 10D is a block diagram for the future infection risk analysis methodology 1050, embodying an environmental spread algorithm, which may be programmed to perform the future infection risk analysis. In this regard, the future infection risk analysis methodology 1050 may comprise an environmental spread algorithm for environmental spread analysis. Further, in one or some embodiments, future infection risk analysis methodology 1050 receives as input a date range, such as the past 24 hours, the past week, etc., as illustrated in FIG. 10D. Various output(s) generated by future infection risk analysis methodology 1050, such as a ranked list of high-risk rooms, are contemplated.

In one or some embodiments, the environmental spread algorithm (depicted in future infection risk analysis methodology 1050) may identify all hygiene opportunities for one, some, or all of the patient areas (e.g., the patient rooms). For each identified patient area, analyze one or both of: (1) the quantity and/or quality of hygiene entering the room (e.g., one opportunity); or (2) quantity and/or quality of hygiene within the room (e.g., other opportunity). As discussed above, one may estimate the number of opportunities within the room based on any one, any combination, or all of the duration of the visit, provider role, and patient precaution. Each patient area may be assigned an environmental spread score (e.g., poor hygiene quality entering/in the room correlates with a higher score; more frequent hygiene entering/in the room correlates with a higher score).

Figure 10E:
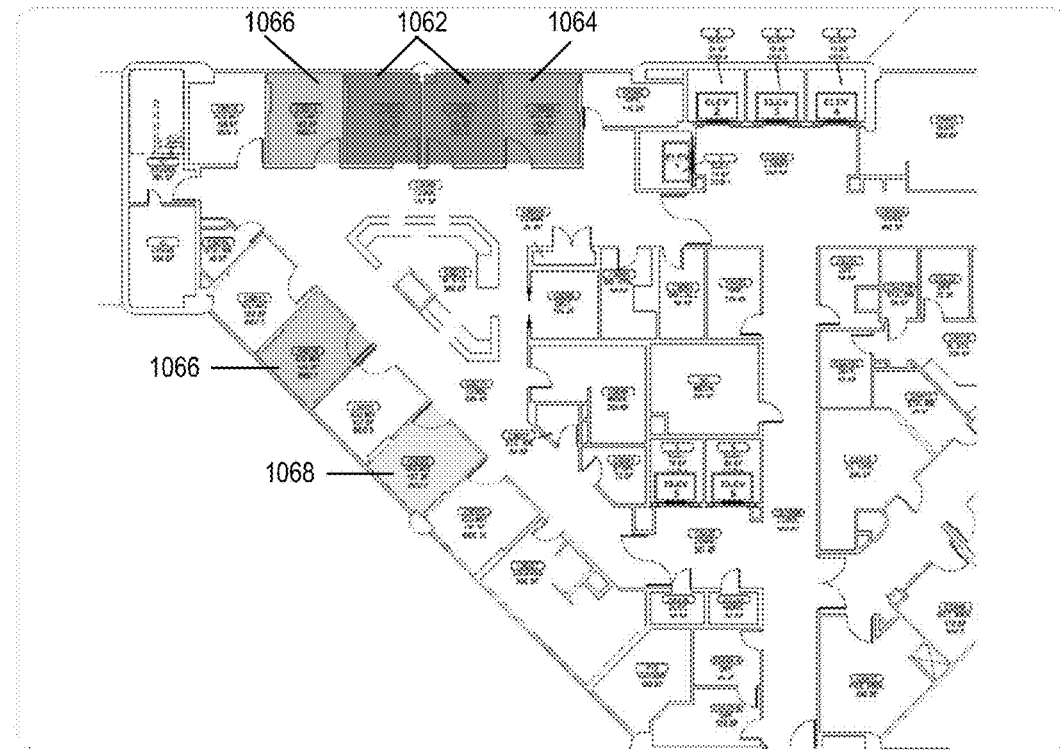
FIG. 10E is an illustration of an infection spread analysis that may be generated by the future cluster risk analysis methodology of FIG. 10C and/or future infection risk analysis methodology of FIG. 10D.

In one or some embodiments, the cross contamination algorithm (depicted in future cluster risk analysis methodology 1040) may identify cross contamination events between infected rooms and/or yet-uninfected rooms; and assign each room a cross contamination score (e.g., more frequent travel from infected rooms results in a higher score; travel with lower-quality hygiene results in a higher score). Scores may be represented with a table or heat map, such as illustrated in FIG. 10E (e.g., darker colors representing higher scores).

In practice, future cluster risk analysis methodology 1040 and/or future infection risk analysis methodology 1050 identify high-risk patient areas by identifying one or both of: visits performed by high-risk providers; or visits to a given patient area that cross certain risk thresholds (e.g., any one, any combination, or all: high number of visits to a patient area (such as higher than a predetermined number); low hand hygiene and/or PPE compliance throughout visits; or total duration of visits to a patient area). An example of a heat map is illustrated in GUI 1060 of the infection spread analysis in FIG. 10E. Heat map may include different colors, such as a range of colors, depicting the risk to certain patient areas. For example, FIG. 10E shows colors 1062, 1064, 1066, 1068 (with darker colors indicating higher risk) that are associated with different areas of a layout of a floor of a patient area. In one manner, future infection risk scores, such as by cross-contamination and/or environmental spread, may be normalized (e.g., score=0: no chance of infection; score=100: 100% chance of infection). A score over a certain amount or within a certain range may be assigned a certain risk category (e.g., scores 85-100 are designated as high risk). In this way, future cluster risk analysis methodology 1040 and/or future infection risk analysis methodology 1050 may predict other infections even before the infections have been diagnosed.

Alternatively or in addition to generating an output, such as an indication of likely healthcare provider(s) who caused the infection and/or an indication of higher-risk patient area(s), one or more protocols, such as the hand hygiene protocols and/or the PPE protocols, may be modified responsive to the analysis, such as any one, any combination, or all of the infection root cause analysis, cluster root cause analysis, future cluster risk analysis and future infection risk analysis. As one example, responsive to identifying higher-risk patient areas, the hand hygiene protocols and/or the PPE protocols may be modified. In particular, responsive to identifying that a specific healthcare provider likely caused a certain type of infection (e.g., a MRSA infection), the hand hygiene protocols and/or the PPE protocols may be changed in patient rooms where the specific healthcare provider had recently visited even in advance of patients in those higher-risk rooms being diagnosed with the certain type of infection (e.g., change the hand hygiene and PPE protocols to comport with treating a patient with a MRSA infection).

Figure 12A:
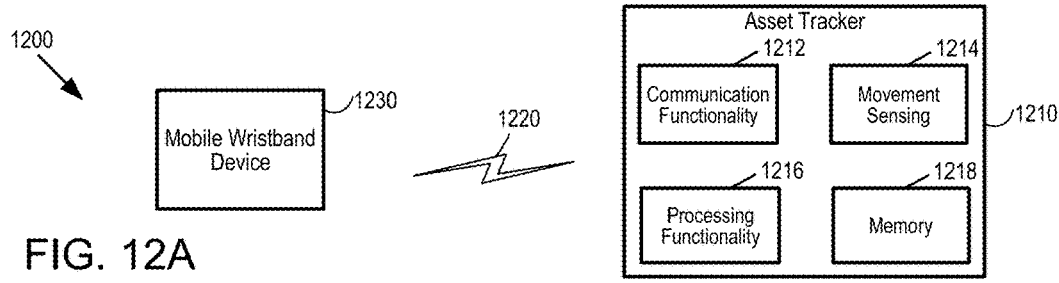
FIG. 12A illustrates one example block diagram of an asset tracker, which may include communication functionality, movement sensing, processing functionality, and memory.

FIG. 12A illustrates one example block diagram 1200 of an asset tracker 1210, which may include communication functionality 1212, movement sensing 1214, processing functionality 1216, and memory 1218. Communication functionality 1212 may comprise one or more wireless communication functionalities, such as Bluetooth or other near-field communication, Wi-Fi, cellular, or the like. In sleep-mode, asset tracker 1210 operates at lower power, including turning off at least part of communication functionality 1212 so that the asset tracker does not wirelessly communicate with external devices. Movement sensing 1214 comprises micro-vibration sensor 312 or the like and is configured to generate a signal responsive to movement. In this regard, movement of at least a part of the asset, such as the entire asset itself or a part of the asset (such as a drawer or a cord of a respirator), results in movement sensing 1214 generating a signal for input to processing functionality 1216. In response, processing functionality 1216 wakes up, including waking up communication functionality 1212, so that asset tracker 1210 may communication wirelessly 1220 with devices proximate, such as via Bluetooth with mobile wristband device 1230 (which may comprise any one, any combination, or all of FIGS. 3A-C). As discussed in more detail below, processing functionality 1216 may monitor one or more aspects, such as who move the asset, when the asset was moved, where the asset was moved, and the like. For example, responsive to asset tracker 1210 sending a communication to mobile wristband device 1230 (or other mobile electronic device associated with the person moving the asset), mobile wristband device 1230 may wake up its CPU (optionally, the mobile wristband device 1230 may be partly asleep (such as its CPU) though the radio transceiver for mobile wristband device 1230 is on to receive the communication; further, the mobile wristband device 1230 may optionally begin monitoring for PPE or the like) and may send a response and include any one, any combination, or all of: (1) an identification of the wristband; (2) a current location of the wristband (e.g., the mobile wristband device 1230 may use a GPS receiver resident on the mobile wristband device 1230 in order to generate the current location); or (3) a current time. Alternatively, asset tracker 1210 may include a GPS receiver in order to generate the current location and a local clock in order to generate the current time. The monitored one or more aspects may be stored in memory 1218, and may optionally be wirelessly transmitted externally of the asset tracker 1210 for storage, such as via Wi-Fi to a back-end server for permanent or semi-permanent storage. Regardless, various aspects of the asset may be tracked, such as the asset's info (any one, any combination, or all of asset type, ID, etc.), the movement of the asset, use of the asset (e.g., the person who opened the drawer of the asset being tracked and/or how long the drawer was opened may be recorded in order to determine time/who dispensed medicine; the person who pulled the plastic tubing from the wall of the patient room and connected to a respirator). After a predetermined time period of no movement of the asset tracker 1210, processing functionality 1216 may return the asset tracker 1210 to sleep mode.

Figure 12B:
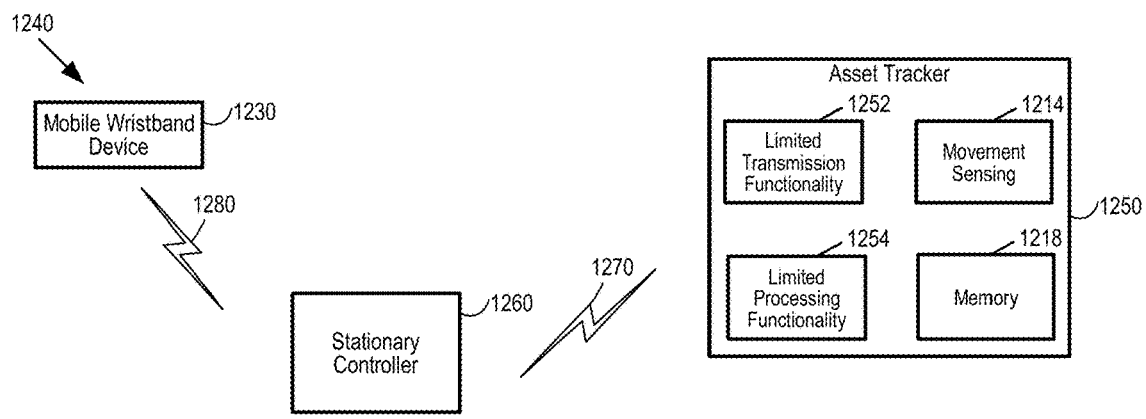
FIG. 12B illustrates another example block diagram of an asset tracker, which may include less functionality than asset tracker illustrated in FIG. 12A.

FIG. 12B illustrates another example block diagram 1240 of an asset tracker 1250, which may include less functionality than asset tracker 1210. In particular, asset tracker 1250 includes limited transmission functionality 1252 and limited processing functionality 1254. For example, responsive to movement sensing 1214 sensing movement, limited processing functionality 1254 wakes up at least a part of asset tracker 1250, such as waking up limited transmission functionality 1252. Limited transmission functionality 1252 includes less communication functionality than communication functionality 1212, such as beacon transmission functionality that transmits a beacon that includes a unique identifier of the asset tracker (which is correlated to the underlying asset) but not wireless receiving capability (such as bi-directional communication via Bluetooth or Wi-Fi). Responsive to movement sensing 1214 sensing movement, asset tracker 1250 uses limited processing functionality 1254 in order to generate the beacon wirelessly via 1270 to stationary controller 1260 via limited transmission functionality 1252. In this regard, limited processing functionality 1254 has less capability than processing functionality 1216, such as being incapable of communicating/processing to identify mobile wristband device 1230. Rather, stationary controller 1260, responsive to receiving the beacon, is configured to communicate wirelessly via 1280 with mobile wristband device 1230. Similar to above, responsive to stationary controller 1260 sending a communication to mobile wristband device 1230, mobile wristband device 1230 may send a response and include any one, any combination, or all of: (1) an identification of the wristband; (2) a current location of the wristband; or (3) a current time. Alternatively, stationary controller 1260 may be preprogrammed with its location (e.g., patient room #10) or include a GPS receiver in order to generate the current location and a local clock in order to generate the current time. Thus, mobile wristband device 1230 may send its unique identifier (thereby identifying the healthcare provider assigned to mobile wristband device 1230), its location and the like. In turn, stationary controller 1260 (which may comprise any one, any combination, or all of FIGS. 4A-B) may store the unique identifier for local storage and/or for transmission a server (such as back-end server 130). In this regard, in one or some embodiments, the stationary controller 1260 communicates with mobile wristband device 1230 responsive to receiving the beacon. Alternatively, or in addition, stationary controller 1260 may have already communicated with mobile wristband device 1230, such as responsive to the healthcare provider walking into the patient area (e.g., when the mobile wristband device 1230 is within Bluetooth communication with the stationary controller 1260, the stationary controller 1260 may identify the mobile wristband device 1230). Thus, in such an embodiment, the stationary controller 1260 may connect two separate communications (e.g., communicating with the mobile wristband device 1230 in order to identify the mobile wristband device 1230 and receiving the beacon from asset tracker 1250) in order to identify the mobile wristband device 1230 that has moved the asset. As discussed above, the asset tracker (such as asset tracker 1210, 1250) may go back to sleep after no movement for a predetermined amount of time. In one or some embodiments, the asset tracker may send a final beacon indicating that the asset tracker is going back to sleep. The stationary controller 1260 that receives the final beacon (whether in the patient room when the asset tracker awakened or in another patient room) may then determine that this is the present resting position of the asset. For example, the asset may originate in a first room (e.g., ICU room #2) with the stationary controller in the first room receiving the beacon from the asset tracker upon wake-up (responsive to the original movement). Thereafter, the asset may be moved to a second room (e.g., ICU room #5) with the stationary controller in the second room receiving the beacon from the equipment responsive to movement of the equipment into the second room.

Figure 11A:
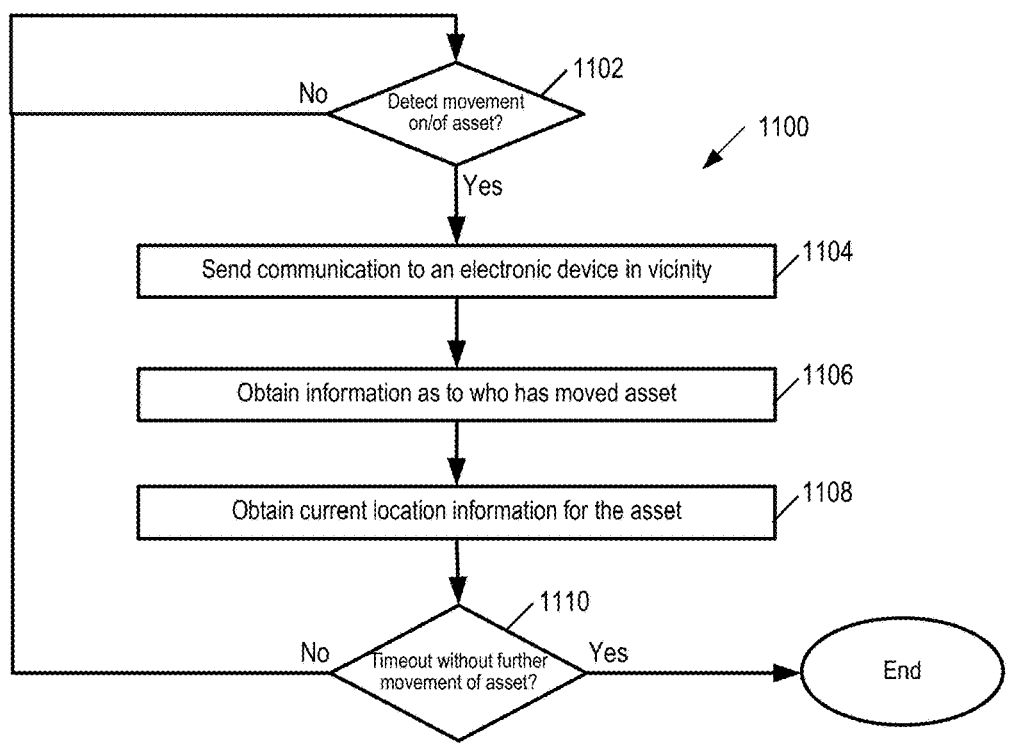
FIG. 11A illustrates a first flow diagram of asset tracking.

FIG. 11A illustrates a first flow diagram 1100 of asset tracking. At 1102, the asset tracker determines whether there is movement detected on or of the asset. If so, at 1104, the asset tracker sends a communication to an electronic device in its vicinity (e.g., to a proximate wristband or stationary controller). At 1106, information is obtained as to whom as moved the asset (such as by polling the wristband in the vicinity). At 1108, current location information may likewise be obtained. At 1110, the asset tracker may determine whether there has been a timeout without further movement of the asset. If not, flow diagram 1100 goes to 1102. If not, flow diagram 1100 ends.

Figure 11B:
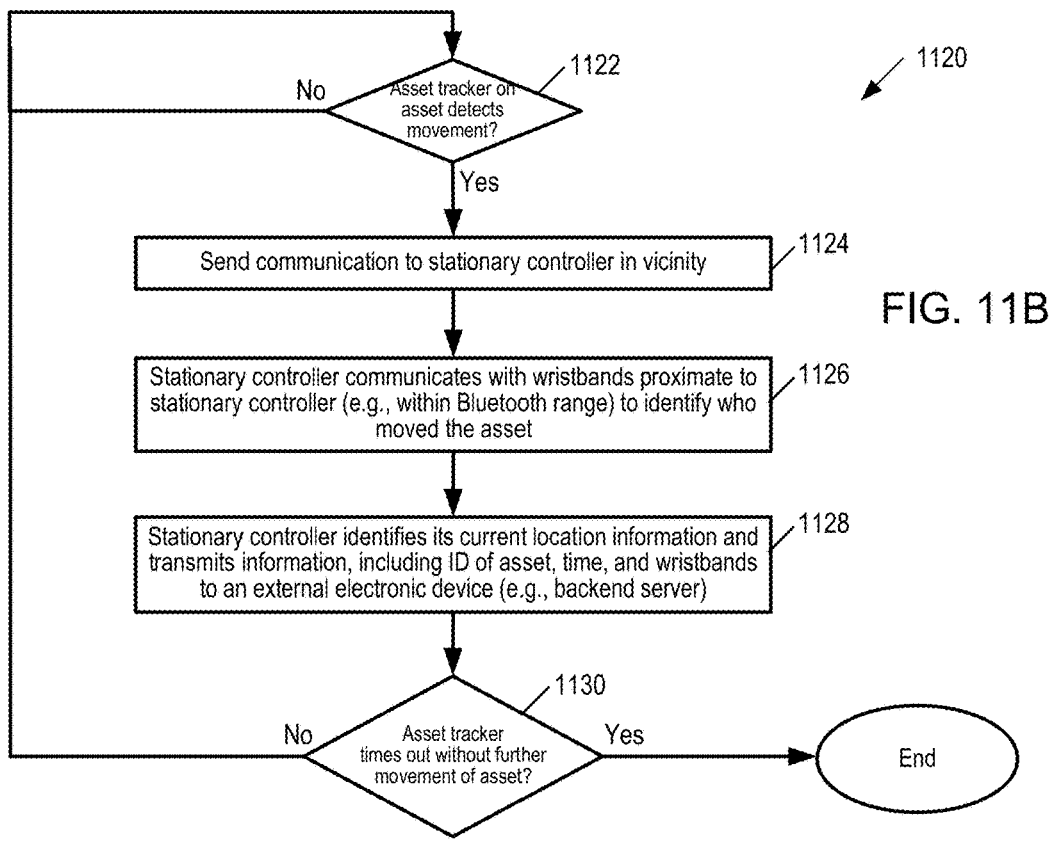
FIG. 11B illustrates a second flow diagram of asset tracking in which the asset tracker communicates with a stationary controller.

FIG. 11B illustrates a second flow diagram 1120 of asset tracking in which the asset tracker communicates with a stationary controller. At 1122, the asset tracker detects movement. At 1124, the asset tracker sends a communication (such as a beacon) to a stationary controller in the vicinity. At 1126, the stationary controller communicates with wristbands proximate to stationary controller (e.g., within Bluetooth range) to identify who moved the asset. At 1128, the stationary controller identifies its current location information (or the current location as sent from the wristband) and transmits information, including ID of the asset, time, and wristbands in proximity to an external electronic device (e.g., backend server). At 1130, the asset tracker determines whether times out has occurred without further movement of the asset.

Figure 11C:
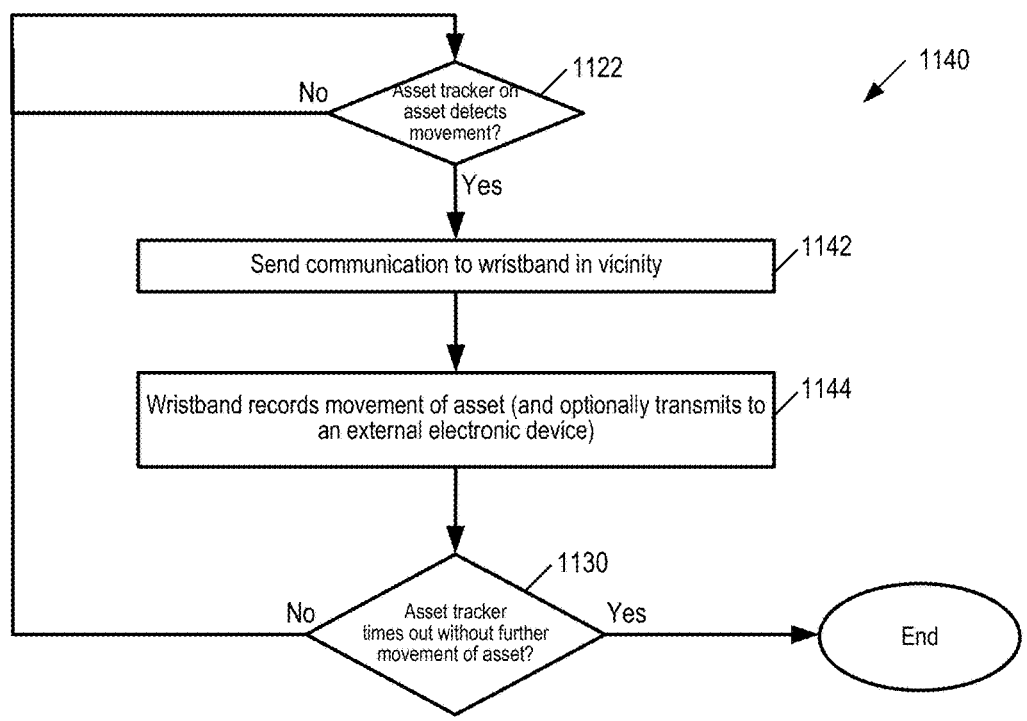
FIG. 11C illustrates a third flow diagram of asset tracking in which the asset tracker communicates with one or more wristbands.

FIG. 11C illustrates a third flow diagram 1140 of asset tracking in which the asset tracker communicates with one or more wristbands. Responsive to the asset tracker detecting movement, at 1142, the asset tracker sends a communication to the wristband(s) in its vicinity. Information, such as any one, any combination or all of when movement occurred, who moved the asset, and current location may be sent. In one or some embodiments, the asset tracker may send the information Alternatively, at 1144, the wristband may record movement of asset (and optionally transmit information to an external electronic device, such as the backend server).

Figure 13:
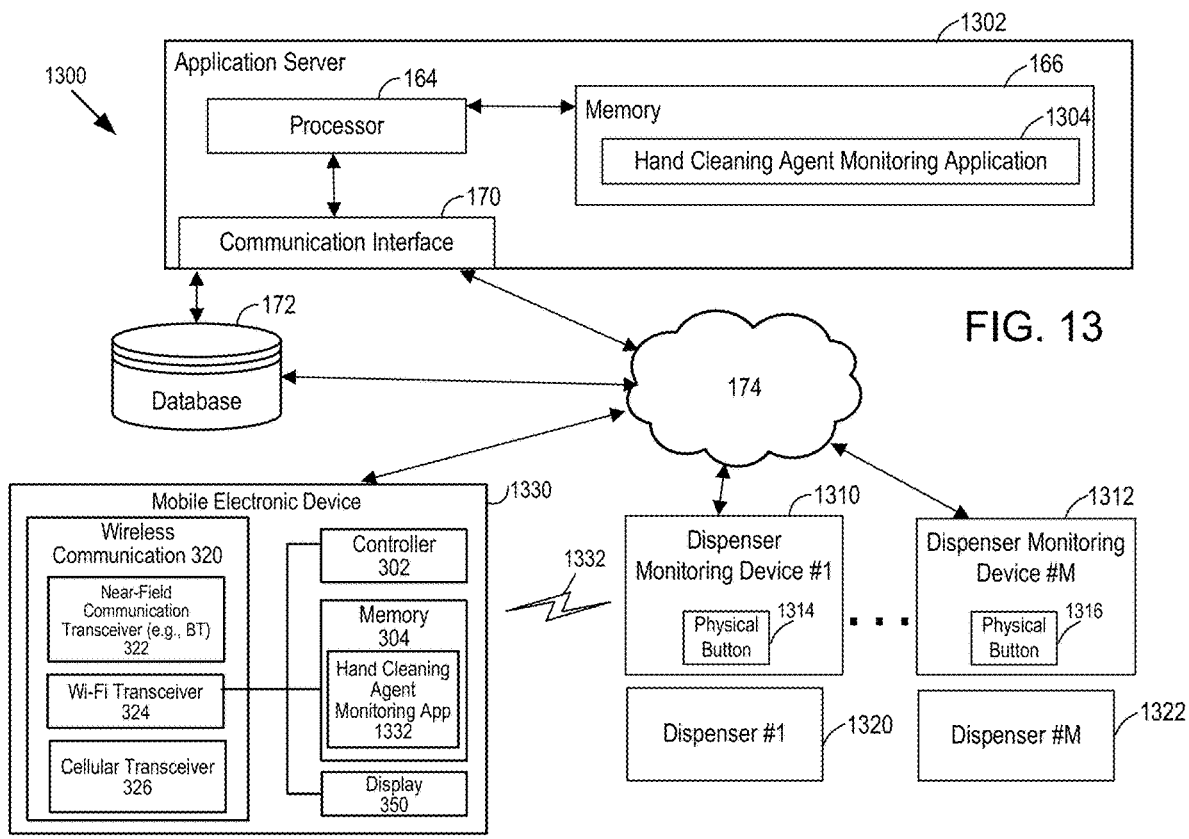
FIG. 13 illustrates a block diagram of a hand cleaning agent monitoring system, which includes an application server, database, network, one or more mobile electronic devices, and one or more dispenser monitor devices and associated dispensers.

FIG. 13 illustrates a block diagram of a hand cleaning agent monitoring system, which includes an application server 1302, database 172, network 174, one or more mobile electronic devices (with one mobile electronic device 1330 illustrated in FIG. 13), and one or more dispenser monitor devices and associated dispensers (with dispenser monitoring device #1 (1310) and associated dispenser #1 (1320), and dispenser monitoring device #2 (1312) and associated dispenser #2 (1322) illustrated in FIG. 13). Application server 1302 includes a hand cleaning agent monitoring application 1304, which may be configured to communicate with one or both of the mobile electronic devices (such as mobile electronic device 1330) and dispenser monitoring devices (such as one or both of dispenser monitoring device #1 (1310) or dispenser monitoring device #2 (1312)). In one or some embodiments, communications with application server 1302 may be directed to refilling of dispensers.

As one example, mobile electronic device 1330 may activate hand cleaning agent monitoring app 1332. In one or some embodiments, hand cleaning agent monitoring app 1332 may generate an output, such as a visual display indicative of a layout illustrating one or more dispensers. A worker using the hand cleaning agent monitoring app 1332 may tap on the screen in order to identify the dispenser subject to refilling (e.g., the tap on the screen identifies the dispenser or the dispenser monitoring device ID). Thus, the hand cleaning agent monitoring app 1332 need not communicate with an external device, such as any monitoring device, in order to identify the dispenser that has been refilled. Alternatively, in order to identify the dispenser for refilling, hand cleaning agent monitoring app 1332 may communicate with a respective dispenser (such as wirelessly communicate via Bluetooth (using near-field communication transceiver 322) or other near-field communication with dispenser monitoring device #1 (1310) in order to obtain the identification of one or both of the dispenser monitoring device (e.g., an ID of dispenser monitoring device #1 (1310)) or the dispenser (e.g., an ID of dispenser #1 (1320)).

Regardless, after identifying the dispenser subject to refilling, and after the worker has replaced the bag of hand cleaning agent (such as replaced in dispenser #1 (1320)), the worker may activate, via hand cleaning agent monitoring app 1332 being executed on the mobile electronic device 1330 (e.g., activate a "refill button" generated by hand cleaning agent monitoring app 1332 on the display 350 of mobile electronic device 1330) in order for the mobile device to transmit a refill communication to application server 1302. In this way, the "refill button" on the display 350 of mobile electronic device 1330 acts as a virtual reset button. The refill communication may be indicative to the application server 1302 that the bag of hand cleaning agent for a dispenser (such as dispenser #1 (1320)) has been replaced. In particular, the refill communication may include any one, any combination, or all of: a field indicating that it is a refill communication; a field indicating the dispenser or the dispenser monitoring device ID that was refilled (e.g., an ID of dispenser monitoring device #1 (1310) and/or an ID of dispenser #1 (1320)); and optionally, a separate field for an ID of the mobile electronic device 1330 and/or an ID of the worker that replaced the bag. In response to receiving the refill communication from the mobile electronic device 1330, the application server 1302 may perform one or both of: (i) update database 172 to indicate that the particular dispenser (such as dispenser #1 (1320)) has been refilled; and (ii) send a communication to the respective monitoring device that its associated dispenser has been refilled (e.g., a server communication sent via Wi-Fi or other farther-field communication methodology, such as farther than near-field communication methodologies such as Bluetooth). In this way, the dispenser monitoring device may communicate with the mobile electronic device 1330 in one wireless manner (e.g., near-field, such as via Bluetooth) and may communicate with application server 1303 in another wireless manner (e.g., farther-field, such as via Wi-Fi). In response to receiving the server communication, the respective monitoring device may reset its indication of the remaining amount of hand cleaning agent in its associated dispenser. For example, the indication may comprise a number value associated with a counter, wherein the number value for the counter indicates the number of dispenses remaining in the dispenser until empty. In practice, the dispenser monitoring device may decrement the number value in the counter every time a dispensing event occurs (e.g., the dispenser dispenses the predetermined amount of hand cleaning agent).

As another example, resetting may be performed using a communication generated by the dispenser monitoring device and transmitted to application server 1302. In particular, responsive to a worker replacing the bag of hand cleaning agent, the worker may provide an input to the dispensing monitoring device. The input may be a manual inputs, such as by pushing physical button 1314 or 1316. Alternatively, the input may be virtual, such as by communicating via an external electronic device, such as mobile electronic device 1330, to transmit the input. Responsive to receiving the input, the dispensing monitoring device may: (i) reset its indication of the remaining amount of hand cleaning agent in its associated dispenser; and/or (ii) generate a dispenser refill communication to transmit to the application server, with the dispenser refill communication comprising any one, any combination, or all of: a field indicating that it is a dispenser refill communication; a field indicating the dispenser or the dispenser monitoring device ID that was refilled; and optionally, a separate field for an ID of the mobile electronic device 1330 and/or an ID of the worker that replaced the bag (which may have been transmitted from the mobile electronic device 1330).

Figure 14C:
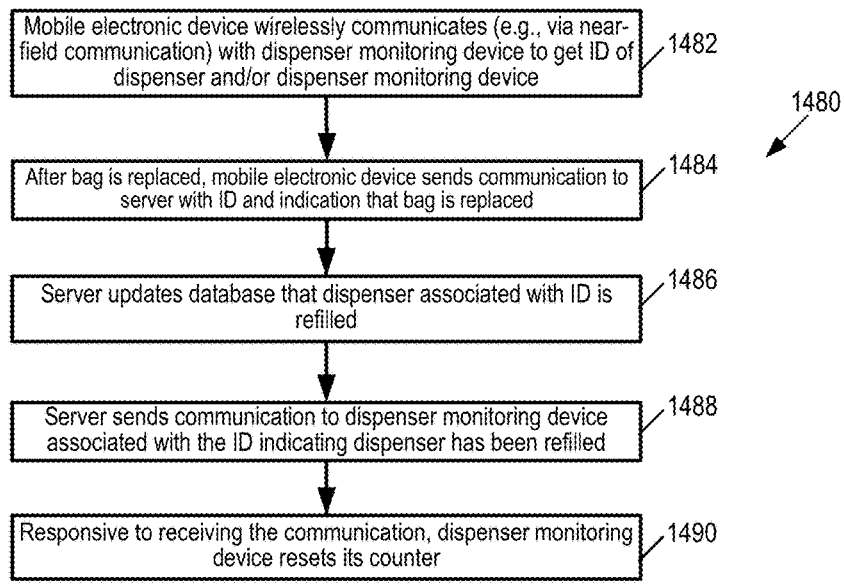
FIG. 14C illustrates a flow diagram of a mobile electronic device communicating with the dispenser monitoring device and with a backend server.
Figure 14A:
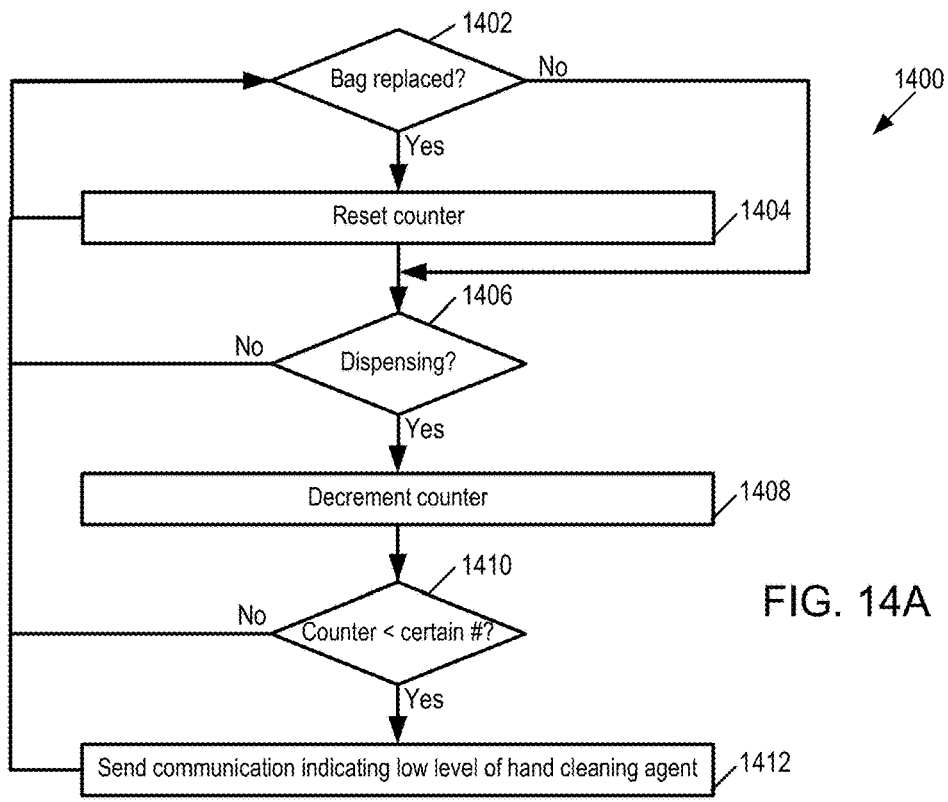
FIG. 14A illustrates a flow diagram of monitoring for a bag (or other type of container) of hand cleaning agent for a respective dispenser.

FIG. 14A illustrates a flow diagram 1400 of monitoring for a bag (or other type of container) of hand cleaning agent for a respective dispenser. At 1402, it is determined whether the bag for the respective dispenser has been replaced. As discussed above, the dispenser monitoring device may receive a direct indication (such as via physical button 1314, 1316) via its interface or a communication, such as from application server 1142, indicating that the bag has been replaced. If so, the value of the counter for the stationary controller associated with the respective dispenser is reset. As discussed above, various indications of the remaining amount of hand cleaning agent in its associated dispenser are contemplated, one of which may comprise a counter. In one or some embodiments, the number for the counter is predetermined (e.g., each bag has 1,000 dispenses so that the number for the counter is always reset back to 1,000). In other embodiments, the number for the counter is dynamic (e.g., a first type of replacement bag has 1,000 dispenses whereas a second type of replacement bag has 500 dispenses; so that, the reset number for the counter is set based on the type of replacement bag). If the bag has not been replaced, flow diagram 1400 moves to 1406, at which the dispenser monitoring device determines whether there has been a dispensing event. As discussed above, the dispenser monitoring device may be part of the stationary controller (e.g., the dispenser monitoring device is integrated with the stationary controller) or work in combination with a stationary controller (e.g., responsive to the stationary controller sensing a dispensing event via its sensor, the stationary controller sends a communication to the dispenser monitoring device). As such, in one embodiment, the stationary controller may be used to determine whether the dispensing event has occurred, as discussed above. Alternatively, the dispenser monitoring device may determine itself whether a dispensing event has occurred. If not, flow diagram 1400 moves to 1402. If so, at 1408, the stationary controller decrements the counter.

Alternatively, or in addition to monitoring dispensing (e.g., decrementing the counter), one or more electronic devices may monitor who dispensed the hand cleaning agent. As one example, people, such as healthcare providers, may wear a mobile electronic device, such as a wristband. The controller resident on the dispenser monitoring device (which may be a controller separate from the stationary controller or may be integrated with the stationary controller) may detect whether a wristband is nearby (e.g., via near-field communication, BLE, or the like). Responsive to the controller resident on the dispenser monitoring device detecting a wristband, the controller may perform one or both of the following: (1) activate a sensor to detect whether hand cleaning agent is being dispensed (thereby activating the sensor only when a wristband is proximate in order to conserve power); or (2) obtain an identifier from the wristband in order to identify who is taking hand cleaning agent (in order transmit the identifier to the backend server for record keeping).

At 1410, the dispenser monitoring device determines whether the number for the counter is less than or equal to a certain number. If so, at 1412, the dispenser monitoring device sends a communication to the backend server indicating a low level of hand cleaning agent. Again, the communication may be sent via the communication functionality of the stationary controller. Alternatively, the communication may be sent via the communication functionality distinct from any stationary controller. For example, if a bag has 1,000 dispenses, when the counter is less than or equal to 50, a communication is sent. Otherwise, flow diagram 1400 moves to 1402. Instead of (or in addition to) sending the communication, the dispenser monitoring device may cause an output to be generated. As one example, the dispenser monitoring device may include one or both of a speaker or a light, and may cause an aural output to be generated by the speaker or a visual output to be generated by the light. In the instance where the dispenser monitoring device is part of, integrated with or associated with a stationary controller, the dispenser monitoring device may use the speakers/light on the stationary device. As another example, responsive to determining that the amount of hand cleaning agent is low (e.g., below a predetermined amount), the dispenser monitoring device may send a communication to an external device to cause an output to be generated via another device. As one example, the communication sent to the application server 1302 may cause the application server 1302 to send a refill alert message to a mobile electronic device, such as mobile electronic device 1330.

Alternatively, instead of the stationary controller resident in the dispensing monitoring device performing the counting, the stationary controller (responsive to detecting a dispensing at 1406) may send a communication to the backend server. In this way, the backend server may be tasked with all counting aspects (such as resetting the counter at 1404, decrementing the counter at 1408, and determining whether the counter is less than or equal to a certain amount at 1410). Further, the stationary controller need not send any communication indicating low level of hand cleaning agent at 1412.

Figure 14B:
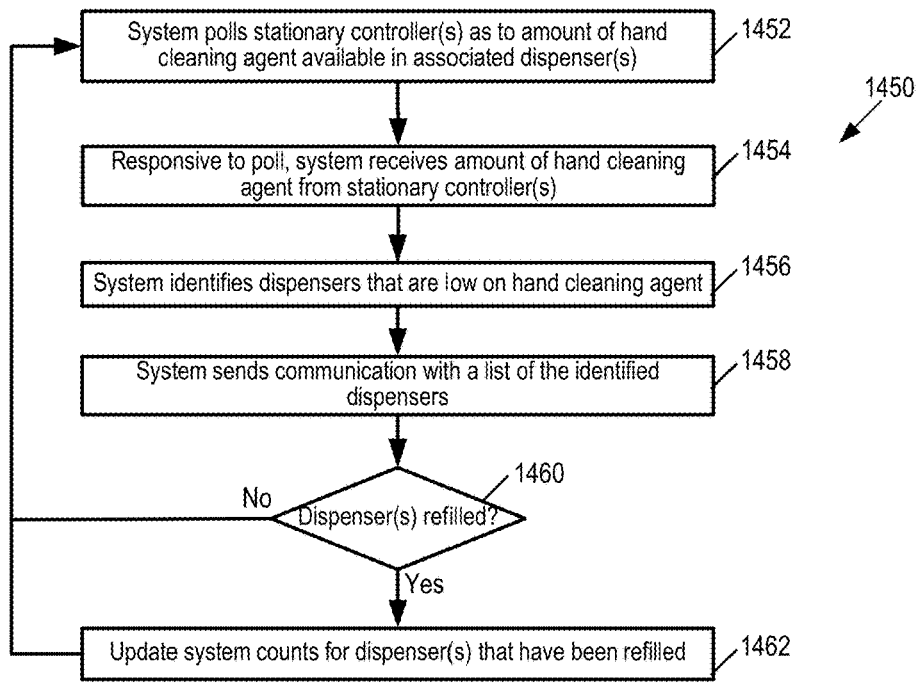
FIG. 14B illustrates a flow diagram of a backend server (such as an application server) monitoring of amount of hand cleaning agent in dispenser(s).

FIG. 14B illustrates a flow diagram 1450 of a backend server (such as application server 1302) monitoring of amount of hand cleaning agent in dispenser(s). At 1452, the system, such as the backend server, polls one or more stationary controllers as to the amount of hand cleaning agent available in the associated dispensers. Thus, in one embodiment, polling by the backend server may be performed at predetermined intervals (such as once per day). Alternatively, polling by the backend server may be performed responsive to a user request. At 1454, responsive to sending the poll, the system receives the amount of hand cleaning agent from dispenser monitoring device(s). Based on the amount of hand cleaning agent from dispenser monitoring device(s), at 1456, the system identifies the dispenser(s) that are low on hand cleaning agent. At 1458, the system sends a communication with the list of identified dispensers. At 1460, it is determined if the dispenser(s) have been refilled. If so, at 1462, the system updates counts for the dispenser(s) that have been refilled. Otherwise, flow diagram 1450 loops back to 1452.

FIG. 14C illustrates a flow diagram 1480 of a mobile electronic device (such as mobile electronic device 1330) communicating with the dispenser monitoring device (such as dispenser monitoring device #1 (1310)) and with a backend server (such as application server 1302). At 1480, the mobile electronic device wirelessly communicates (e.g., via near-field communication) with the dispenser monitoring device to get an ID of the dispenser and/or the dispenser monitoring device. At 1484, after bag is replaced in the dispenser, the mobile electronic device sends a communication to the server with the ID and the indication that bag is replaced. At 1486, the server updates the database that the dispenser (or dispenser monitoring device) associated with ID is refilled. At 1488, the server sends a communication to the dispenser monitoring device associated with the ID indicating dispenser has been refilled. At 1490, responsive to receiving the communication, the dispenser monitoring device resets its counter. Alternatively, instead of mobile electronic device (such as mobile electronic device 1330) communicating with the dispenser monitoring device (such as dispenser monitoring device #1 (1310)) to obtain the ID of the dispenser and/or the dispenser monitoring device, the mobile electronic device may include a visual layout in order for the worker to identify to the position of the respective dispenser in the visual layout (and thereby obtain the ID of the dispenser and/or the dispenser monitoring device correlated to the position of the respective dispenser in the visual layout).

Figure 15A:
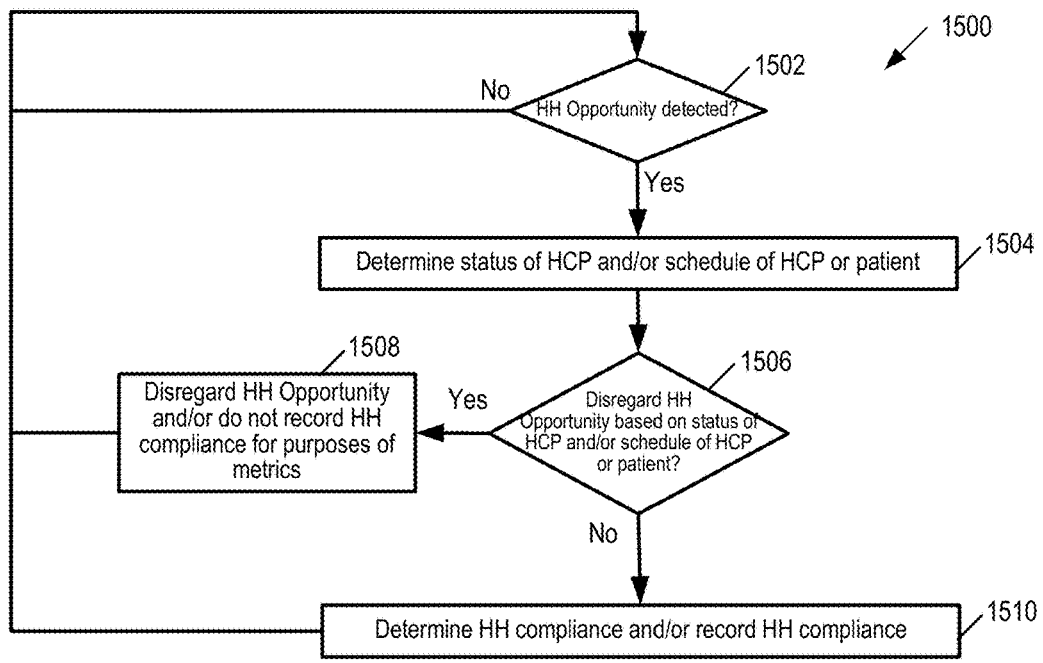
FIG. 15A is a flow diagram for applying rules to determine whether to determine or log compliance with a hand hygiene opportunity.

FIG. 15A is a flow diagram 1500 for applying rules to determine whether to determine or log compliance with a hand hygiene opportunity. At 1502, it is detected that there is a hand hygiene opportunity. At 1504, the status of the healthcare provider (HCP) and/or the patient's or HCP providers schedule is determined. At 1506, it is determined whether to disregard the hand hygiene opportunity based on the status of HCP and/or schedule of HCP or patient. If so, at 1508, the hand hygiene opportunity is disregarded and/or hand hygiene compliance is not recorded for purposes of metrics. If not, at 1510, hand hygiene compliance is determined and/or recorded.

Figure 15B:
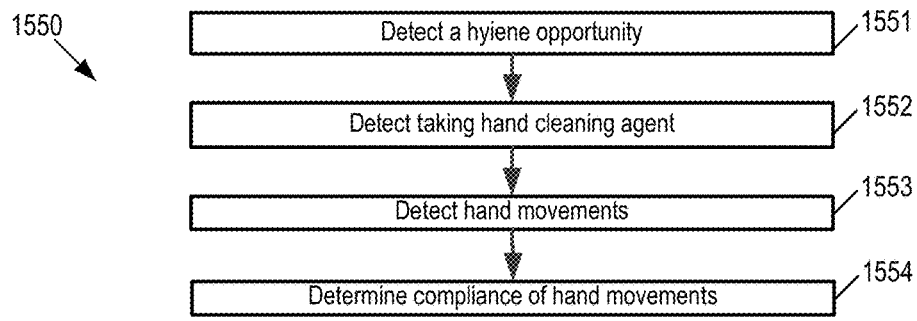
FIG. 15B is a flow diagram for detecting a hygiene opportunity, determining whether hand cleaning agent has been taken, detecting hand movements, and determining compliance based on the hand movements.

FIG. 15B is a flow diagram 1550 for detecting a hygiene opportunity (such as a hand hygiene opportunity), determining whether hand cleaning agent has been taken, detecting hand movements, and determining compliance based on the hand movements. At 1551, the hygiene opportunity is detected. As discussed above, there are various ways in which to detect a hygiene opportunity. As one example, such as in the hospitality industry which may request handwashing periodically (e.g., every 30 minutes), the hygiene opportunity may be determined by a counter, which generates an interrupt or an alarm every 30 minutes. In one or some embodiments, the mobile electronic device, such as the wristband, may house the counter in order to generate the periodic interrupt. At 1552, the taking of hand cleaning agent, such as sanitizer, is detected. For example, the mobile electronic device may determine whether hand cleaning agent has been dispensed. As one example, the mobile electronic device may include a sound sensor, with the sound sensor generating sound data. The mobile electronic device may analyze the sound data in order to determine whether the sound data is indicative of the sound when a dispenser is dispensing sanitizer. As another example, the mobile electronic device may include one or more motion sensors to generate movement data. The mobile electronic device may analyze the motion data in order to determine whether the motion data is indicative of the movements when person moves his/her hand to take sanitizer (e.g., the movement of moving the palm upward). As still another example, the mobile electronic device may communicate with an external electronic device, such as a controller associated with the dispenser, in order to determine whether the hand cleaning agent has been dispensed. In particular, responsive to a dispensing event, the stationary controller may send a near-field communication indicating the dispensing event, with the wristband, in near-field communication range, receiving the communication. Thus, the mobile electronic device may determine the hygiene opportunity (e.g., the hand hygiene opportunity) and determine compliance with the hygiene opportunity. Separate from the hospitality industry, a mobile electronic device associated with a healthcare provider may likewise determine the hygiene opportunity (e.g., based on tracking the healthcare provider) and determine compliance with the hygiene opportunity (e.g., analyze its hand movements to determine compliance).

At 1553, the mobile electronic device may detect hand movements. As discussed above, the mobile electronic device may include one or more motion sensors. As such, responsive to detecting the opportunity and/or responsive to detecting the taking of hand cleaning agent, the mobile electronic device may activate its one or more motion sensors in order to generate motion sensor data. Alternatively, the mobile electronic device may constantly keep its one or more motion sensors active to constantly generate motion sensor data. At 1554, the mobile electronic device may analyze the motion sensor data in order to determine compliance. As discussed above, compliance may be measured in one of several ways, such as based on a duration of hand movements (e.g., at least 20 seconds) and/or based on predefined hand motions.

In this regard, the mobile electronic device may perform one, some, or all of 1551, 1552, 1553, and 1554. Further, the mobile electronic device may determine whether there is full compliance, partial compliance (e.g., taking of sanitizer but not performing the requisite hand movements), or no compliance (e.g., no taking of sanitizer). Alternatively, the mobile electronic device may be configured only to detect the hygiene opportunity and detect whether hand cleaning agent has been taken (e.g., in effect determining whether or not there is partial compliance).

Figure 15C:
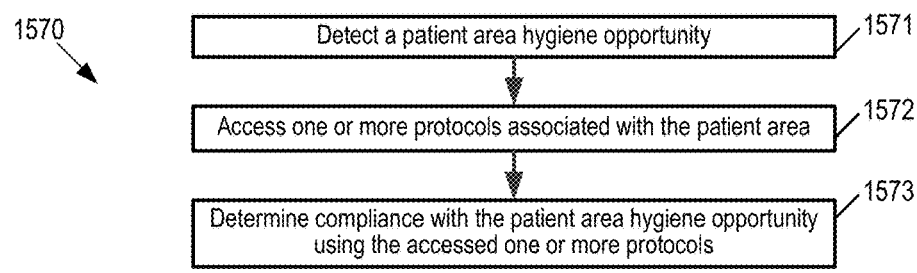
FIG. 15C is a flow diagram for detecting a patient area hygiene opportunity, accessing the protocol(s) associated with the patient area, and determining compliance with the patient area hygiene opportunity using the accessed protocol(s).

FIG. 15C is a flow diagram 1570 for detecting a patient area hygiene opportunity, accessing the protocol(s) associated with the patient area, and determining compliance with the patient area hygiene opportunity using the accessed protocol(s). At 1572, a patient area hygiene opportunity (which is associated with a patient area) is detected. As discussed above, there are a variety of ways in which to detect a patient area hygiene opportunity, such as by tracking a healthcare worker in or about the patient area.

At 1572, one or more protocols associated with the patient area are accessed. As discussed above, the patient area may include one or more protocols, such as one or more HH protocol and/or PPE protocol. Further, the one or more protocols may be predetermined and unchanging (e.g., the same protocol(s) throughout the entire hospital; the mobile electronic device may have prestored therein the same protocol(s); the stationary controller). Alternatively, the one or more protocols may change from one patient area to the next. In this regard, the one or more protocols correlated to the specific patient area subject to the patient area hygiene opportunity may be dynamically determined (e.g., at the server level; at the patient area level; at the server level and the patient area level; by one, some, or all of: the backend server (storing the protocol(s) correlated to the specific patient area); the stationary controller positioned in the specific patient area; or the mobile electronic device in or about the specific patient area). At 1573, compliance is determined for the patient area hygiene opportunity using the accessed one or more protocols.

Figure 16:
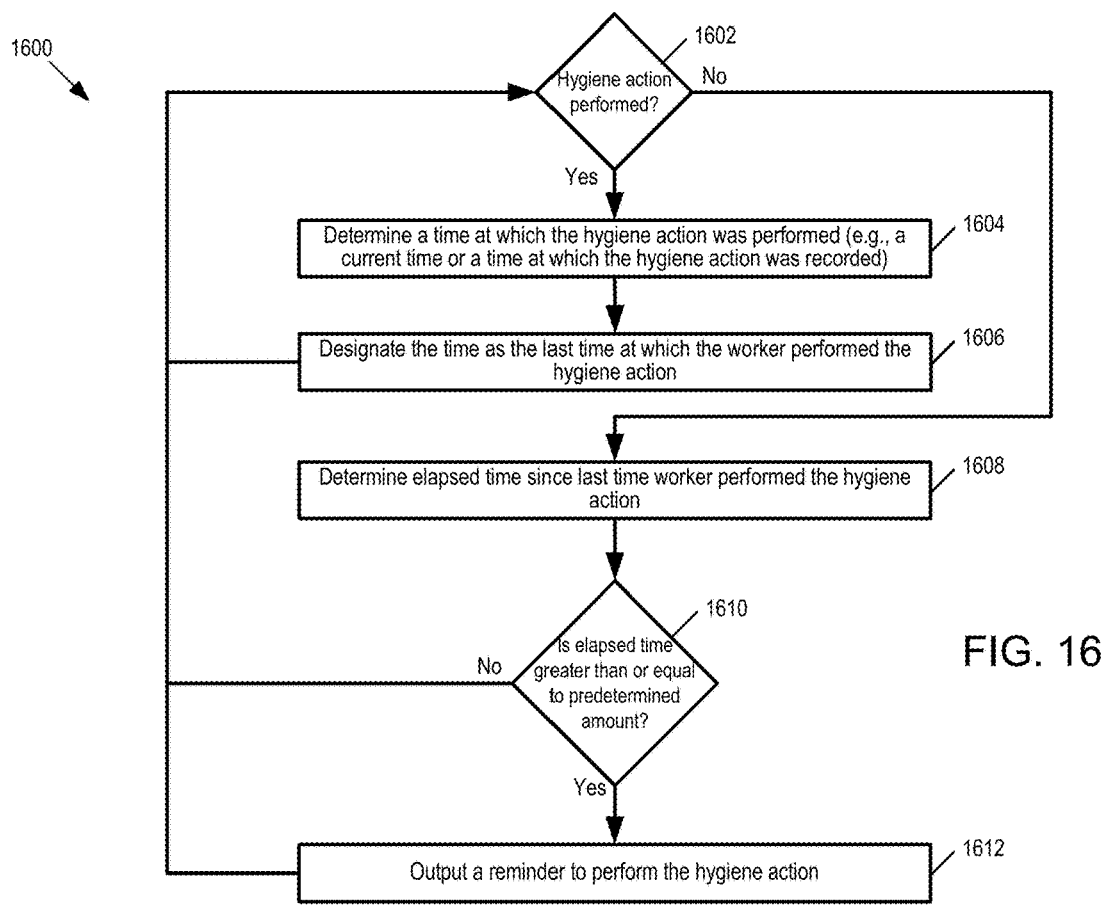
FIG. 16 is a flow diagram for determining whether a hygiene action is performed periodically.

FIG. 16 is a flow diagram 1600 for determining whether a hygiene action is performed periodically. As discussed above, a hygiene action, such as washing hands (or taking hand cleaning agent), may be performed periodically. Further, the checking of the hygiene action may be performed periodically. Thus, at 1602, an electronic device, such as one or both of the stationary controller or the wristband, may determine whether the hygiene action has been performed.

If so, the electronic device may determine a time at which the hygiene action was performed (e.g., a current time or a time at which the hygiene action was recorded). At 1606, the electronic device may designate the time as the last time at which the worker performed the hygiene action. After which flow diagram 1600 loops back to 1602. If not, flow diagram 1600 moves to 1608 where the elapsed time since the last time the worker performed the hygiene action is determined. At 1610, the electronic device determines whether the elapsed time is greater than or equal to a predetermined amount of time. If so, at 1612, the electronic device (such as one or both of the wristband or the stationary controller) may output a reminder to perform the hygiene action. If not, flow diagram 1600 loops back to 1602. For example, the predetermined amount of time may be 30 minutes. In this way, the provider may be expected to perform the hygiene action at least every 30 minutes. If the provider does not perform the action within 30 minutes of the last time the hygiene action was performed, a reminder is generated. If the provider does perform the hygiene action in less than 30 minutes since the last time the hygiene action was performed, a time at which the hygiene action was performed is then set as last time the hygiene action was performed. In this way, the hygiene action is performed at least every 30 minutes (with the start time being dynamically reset based on the time of last hand cleaning); otherwise, the provider is given a reminder to perform the hygiene action. Alternatively, the provider may be given a reminder based on location of the provider (such as based on transition from a first location to a second location), as discussed above.

Figure 17:
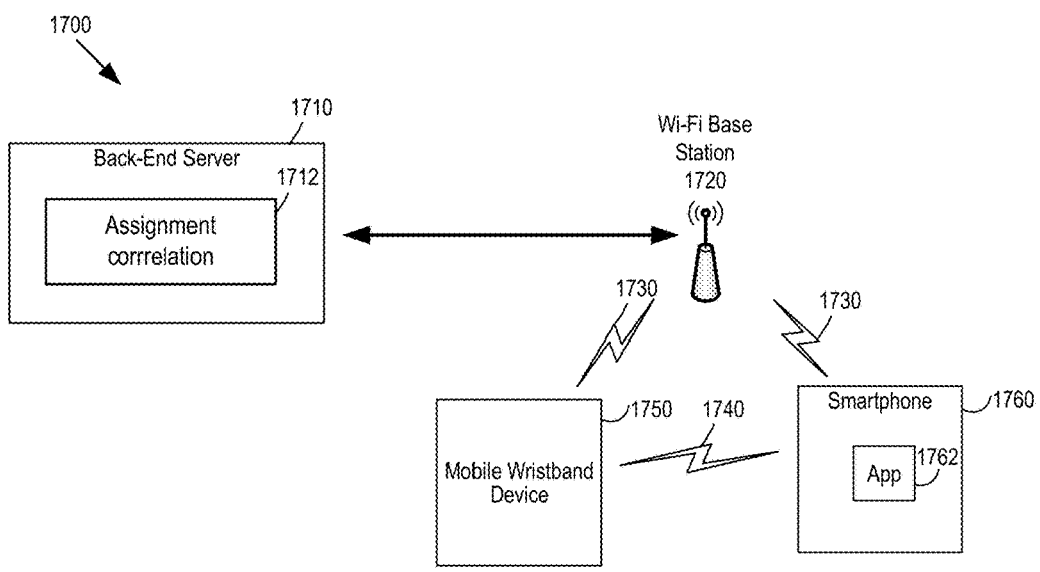
FIG. 17 is a block diagram for temporarily assigning a wristband.

FIG. 17 is a block diagram 1700 for temporarily assigning a wristband. As discussed above, the mobile wristband device 1750 may be temporarily assigned to a person for a variety of reasons. In order to do so, app 1762 on smartphone 1760 may communicate wirelessly 1740 via Bluetooth or the like with the mobile wristband device 1750 in order to obtain the identification of the mobile wristband device 1750. For example, a wristband with a highest RSSI signal may be assigned. Alternatively, the app 1762 may include a drop-down menu, or the like, that lists the available mobile wristband devices. The user may select one from the list in order to provide the identification of the mobile wristband device 1750 to the app. Still alternatively, a single wristband may be available for temporary assignment. As such, selection of the single wristband is not needed. Further, app may receive as input identification information of the person (e.g., a name or other identification). The input may be via a keyboard (not shown) of smartphone 1760. In turn, app 1762 may communicate, via wireless signals 1730 and Wi-Fi base station 1720, with back-end server 1710, thereby transmitting both the identification of the mobile wristband device 1750 and the identification of the person. In turn, back-end server 1710 may store the correlation of the identification of the mobile wristband device 1750 and the identification of the person in assignment correlation 1712. The assignment correlation 1712 may assign the identification of the mobile wristband device 1750 to the identification of the person for a limited period of time. As one example, the assignment may be for a defined limited amount of time (such as a single work shift). In one specific implementation, the assignment correlation 1712 may include an indication of the limited period of time, with the indication being a start time of the assignment (with the back-end server 1710 calculating a time period, such as 8 hours, from the start time of the assignment to indicate when the temporary assignment ends or an end time of the assignment. Alternatively, the assignment correlation 1712 may be assigned until the identification of the mobile wristband device 1750 is reassigned to another person. Further, to the extent that the back-end server 1710 includes a profile correlated to the identification of the person, the back-end server 1710 may likewise correlate the profile to the identification of the mobile wristband device 1750. In this way, a permanent worker, who forgot to bring his/her wristband to work, may still be notified and be attributed compliance data according to the assigned profile for the permanent worker.

Figure 18:
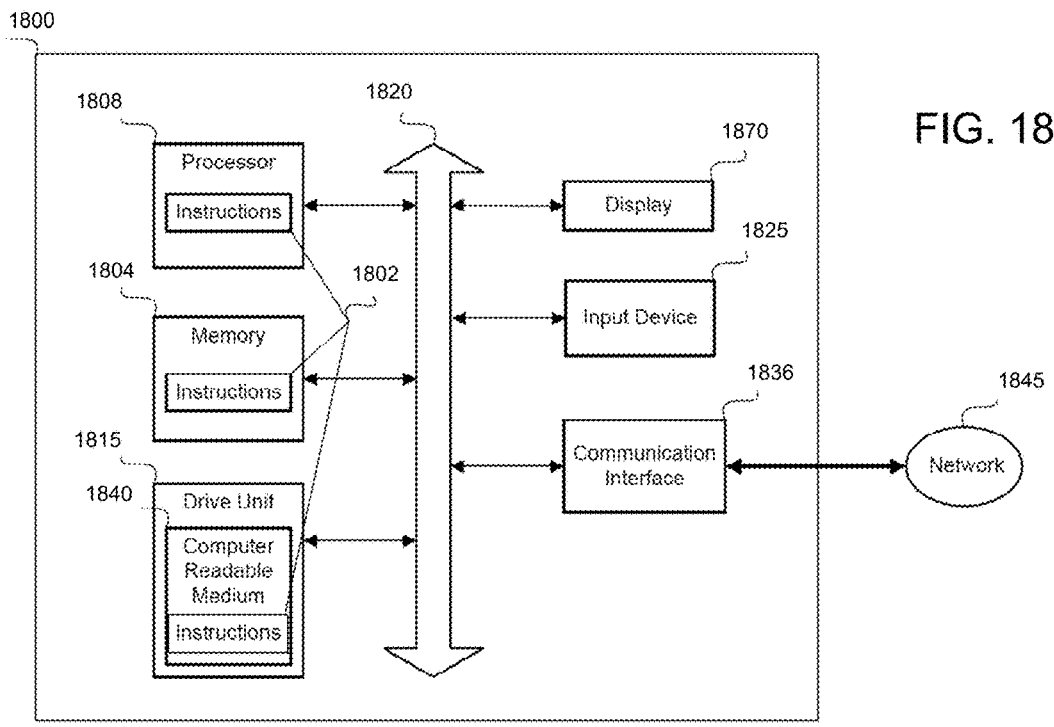
FIG. 18 is a general computer system, programmable to be a specific computer system, which may represent any of the computing devices referenced herein.

FIG. 18 is a general computer system 1800, programmable to be a specific computer system, which may represent any of the computing devices referenced herein, such as the wristband, the stationary controller, or the back-end. The computer system 1800 may include an ordered listing of a set of instructions 1802 that may be executed to cause the computer system 1800 to perform any one or more of the methods or computer-based functions disclosed herein. The computer system 1800 can operate as a stand-alone device or can be connected, e.g., using the network 1845, to other computer systems or peripheral devices.

In a networked deployment, the computer system 1800 can operate in the capacity of a server or as a client-user computer in a server-client user network environment, or as a peer computer system in a peer-to-peer (or distributed) network environment. The computer system 1800 can also be implemented as or incorporated into various devices, such as a personal computer or a mobile computing device capable of executing a set of instructions 1802 that specify actions to be taken by that machine, including and not limited to, accessing the Internet or Web through any form of browser. Further, each of the systems described can include any collection of sub-systems that individually or jointly execute a set, or multiple sets, of instructions to perform one or more computer functions.

The computer system 1800 can include a memory 1804 on a bus 1820 for communicating information. Code operable to cause the computer system to perform any of the acts or operations described herein can be stored in the memory 1804. The memory 1804 can be a random-access memory, read-only memory, programmable memory, hard disk drive or any other type of volatile or non-volatile memory or storage device.

The computer system 1800 can include a processor 1808, such as a central processing unit (CPU) and/or a graphics processing unit (GPU). In one implementation, one example of a processor is a controller. Further, one example of a controller is a microcontroller. The processor 1808 can include one or more general processors, digital signal processors, application specific integrated circuits, field programmable gate arrays, digital circuits, optical circuits, analog circuits, combinations thereof, or other now known or later-developed devices for analyzing and processing data. The processor 1808 can implement the set of instructions 1802 or other software program, such as manually programmed or computer-generated code for implementing logical functions. The logical function or any system element described can, among other functions, process and convert an analog data source such as an analog electrical, audio, or video signal, or a combination thereof, to a digital data source for audio-visual purposes or other digital processing purposes such as for compatibility for computer processing.

The computer system 1800 can also include a disk or optical drive unit 1815. The disk drive unit 1815 can include a computer-readable medium 1840 in which one or more sets of instructions 1802, e.g., software, can be embedded.

Further, the instructions 1802 can perform one or more of the operations as described herein. The instructions 1802 can reside completely, or at least partially, within the memory 1804 or within the processor 1808 during execution by the computer system 1800.

The memory 1804 and the processor 1808 also can include computer-readable media as discussed above. A "computer-readable medium," "computer-readable storage medium," "machine readable medium," "propagated-signal medium," or "signal-bearing medium" can include any device that has, stores, communicates, propagates, or transports software for use by or in connection with an instruction executable system, apparatus, or device. The machine-readable medium can selectively be, but not limited to, an electronic, magnetic, optical, electromagnetic, infrared, or semiconductor system, apparatus, device, or propagation medium.

Additionally, the computer system 1800 can include an input device 1825, such as a keyboard or mouse, configured for a user to interact with any of the components of system 1800. It can further include a display 1870, such as a liquid crystal display (LCD), a cathode ray tube (CRT), or any other display suitable for conveying information. The display 1870 can act as an interface for the user to see the functioning of the processor 1808, or specifically as an interface with the software stored in the memory 1804 or the disk drive unit 1815.

The computer system 1800 can include a communication interface 1836 that enables communications via the communications network 1845. The network 1845 can include wired networks, wireless networks, or combinations thereof. The communication interface 1836 network can enable communications via any number of communication standards, such as 802.11, 802.17, 802.20, WiMAX, 802.15.4, cellular telephone standards, or other communication standards, as discussed above. Simply because one of these standards is listed does not mean any one is preferred, as any number of these standards can never actually be adopted in a commercial product.

Block diagrams of different aspects of the system, including FIGS. 1A-4B, 8A-C, 10A-D, 12A-B, 13, and 17 may be implemented using the computer functionality disclosed in FIG. 18. Further, the flow diagrams, such as those illustrated in 6A-B, 6F-1, 7A-D, 9A-D, 11A-C, 14A-C, 15A-C, and 16, may use computer readable instructions that are executed by one or more processors in order to implement the functionality disclosed.

The present disclosure contemplates a computer-readable medium that includes instructions or receives and executes instructions responsive to a propagated signal, so that a device connected to a network can communicate voice, video, audio, images or any other data over the network. Further, the instructions can be transmitted or received over the network via a communication interface. The communication interface can be a part of the processor or can be a separate component. The communication interface can be created in software or can be a physical connection in hardware. The communication interface can be configured to connect with a network, external media, the display, or any other components in system, or combinations thereof. The connection with the network can be a physical connection, such as a wired Ethernet connection or can be established wirelessly as discussed below. In the case of a service provider server, the service provider server can communicate with users through the communication interface.

The computer-readable medium can be a single medium, or the computer-readable medium can be a single medium or multiple media, such as a centralized or distributed database, or associated caches and servers that store one or more sets of instructions. The term "computer-readable medium" can also include any medium that can be capable of storing, encoding or carrying a set of instructions for execution by a processor or that can cause a computer system to perform any one or more of the methods or operations disclosed herein.

The computer-readable medium can include a solid-state memory such as a memory card or other package that houses one or more non-volatile read-only memories. The computer-readable medium also can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an email or other self-contained information archive or set of archives can be considered a distribution medium that can be a tangible storage medium. The computer-readable medium is preferably a tangible storage medium. Accordingly, the disclosure can be considered to include any one or more of a computer-readable medium or a distribution medium and other equivalents and successor media, in which data or instructions can be stored.

Alternatively, or in addition, dedicated hardware implementations, such as application specific integrated circuits, programmable logic arrays and other hardware devices, can be constructed to implement one or more of the methods described herein. Applications that can include the apparatus and systems of various embodiments can broadly include a variety of electronic and computer systems. One or more embodiments described herein can implement functions using two or more specific interconnected hardware modules or devices with related control and data signals that can be communicated between and through the modules, or as portions of an application-specific integrated circuit. Accordingly, the present system can encompass software, firmware, and hardware implementations.

The methods described herein may be implemented by software programs executable by a computer system. Further, implementations may include distributed processing, component/object distributed processing, and parallel processing. Alternatively, or in addition, virtual computer system processing may be constructed to implement one or more of the methods or functionality as described herein.

Although components and functions are described that may be implemented in particular embodiments with reference to particular standards and protocols, the components and functions are not limited to such standards and protocols. For example, standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

The illustrations described herein are intended to provide a general understanding of the structure of various embodiments. The illustrations are not intended to serve as a complete description of all of the elements and features of apparatus, processors, and systems that utilize the structures or methods described herein. Many other embodiments can be apparent to those of skill in the art upon reviewing the disclosure. Other embodiments can be utilized and derived from the disclosure, such that structural and logical substitutions and changes can be made without departing from the scope of the disclosure. Additionally, the illustrations are merely representational and cannot be drawn to scale. Certain proportions within the illustrations may be exaggerated, while other proportions may be minimized. Accordingly, the disclosure and the figures are to be regarded as illustrative rather than restrictive.

The above disclosed subject matter is to be considered illustrative, and not restrictive, and the appended claims are intended to cover all such modifications, enhancements, and other embodiments, which fall within the true spirit and scope of the description. Thus, to the maximum extent allowed by law, the scope is to be determined by the broadest permissible interpretation of the following claims and their equivalents, and shall not be restricted or limited by the foregoing detailed description.

The following example embodiments of the invention are also disclosed:

Embodiment 1: A method for automatically periodically checking whether a worker has complied with a hygiene protocol, the method comprising: (A) automatically determining whether the worker has complied with the hygiene protocol; (B) responsive to automatically determining that the worker has complied with the hygiene protocol, automatically determining a time at which the worker complied with the hygiene protocol and designating the time as a last time at which the worker complied with the hygiene protocol; (C) responsive to automatically determining that the worker has not complied with the hygiene protocol, determining an elapsed time since the last time at which the worker complied with the hygiene protocol; and (D) responsive to automatically determining that the elapsed time is greater than or equal to a predetermined interval between compliance actions, generating an output indicative to the worker to comply with the hygiene protocol and iterating back to (A).

Embodiment 2: The method of embodiment 1, wherein the predetermined interval is dynamic.

Embodiment 3: The method of embodiment 2, wherein the predetermined interval is dynamic based on a time of day.

Embodiment 4: The method of embodiment 2, wherein the predetermined interval is dynamic based on a status of the worker.

Embodiment 5: The method of embodiment 2, wherein the predetermined interval is dynamic based on a status of the worker and based on a time of day.

Embodiment 6: The method of embodiment 1, wherein a mobile electronic device associated with the worker automatically determines whether the worker has complied with the hygiene protocol; and wherein the output is generated on a stationary device proximate to the worker.

Embodiment 7: A method for automatically checking whether a worker has complied with a hygiene protocol, the method comprising:
automatically determining a hygiene opportunity by: automatically determining a location of the worker within a first subsection of a designated area, the designated area being divided into a plurality of subsections; and automatically determining a transition from the first subsection of the designated area to a second subsection of the designated area thereby indicating the hygiene opportunity; responsive to automatically determining the hygiene opportunity:
automatically determining whether the worker has complied with the hygiene protocol; and
responsive to determining that the worker has not complied with the hygiene protocol, generating an output indicative to the worker to perform at least one action associated with the hygiene protocol.

Embodiment 8: The method of embodiment 7, wherein the designated area comprises a dining area with a plurality of dining tables; and
wherein the plurality of subsections comprise separately defined sections associated with different tables of the plurality of dining tables.

Embodiment 9: The method of embodiment 7, further comprising: determining a type of worker; and selecting the plurality of subsections of the designated area dependent on the type of worker.

Embodiment 10: A system comprising one or more electronic devices to perform the functions of embodiments 1-9.

Embodiment 11: A system for automatically checking whether a worker has complied with a hygiene protocol, the system comprising:
one or more electronic devices configured to:
automatically determine a hygiene opportunity by:
automatically determine a location of the worker within a first subsection of a designated area, the designated area being divided into a plurality of subsections; and
automatically determine a transition from the first subsection of the designated area to a second subsection of the designated area thereby indicating the hygiene opportunity;
responsive to automatically determining the hygiene opportunity:
automatically determine whether the worker has complied with the hygiene protocol; and
responsive to determining that the worker has not complied with the hygiene protocol, generate an output indicative to the worker to perform at least one action associated with the hygiene protocol.

Embodiment 12: A method for assigning a wearable mobile electronic device for temporarily monitoring hygiene of a person, the method comprising: accessing an app for assigning the wearable mobile electronic device, the app comprising an interface for selecting at least one wristband and inputting an identification for the person; responsive to receiving the selection of the at least one wristband and the identification of the person, associating the at least one wristband with the identification of the person for a limited time defined by one of a predetermined period or until the at least one wristband is assigned again; accessing a profile associated with the identification of the person, the profile indicative of one or both of analytics or notification for hygiene; and using the profile in order to perform one or both of: determining reminders for output via the wearable mobile electronic device in order to remind the person to perform hygiene compliance; or associating actions performed by the wearable mobile electronic device for the hygiene compliance with the profile.

Embodiment 13: A system comprising one or more electronic devices to perform the functions of embodiment 12.

Embodiment 14: A dispenser monitoring device integrated or associated with a dispenser, the dispenser, responsive to a request for a dispense of hand cleaning agent, is configured to dispense a premeasured amount of the hand cleaning agent, the dispenser monitoring device comprising: hand cleaning agent dispensing detector configured to detect whether the dispenser has dispensed the premeasured amount of the hand cleaning agent; at least one memory configured to store identification of one or both of the dispenser monitoring device or the dispenser; communication functionality; and a processor in communication with the hand cleaning agent dispensing detector, the memory and the communication functionality, the processor configured to:

receive, from the hand cleaning agent dispensing detector, an indication that the dispenser has dispensed the premeasured amount of the hand cleaning agent;

responsive to receiving the indication: perform one or both of:

revise an indication of a remaining amount of hand cleaning agent in the dispenser;

determine whether the indication of the remaining amount of hand cleaning agent in the dispenser is less than a predetermined number; and responsive to determining that the indication of the remaining amount of hand cleaning agent in the dispenser is less than the predetermined number, generate an output; or send a communication to a server indicative of the identification of one or both of the dispenser monitoring device or the dispenser and of a dispense in order for the server to revise the indication of the remaining amount of hand cleaning agent in the dispenser, determine whether the indication of the remaining amount of hand cleaning agent in the dispenser is less than the predetermined number, and responsive to determining that the indication of the remaining amount of hand cleaning agent in the dispenser is less than the predetermined number, generate a server output.

Embodiment 15: The dispenser monitoring device of embodiment 14, wherein the processor is further configured to: receive, from a server, a server communication indicative that the dispenser has been refilled; and responsive to receiving the server communication, reset an indication of a remaining amount of hand cleaning agent in the dispenser; and wherein the processor, responsive to receiving the indication, is configured to:

revise the indication of the remaining amount of hand cleaning agent in the dispenser;

determine whether the indication of the remaining amount of hand cleaning agent in the dispenser is less than the predetermined number; and responsive to determining that the indication of the remaining amount of hand cleaning agent in the dispenser is less than the predetermined number, generate the output.

Embodiment 16: The dispenser monitoring device of embodiments 14-15, wherein the output comprises a communication to the server, the communication indicative to the server that the remaining amount of hand cleaning agent in the dispenser is less than the predetermined number in order for the server to generate an electronic communication to a mobile electronic device to refill the dispenser.

Embodiment 17: The dispenser monitoring device of embodiments 14-16, further comprising a speaker or a light; and wherein the output comprises an aural output generated by the speaker or a visual output generated by the light.

Embodiment 18: The dispenser monitoring device of embodiments 14-17, wherein the indication of a remaining amount of hand cleaning agent in the dispenser comprises a counter indicative of a remaining number of dispenses from the dispenser; and wherein revising the indication of the remaining amount of hand cleaning agent in the dispenser comprises decrementing the counter.

Embodiment 19: The dispenser monitoring device of embodiments 14-18, wherein the communication functionality comprises farther-field communication with the server;

and wherein the processor is further configured to: receive, via the farther-field communication from the server, a polling request, the polling request indicative to the dispenser monitoring device to transmit the indication of a remaining amount of the hand cleaning agent in the dispenser; and responsive to receiving the polling request, transmit the indication of the remaining amount of the hand cleaning agent in the dispenser.

Embodiment 20: The dispenser monitoring device of embodiments 14-19, wherein the communication functionality comprises near-field communication functionality with a mobile electronic device and for farther-field communication with the server; wherein the processor further configured to: receive a request from the mobile electronic device to transmit the identification of one or both of the dispenser monitoring device or the dispenser; and responsive to receiving the request, transmit, via near-field communication, the identification of one or both of the dispenser monitoring device or the dispenser; and wherein the processor is configured to receive, via the farther-field communication from the server, the server communication responsive to the dispenser monitoring device transmitting the identification to the mobile electronic device, which in turn transmits a refill communication to the server.

Embodiment 21: The dispenser monitoring device of embodiments 14-20, wherein the near-field communication comprises Bluetooth communication; and wherein the farther-field communication comprises Wi-Fi communication.

Embodiment 22: The dispenser monitoring device of embodiments 14-21, wherein the server output comprises an electronic communication to a mobile device to refill the dispenser.

Embodiment 23: A computer-implemented method for determining whether to refill a dispenser, the method comprising: receiving a communication indicative that the dispenser has been refilled; responsive to receiving the communication, reset an indication of a remaining amount of hand cleaning agent in the dispenser; receiving, from a hand cleaning agent dispensing detector, an indication that the dispenser has dispensed the hand cleaning agent; and responsive to receiving the indication: revising an indication of a remaining amount of hand cleaning agent in the dispenser; determining whether the indication of the remaining amount of hand cleaning agent in the dispenser is less than a predetermined number; and responsive to determining that the indication of the remaining amount of hand cleaning agent in the dispenser is less than the predetermined number, generating an output indicative to refill the dispenser.

Embodiment 24: The method of embodiment 23, wherein a dispenser monitoring device integrated or associated with a dispenser performs the following: receives, from a server, a server communication indicative that the dispenser has been refilled; responsive to receiving the server communication, resets the indication of a remaining amount of hand cleaning agent in the dispenser; revises the indication of the remaining amount of hand cleaning agent in the dispenser; determines whether the indication of the remaining amount of hand cleaning agent in the dispenser is less than the predetermined number; and responsive to determining that the indication of the remaining amount of hand cleaning agent in the dispenser is less than the predetermined number, generates the output.

Embodiment 25: The method of embodiments 23-24, wherein the output comprises a communication to the server, the communication indicative to the server that the remaining amount of hand cleaning agent in the dispenser is less than the predetermined number in order for the server to generate an electronic communication to a mobile electronic device to refill the dispenser.

Embodiment 26: The method of embodiments 23-25, wherein the output comprises an aural output generated by a speaker or a visual output generated by a light.

Embodiment 27: The method of embodiments 23-26, further comprising: receiving, via farther-field communication from the server, a polling request, the polling request indicative to the dispenser monitoring device to transmit the indication of a remaining amount of the hand cleaning agent in the dispenser; and responsive to receiving the polling request, transmitting the indication of the remaining amount of the hand cleaning agent in the dispenser.

Embodiment 28: The method of embodiments 23-27, further comprising: receiving a request from a mobile electronic device to transmit an identification of one or both of the dispenser monitoring device or the dispenser; responsive to receiving the request, transmitting, via near-field communication, the identification of one or both of the dispenser monitoring device or the dispenser; and receiving, via farther-field communication from the server, the server communication responsive to the dispenser monitoring device transmitting the identification to the mobile electronic device, which in turn transmits a refill communication to the server.

Embodiment 29: The method of embodiments 23-28, wherein a server performs the following: receiving the communication indicative that the dispenser has been refilled; responsive to the communication, resetting the indication of the remaining amount of hand cleaning agent in the dispenser; revising the indication of the remaining amount of hand cleaning agent in the dispenser; determining whether the indication of the remaining amount of hand cleaning agent in the dispenser is less than a predetermined number; and responsive to determining that the indication of the remaining amount of hand cleaning agent in the dispenser is less than the predetermined number, generating the output indicative to refill the dispenser; and wherein a dispenser monitoring device integrated or associated with a dispenser performs the following: receiving, from the hand cleaning agent dispensing detector, an indication that the dispenser has dispensed a premeasured amount of the hand cleaning agent; and responsive to receiving the indication, sending a communication to the server indicative of an identification of one or both of the dispenser monitoring device or the dispenser and of a dispense in order for the server to revise the indication of the remaining amount of hand cleaning agent in the dispenser, determine whether the indication of the remaining amount of hand cleaning agent in the dispenser is less than the predetermined number, and responsive to determining that the indication of the remaining amount of hand cleaning agent in the dispenser is less than the predetermined number, generate a server output.

Embodiment 30: A computer-implemented method for determining whether an identified hand hygiene opportunity is to be used for compliance statistics for a healthcare worker, the method comprising: responsive to identifying the hand hygiene opportunity, accessing at least one, some or all of a status of the healthcare worker, a schedule of the healthcare worker, or a location of the healthcare worker; determining, based on the at least one, some or all of a status of the healthcare worker, a schedule of the healthcare worker, or the location of the healthcare worker, whether the hand hygiene opportunity is to be used for compliance statistics for the healthcare worker; and responsive to determining that the hand hygiene opportunity is not to be used for compliance statistics for the healthcare worker, performing at least one action or failing to perform at least one action that results in the hand hygiene opportunity not being used for compliance statistics for the healthcare worker.

Embodiment 31: The method of embodiment 30, wherein the status of the healthcare worker comprises a physical therapist; wherein the schedule of the healthcare worker is indicative of performing physical therapy for a patient; and wherein determining whether the hand hygiene opportunity is to be used for compliance statistics for the healthcare worker is based on the status of the healthcare worker being the physical therapist and the schedule of the healthcare worker being indicative of performing physical therapy for the patient.

Embodiment 32: The method of embodiments 30-31, wherein performing the at least one action or failing to perform the at least one action that results in the hand hygiene opportunity not being used for compliance statistics for the healthcare worker comprises a mobile electronic device associated with the healthcare worker determining not to perform a compliance determination for the hand hygiene opportunity.

Embodiment 33: The method of embodiments 30-32, wherein performing the at least one action or failing to perform the at least one action that results in the hand hygiene opportunity not being used for compliance statistics for the healthcare worker comprises: a mobile electronic device associated with the healthcare worker determining to perform a compliance determination for the hand hygiene opportunity; and the mobile electronic device determining not to transmit the compliance determination to a backend server tasked with compiling data used to perform the compliance statistics for the healthcare worker.

Embodiment 34: The method of embodiments 30-33, wherein performing the at least one action or failing to perform the at least one action that results in the hand hygiene opportunity not being used for compliance statistics for the healthcare worker comprises: a mobile electronic device associated with the healthcare worker determining to perform a compliance determination for the hand hygiene opportunity; and transmitting, by the mobile electronic device, one or more communications to a backend server, the one or more communications indicative of the compliance determination for the hand hygiene opportunity performed by the mobile electronic device and an indication that the compliance determination is not to be used for compliance statistics for the healthcare worker.

Embodiment 35: The method of embodiments 30-34, wherein the indication that the compliance determination is not to be used for compliance statistics for the healthcare worker is indicative to the backend server not to use the compliance determination for the compliance statistics for the healthcare worker.

Embodiment 36: The method of embodiments 30-35, wherein the location of the healthcare worker comprises a location associated with a contaminated area; and wherein determining that the hand hygiene opportunity is not to be used for compliance statistics for the healthcare worker is responsive to determining that the location of the healthcare worker is the location associated with the contaminated area.

Embodiment 37: A system comprising one or more electronic devices to perform the functions of embodiments 30-36.

Embodiment 38: A computer-implemented method for determining infection analysis or workload of one or more healthcare providers, the method comprising: tracking movement or activity of the one or more healthcare providers; analyzing entrance opportunities and exit opportunities of the one or more healthcare providers in order to determine durations of interacting with one or more patients; and determining, based on the durations, one or both of the infection analysis or the workload for the one or more healthcare providers.

Embodiment 39: The method of embodiment 38, wherein the infection analysis is determined based on the durations.

Embodiment 40: The method of embodiments 38-39, further comprising: determining a status of the healthcare provider; and estimating a number of hygiene opportunities based on the duration of the healthcare provider within a patient area and the status of the healthcare provider; and wherein the infection analysis is determined based on the number of hygiene opportunities.

Embodiment 41: The method of embodiments 38-40, wherein the status of the healthcare provider comprises one of a nurse, doctor, or hospital support staff.

Embodiment 42: The method of embodiments 38-41, wherein the infection analysis comprises a root cause analysis in order to determine a ranking of a plurality of healthcare providers that contributed to an infection in the patient area.

Embodiment 43: The method of embodiments 38-42, wherein analysis of the workload is determined for the one or more healthcare providers.

Embodiment 44: A system comprising one or more electronic devices to perform the functions of embodiments 38-43.

Embodiment 45: A system for determining infection analysis or workload of one or more healthcare providers, the system comprising: one or more electronic devices configured to: track movement or activity of the one or more healthcare providers; analyze entrance opportunities and exit opportunities of the one or more healthcare providers in order to determine durations of interacting with one or more patients; and determine, based on the durations, one or both of the infection analysis or the workload for the one or more healthcare providers.

Embodiment 46: A method for performing the functions of embodiment 45.

The invention claimed is:

1. A method for identifying and determining compliance with a hygiene opportunity, the method comprising:
automatically predicting the hygiene opportunity, the hygiene opportunity indicative of interaction for which compliance is to be monitored, the compliance requiring one or more hygiene actions;
responsive to a controller automatically detecting at least one action so that the controller communicates with one or more mobile electronic devices indicative that the at least one action was performed, wherein each of the one or more mobile electronic devices are associated with a respective person, the at least one action comprising at least one of the one or more hygiene actions, automatically predicting, by a respective mobile electronic device of the one or more mobile electronic devices in communication with the controller, whether the respective person performed the at least one action; and
determining compliance or non-compliance with the hygiene opportunity dependent on automatically predicting that the respective person performed the at least one action.

2. The method of claim 1, wherein the at least one action comprises taking hand cleaning agent;
wherein automatically predicting whether the respective person performed the at least one action comprises analyzing hand movement data of the respective person, the hand movement data generated by a hand movement sensor resident on the respective mobile electronic device; and
wherein the at least one action is detected by the controller via data separate from the hand movement data.

3. The method of claim 2, wherein the controller is associated with a hand cleaning agent dispenser that dispenses hand cleaning agent and detects the at least one action of taking the hand cleaning agent from the hand cleaning agent dispenser; and
wherein the respective mobile electronic device associated with the respective person includes a hand movement sensor that generates the hand movement data.

4. The method of claim 3, wherein the controller associated with the hand cleaning agent dispenser automatically predicts the hygiene opportunity by determining whether the at least one action of taking the hand cleaning agent has been performed; and
wherein the respective mobile electronic device automatically predicts which of a plurality of people performed the at least one action of taking the hand cleaning agent by analyzing the hand movement data.

5. The method of claim 4, wherein the controller associated with the hand cleaning agent dispenser comprises a stationary controller; and
wherein the respective mobile electronic device comprises a wearable mobile electronic device associated with the respective person.

6. The method of claim 2, wherein automatically predicting whether the respective person performed the at least one action comprises the respective mobile electronic device analyzing the hand movement data in order to determine whether the analysis is indicative of hand rubbing of the hand cleaning agent.

7. The method of claim 1, wherein the controller communicates with the one or more mobile electronic devices using a broadcast communication.

8. The method of claim 1, further comprising the one or more mobile electronic devices, responsive to the controller communicating with the one or more mobile electronic devices, waking up a hand movement sensor resident on the one or more mobile electronic devices in order to generate hand movement data; and
wherein automatically predicting whether the respective person performed the at least one action comprises analyzing the hand movement data.

9. A system for identifying and determining compliance of a worker with a hygiene opportunity, the system comprising:
at least one controller configured to:
automatically predict the hygiene opportunity, the hygiene opportunity indicative of interaction for which compliance is to be monitored, the compliance requiring one or more hygiene actions;
one or more mobile electronic devices configured to:
responsive to the at least one controller automatically detecting at least one action so that the controller communicates with one or more mobile electronic devices indicative that the at least one action was performed, wherein each of the one or more mobile electronic devices are associated with a respective person, the at least one action comprising at least one of the one or more hygiene actions, automatically predict, by a respective mobile electronic device of the one or more mobile electronic devices in communication with the at least one controller, whether the respective person performed the at least one action; and wherein at least one of the at least one controller or the one or more mobile electronic devices are further configured to:
  determine compliance or non-compliance with the hygiene opportunity dependent on automatically predicting that the respective person performed the at least one action.

10. The system of claim 9, wherein the at least one action comprises taking hand cleaning agent; and
  wherein the at least one controller is associated with a dispenser configured to dispense the hand cleaning agent.

11. The system of claim 10,
  wherein the respective mobile electronic device comprises a wearable mobile electronic device associated with the respective person;
  wherein the at least one controller is configured to predict, based on communication signals with one or more wearable mobile electronic devices, which of a plurality of people took the hand cleaning agent; and
  wherein the wearable mobile electronic device is configured to automatically predict the hygiene opportunity by communicating with one or more stationary controllers.

12. The system of claim 9, wherein the at least one controller is configured to communicate with the one or more mobile electronic devices using a broadcast communication.

13. The system of claim 9, wherein the one or more mobile electronic devices, responsive to the controller communicating with the one or more mobile electronic devices, are configured to wake up a hand movement sensor resident on the one or more mobile electronic devices in order to generate hand movement data; and
  wherein the respective mobile electronic device is configured to automatically predict whether the respective person performed the at least one action by analyzing the hand movement data.

14. The system of claim 9, wherein the one or more mobile electronic devices include a hand movement sensor resident on each of the one or more mobile electronic devices, the hand movement sensor configured to generate hand movement data; and
  wherein the respective mobile electronic device is configured to predict whether the respective person performed the at least one action by analyzing hand movement data of the respective person.

15. The system of claim 14, wherein the at least one controller is associated with a hand cleaning agent dispenser configured to dispense hand cleaning agent and to detect the at least one action of taking the hand cleaning agent from the hand cleaning agent dispenser; and
  wherein the respective mobile electronic device is configured to automatically predict whether the respective person performed the at least one action by the respective mobile electronic device analyzing the hand movement data in order to determine whether the analysis is indicative of hand rubbing of the hand cleaning agent.

* * * * *